(12) United States Patent
Edinger et al.

(10) Patent No.: US 8,562,972 B2
(45) Date of Patent: Oct. 22, 2013

(54) METHODS AND COMPOSITIONS FOR TREATMENT OF BONE DEFECTS WITH PLACENTAL CELL POPULATIONS

(75) Inventors: James W. Edinger, Belford, NJ (US); Robert J. Hariri, Florham Park, NJ (US); Jia-Lun Wang, Cherry Hill, NJ (US); Qian Ye, Livingston, NJ (US); Kristen S. Labazzo, Springfield, NJ (US); Marian Pereira, Cranford, NJ (US); Sascha Dawn Abramson, Hillsborough, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 877 days.

(21) Appl. No.: 11/877,475

(22) Filed: Oct. 23, 2007

(65) Prior Publication Data

US 2008/0213228 A1 Sep. 4, 2008

Related U.S. Application Data

(60) Provisional application No. 60/853,971, filed on Oct. 23, 2006, provisional application No. 60/855,629, filed on Oct. 30, 2006, provisional application No. 60/997,022, filed on Sep. 28, 2007.

(51) Int. Cl.
  *C12N 5/00* (2006.01)
  *A61K 35/50* (2006.01)

(52) U.S. Cl.
  USPC .......... 424/93.7; 424/422; 424/484; 424/583; 435/325

(58) Field of Classification Search
  USPC .............. 424/93.7, 422, 484, 583; 435/325
  See application file for complete search history.

(56) References Cited

U.S. PATENT DOCUMENTS

| | | | |
|---|---|---|---|
| 5,197,985 A | 3/1993 | Caplan et al. |
| 5,226,914 A | 7/1993 | Caplan et al. |
| 5,356,373 A | 10/1994 | Dracker et al. |
| 5,486,359 A | 1/1996 | Caplan et al. |
| 5,516,532 A | 5/1996 | Atala et al. |
| 5,716,616 A | 2/1998 | Prockop et al. |
| 5,733,542 A | 3/1998 | Haynesworth et al. |
| 5,811,094 A | 9/1998 | Caplan et al. |
| 5,827,740 A | 10/1998 | Pittenger |
| 5,855,619 A | 1/1999 | Caplan et al. |
| 5,908,784 A | 6/1999 | Johnstone et al. |
| 5,919,702 A | 7/1999 | Purchio et al. |
| 5,922,597 A | 7/1999 | Verfaillie et al. |
| 5,942,225 A | 8/1999 | Bruder et al. |
| 6,020,469 A | 2/2000 | Hershenson |
| 6,022,743 A | 2/2000 | Naughton et al. |
| 6,174,333 B1 | 1/2001 | Kadiyala et al. |
| 6,355,239 B1 | 3/2002 | Bruder et al. |
| 6,358,737 B1 | 3/2002 | Bonewald et al. |
| 6,387,367 B1 | 5/2002 | Davis-Sproul et al. |
| 6,541,024 B1 | 4/2003 | Kadiyala et al. |
| 6,685,936 B2 | 2/2004 | McIntosh et al. |
| 6,835,377 B2 | 12/2004 | Goldberg et al. |
| 6,863,900 B2 | 3/2005 | Kadiyala et al. |
| 7,045,148 B2 | 5/2006 | Hariri |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,682,803 B2 | 3/2010 | Paludan et al. |
| 7,700,090 B2 | 4/2010 | Heidaran et al. |
| 2001/0038836 A1 | 11/2001 | During et al. |
| 2001/0044124 A1 | 11/2001 | Bacus |
| 2002/0102239 A1 | 8/2002 | Koopmans |
| 2002/0123141 A1 | 9/2002 | Hariri |
| 2002/0160510 A1 | 10/2002 | Hariri |
| 2003/0032179 A1 | 2/2003 | Hariri |
| 2003/0044976 A1 | 3/2003 | Dominko et al. |
| 2003/0044977 A1 | 3/2003 | Sakuragawa et al. |
| 2003/0161818 A1 | 8/2003 | Weiss et al. |
| 2003/0180269 A1 | 9/2003 | Hariri |
| 2003/0235563 A1 | 12/2003 | Strom et al. |

(Continued)

FOREIGN PATENT DOCUMENTS

| | | |
|---|---|---|
| EP | 1288293 A1 | 3/2003 |
| EP | 1384775 A1 | 1/2004 |

(Continued)

OTHER PUBLICATIONS

Xu et al. 2004. High sensitivity of megakaryocytic progenitor cells contained in placental/umbilical cord blood to the stresses during cryopreservation. Bone Marrow Transplantation 34, 537-543.*
U.S. Appl. No. 11/982,211, filed Oct. 31, 2007, Heidaran et al.
U.S. Appl. No. 12/030,161, filed Feb. 12, 2008, Edinger et al.
U.S. Appl. No. 12/030,170, filed Feb. 12, 2008, Edinger et al.
Notice of Allowance in U.S. Appl. No. 10/004,942, now US Patent No. 7,045,148.
Office Action dated Dec. 16, 2004 in U.S. Appl. No. 10/004,942, now US Patent No. 7,045,148.
Office Action dated Dec. 5, 2003 in U.S. Appl. No. 10/004,942, now US Patent No. 7,045,148.
Office Action dated Jun. 15, 2004 in U.S. Appl. No. 10/004,942, now US Patent No. 7,045,148.

(Continued)

*Primary Examiner* — Taeyoon Kim
(74) *Attorney, Agent, or Firm* — Jones Day

(57) ABSTRACT

Provided herein are methods of using adherent placental stem cells and placental stem cell populations, and methods of culturing, proliferating and expanding the same. Also provided herein are methods of differentiating the placental stem cells. Further provided herein are methods of using the placental stem cells to formulate implantable or injectable compositions suitable for administration to a subject. Still further provided herein are provides methods for treating bone defects with stem cells and compositions comprising stem cells.

20 Claims, 26 Drawing Sheets

(56) References Cited

U.S. PATENT DOCUMENTS

Figure 1:
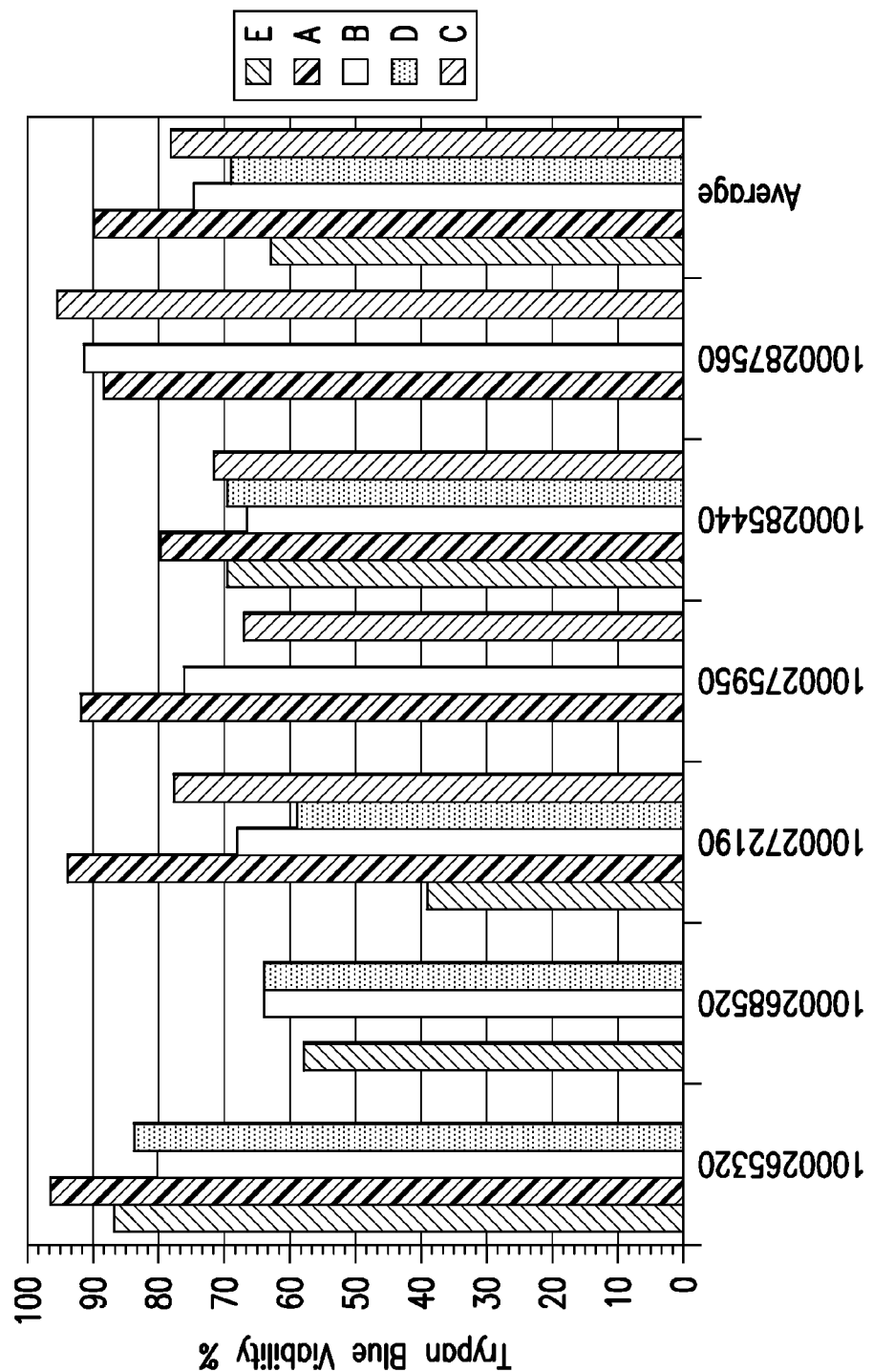

| | | |
|---|---|---|
| 2003/0235909 A1 | 12/2003 | Hariri |
| 2004/0028660 A1 | 2/2004 | Hariri |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0219136 A1 | 11/2004 | Hariri |
| 2004/0229351 A1 | 11/2004 | Rodriguez |
| 2005/0019865 A1* | 1/2005 | Kihm et al. .......... 435/69.1 |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper |
| 2005/0089513 A1 | 4/2005 | Sakuragawa et al. |
| 2005/0118715 A1 | 6/2005 | Hariri |
| 2005/0143420 A1 | 6/2005 | Moutouh-de Parseval et al. |
| 2005/0176139 A1 | 8/2005 | Chen et al. |
| 2005/0181502 A1 | 8/2005 | Furcht et al. |
| 2005/0233452 A1 | 10/2005 | Ho et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0060494 A1 | 3/2006 | Goodman et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0092497 A1 | 4/2007 | Hariri |
| 2007/0116682 A1 | 5/2007 | Atala et al. |
| 2007/0122903 A1 | 5/2007 | Rezania et al. |
| 2007/0134210 A1 | 6/2007 | Heidaran et al. |
| 2007/0141700 A1 | 6/2007 | Harmon |
| 2007/0160588 A1 | 7/2007 | Kihm et al. |
| 2007/0190034 A1 | 8/2007 | Paludan et al. |
| 2007/0190042 A1 | 8/2007 | Edinger et al. |
| 2007/0243172 A1 | 10/2007 | Ra et al. |
| 2007/0253931 A1 | 11/2007 | Varney et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0126482 A1 | 5/2009 | Heidaran et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |

FOREIGN PATENT DOCUMENTS

| | | |
|---|---|---|
| EP | 1775341 | 4/2007 |
| JP | 2003235549 | 12/2002 |
| JP | 2005151907 | 11/2003 |
| WO | WO 91/06666 | 5/1991 |
| WO | WO 95/22611 A2 | 8/1995 |
| WO | WO 95/22611 A3 | 8/1995 |
| WO | WO 96/39101 A1 | 12/1996 |
| WO | WO 02/46373 A1 | 6/2002 |
| WO | WO 02/063962 A | 8/2002 |
| WO | WO 02/064755 | 8/2002 |
| WO | WO 03/042405 | 5/2003 |
| WO | WO 03/068937 | 8/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/047770 | 6/2004 |
| WO | WO 2004/071283 | 8/2004 |
| WO | WO 2004/087896 | 10/2004 |
| WO | WO 2005/017117 | 2/2005 |
| WO | WO 2005/097190 | 10/2005 |
| WO | WO 2005/105992 | 11/2005 |
| WO | WO 2006/015214 | 2/2006 |
| WO | WO 2007/024441 | 3/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/079183 | 7/2007 |
| WO | WO 2007/087293 | 8/2007 |
| WO | WO 2008/019148 | 2/2008 |
| WO | WO 2008/051568 | 5/2008 |
| WO | WO 2008/100497 | 8/2008 |

OTHER PUBLICATIONS

Office Action dated Jun. 20, 2005 in U.S. Appl. No. 10/004,942, now US Patent No. 7,045,148.

Office Action dated May 7, 2003 in U.S. Appl. No. 10/004,942, now US Patent No. 7,045,148.

Notice of Allowance in U.S. Appl. No. 10/074,976, now US Patent No. 7,311,904.

Office Action dated Jan. 5, 2006 in U.S. Appl. No. 10/074,976, now US Patent No. 7,311,904.

Office Action dated Mar. 27, 2007 in U.S. Appl. No. 10/074,976, now US Patent No. 7,311,904.

Office Action dated Sep. 20, 2006 in U.S. Appl. No. 10/074,976, now US Patent No. 7,311,904.

(56) References Cited

OTHER PUBLICATIONS

Office Action dated Sep. 23, 2004 in U.S. Appl. No. 10/074,976, now US Patent No. 7,311,904.
Office Action dated Aug. 28, 2003 in U.S. Appl. No. 10/076,180.
Office Action dated Jun. 20, 2005 in U.S. Appl. No. 10/076,180.
Office Action dated Mar. 18, 2004 in U.S. Appl. No. 10/076,180.
Office Action dated Oct. 20, 2004 in U.S. Appl. No. 10/076,180.
Notice of Allowance in U.S. Appl. No. 10/366,671, now US Patent No. 7,311,905.
Office Action dated Jan. 19, 2006 in U.S. Appl. No. 10/366,671, now US Patent No. 7,311,905.
Office Action dated May 14, 2007 in U.S. Appl. No. 10/366,671, now US Patent No. 7,311,905.
Office Action dated Oct. 10, 2006 in U.S. Appl. No. 10/366,671, now US Patent No. 7,311,905.
Notice of Allowance in U.S. Appl. No. 10/640,428, now US Patent No. 7,255,879.
Office Action dated Oct. 18, 2006 in U.S. Appl. No. 10/640,428, now US Patent No. 7,255,879.
Office Action dated Dec. 28, 2006 in U.S. Appl. No. 10/721,144.
Office Action dated Feb. 5, 2008 in U.S. Appl. No. 10/721,144.
Office Action dated Jan. 11, 2006 in U.S. Appl. No. 10/721,144.
Office Action dated Jun. 14, 2006 in U.S. Appl. No. 10/721,144.
Office Action dated Jun. 27, 2007 in U.S. Appl. No. 10/721,144.
Office Action dated Oct. 4, 2005 in U.S. Appl. No. 10/721,144.
Office Action dated Apr. 6, 2007 in U.S. Appl. No. 10/874,828.
Office Action dated Dec. 13. 2007 in U.S. Appl. No. 10/874,828.
Office Action dated Jun. 12, 2006 in U.S. Appl. No. 10/874,828.
Office Action dated Sep. 9, 2008 in U.S. Appl. No. 10/874,828.
Office Action dated Apr. 20, 2007 in U.S. Appl. No. 11/187,400.
Office Action dated Jan. 4, 2008 in U.S. Appl. No. 11/187,400.
Addison et al., "Metabolism of Prednisolone by the Isolated Perfused Human Placental Lobule", J. Ster. Biochem Mol. Biol., vol. 39 No. 1, pp. 83-90 (1991).
Ashihara et al. "Successful Peripheral Blood Stem Cell Transplantation for Myelodysplastic Syndrome," *Bone Marrow Transplantation* (1999) 24(12): 1343-1345.
Belvedere et al., "Increased blood volume and CD34(+)CD38(−) progenitor cell recovery using a novel umbilical cord blood collection system," *Stem Cells* (2000) vol. 18(4):245-251.
Campagnoli et al., Blood (2001) Oct. 15; 98(8):2396-2402.
Caplan, "The Mesengenic Process," Clin Plast Surg (1994) 21(3):429-435.
Chao, et al., "Stem Cell Transplantation (Cord Blood Transplants)." *American Society of Hematology* (2004) p. 354-371.
Chen et al. "Intravaneous Administration of Human Umbilical Cord Reduces Behavioral Deficits after Stroke in Rats," *Stroke* (2001) 32(11): 2682-2688.
Chen, R. et al., "The Potential for the Use of Mononuclear Cells from Human Umbilical Cord Blood in the Treatment of Amyotrophic Lateral Sclerosis is SOD1 Mice," *J. Med.* (2000) 31(1-2):21-30.
Clark David A et al, "Placental trophoblast from successful human pregnancies expresses the tolerance signaling molecule, CD200 (OX-2)" American Journal of Reproductive immunology, Munksgaard International Publishers, Copenhagen, DK, vol. 50, No. 3, Sep. 2003, pp. 187-195, XP002430047 ISSN: 1046-7408.
Contractor et al., 1984, "A comparison of the effects of different perfusion regimens on the structure of the isolated human placental lobule," Cell Tissue Res. 237:609-617.
Cosma, et al., "Use and Application of Stem Cells in Toxicology." SOT 2003 Annual Meeting, p. 4, Abstract 19.
Czarneski, J. et al., "Effects of Cord Blood Transfer on the Hematopoietic Recovery Following Sublethal Irradiation in MRL 1pr/lpr Mice," *Proc. Soc. Exp. Biol. Med.* (1999) 220(2):79-87.
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21 , Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," *J. Urology* 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.
Drake, P.M. et al., "Human Placental Cytotrophoblasts Attract Monocytes and CD56 (bright) Natural Killer Cells Via the Actions of Monocyte Inflammatory Protein 1 alpha," *The Journal of Experimental Medicine* (2001) 193(10):1199-1212.
Elchalal et al., "Postpartum unbilical cord blood collection for transplantation: a comparison of three methods," *Am. J. of Obstetrics & Gyn.* (2000) vol. 182(1 Pt 1):227-232.
Ende, N. & Chen, R., "Parkinson's Disease Mice and Human Umbilical Cord Blood," *Journal of Medicine* (2002) 33(1-4):173-180.
Ende, N. et al., "Human Umbilical Cord Blood Cells Amerliorate Alzheimer's Disease in Transgenic Mice, " *J. Med.* (2001) 32(3-4):241-7.
Ende, N. et al., "Human Umbilical Cord Blood Cells Ameliorate Huntington's Disease in Transgenic Mice," *J. Med.*, (2001) 32(3-4):231-40).
Ende, N. et al., "The Effect of Human Cord Blood on SJL/J Mice After Chemoablation and Irradiation and Its Possible Clinical Significance," *lmmunol. Invest.* (1995) 24(6):999-1012.
Ende, N., "Berashis Cells in Human Umbilical Cord Blood vs. Embryonic Stem Cells," *Journal of Medicine* (2002) 33(1-4):167-171.
Ende, N., et al., "Human Umbilical Cord Blood Effect on SOD Mice (Amyotrophic Lateral Sclerosis)," *Life Sci.* (2001) 67(1):53-9.
Ende, N., et al., "The Feasibility of Using Blood Bank-Stored (4 Degrees C) Cord Blood, Unmatched for HLA for Marrow Transplantation," *Am. J. Clin. Pathol.* (1999) III (6):773-81.
Erices et al., "Mesenchymal progenitor cells in human umbilical cord blood," *Br. J. Haemotol.* 109(1):Abstract (2000).
Fasouliotis et al., "Human umbilical cord blood banking and transplantation: a state of the art," *Eur. J. Obstet. Gynecol. Reprod. Biol.* 90(1):13-25 (2000).
Frank H G, et al., "Cell culture models of human trophoblast: primary culture of trophoblast—a workshop report." Placent Apr. 2001, vol. 22 Suppl A, Apr. 2001, pp. S107-S109, XP002443188 ISSN: 0143-4004.
Gluckman et al., "Cord Blood Heamatopoietic Stem Cells: Biology and Transplantation," *In: Hematology, American Society of Hematology Education Program Book* (1998) p. 1-14.
Gluckman et al., "Results of Unrelated Umbilical Cord Blood Hematipoeietic Stem Cell Transplant," *Transfusion Cinique et Biologique* (2001) 8(3):146-154.
Harbacheuski, et al., "Placenta Derived Adherent Cells (PDACs) Supress Tumor Cells of Diverse Origin." Blood, vol. 108, No. 11, Part 2, Nov. 2006, p. 288b.
Huss, Stem Cells (2000) 18:1-9.
Igura, K., et al, "Isolation and Characterization of Mesencymal Progenitor Cells from Chorionic Villi of Human Placenta," *Cytotherapy* (2004) 6(6): 543-553.
International Search Report and Written Opinion from PCT/US2007/022545 dated May 28, 2008.
Jorgensen et al., 2002, The Journal of Biological Chemistry, 277: 7574-7580.
Kurtzberg et al., 1996. Placental blood as a source of hematopoietic stem cells for transplantation into unrelated recipients. N. Engl J Med. 335:157-166.
Lebkowski, Cancer J. (2001) Nov.-Dec. 7 Suppl 2:S83-93.
Leonard et al., "The Role of ABC Transporters in Clinical Practice," *Oncologist*. (2003) 8:411-424.
Li Chang Dong et al, "Mesenchymal stem cells derived from human placenta suppress allogeneic umbilical cord blood lymphocyte proliferation," Cell Research—XIBAO YANJIU Beijing, CN, vol. 15, No. 7, Jul. 2005, pp. 539-547, XP009080356 ISSN: 1001-0602.

(56) References Cited

OTHER PUBLICATIONS

Lin Yi, et al. "Murine CD200(+)CK7(+) trophoblasts in a poly (I:C)-induced embryo resorption model." Reproduction (Cambridge), vol. 130, No. 4, Oct. 2005, pp. 529-537, XP002443406 ISSN: 1470-1626.
Ma et al., "Development of an in vitro human placenta model by the cultivation of human ytophoblasts in a fiber-based bioreactor system," *Tissue Engineering* (1995) 5:91-102.
Ma et al., (1999), J. biomed Mater Res., 46: 60-72.
McMaster, M. et al, "Human Placental HLA-G Expression is Restricted to Differentiated Cytotrophoblasts," *Journal of Immunology, The Williams and Wilkins Co.* (1995) 154(8): 3771-3778.
Melchner, et al., "Human placental conditioned medium reverses apparent commitment to differentiation of human promyelocytic leukemia cells (HL60)," *Blood.* (1985) 66(6):1469-72.
Miki, et al., "Isolation of Multipotent Stem Cells from Placenta." AASLD Abstracts, HEPATOLOGY, Oct. 2003, Abstract 279, p. 290A.
Miki, et al., "Production of Hepatocytes from Human Amniotic Stem Cells." HEPATOLOGY, Abstract 20, vol. 36, No. 4, Pt. 2, 2002.
Miki, et al., "Stem Cell Characteristics of Amniotic Epithelial Cells." Stem Cells Express, published online Aug. 9, 2005; doi:10. 1634/stemcells.2004-0357.
Minguell et al., "Mesenchymal Stem Cells," *Exp Biol Med* (2001) 226:507-520.
Moore et al., "A simple perfusion technique for isolation of maternal intervillous blood mononuclear cells from human placentae," J. Immunol. Methods (1997) 209(1):93-104.
Mühlemann et al., "Cytomegalovirus in the Perfused Human Term Placenta in Vitro," *Placenta* (1995) 16:367-373.
Myllynen "In Search of Models for Hepatic and Placental Pharmacokinetics," [Dissertation] University of Oulu, 2003.
Paludan, et al., "Immune Suppression by Placenta Derived Adherent Cells (PDAC) Correlate with Monocyte Chemoattractant Protein-1 and 1L-2 Secretion." Blood 108: abstract only (2006).
Papaioannou et al., Stem Cells Handbook:19-31 (2004).
Pera et al., *j. Cell. Sci.* (2000) 113:5-10.
Pittenger, M. F., et al. "Multilineage Potential of Adult Human Mesenchymal Stem Cells." *Science* (1999) U.S. vol. 284, No. 5411, pp. 143-147.
Reyes et al, "Purification and Ex Vivo Expansion of Postnatal Human Marrow Mesodermanl Progenitor Cells," *Blood* (2001) 98(9):2615-2625.
Roth, I., et al. "Human Placental Cytotrophoblats Produce the Immunosuppressive Cytokine Interliukin 10," *The Journal of Experimental Medicine* (1996) 184(2): 539-548.
Russo, (2001), The Scientist, 15: 6.
Sakuragawa et al., "Human amniotic epithelial cells are promising transgene carriers for allogeneic cell transplantation into liver," *J. Hum. Genet.* 45:171-176 (2000).
ScienCell—Human Amniotic Epithelial Cells. http://www.sciencellonline.com/products/7100.htm.
Schutz et al., EJCB, Isolation and cultivation of endothelial cells derived from human placenta, (1996) 395-401.
Shamblott, et al., 1998, Derivation of pluripotent stem cells from cultured human primordial germ cells. Proc Natl Acad Sci U S A. 95(23):13726-31.
Shuto et al., (1994) Endocrinology, 134: 1121-126.
Sirchia et al, Placental/umbilical cord blood transplantation Haematologica (1999) 84:738-747.
Wang et al., 2001, "Enhanced recovery of hematopoietic progenitor and stem cells from cultivated, postpartum human placenta," Blood 98(11/1):183a Abstract No. 769.
Webster et al., 2001, Scripta Materialia, 44: 1639-1642.
Ye et al., 2001, "Recovery of placental-derived adherent cells with mesenchymal stem cell characteristics," Blood 98(11/1):147b Abstract No. 4260.
Yen B. Linju et al, "Isolation of multipotent cells from human term placenta" Stem Cells (Dayton, Ohio) 2005, vol. 23, No. 1, Jan. 2005, pp. 3-9, XP002443187 ISSN: 1065-5099.
Zhang Yi et al. "Human placenta-derived mesenchymal progenitor cells support culture expansion of long-term culture-initiating cells from cord blood CD34+ Cell" Experimental Hematology, New, NY, US, vol. 32, No. 7, Jul. 2004, pp. 657-664, XP002389863 ISSN: 0301-472X.
U.S. Appl. No. 12/829,326, filed Jul. 1, 2010, Abbot.
Barlow et al., "Comparison of Human Placenta- and Bone Marrow-Derived Multipotent Mesenchymal Stem Cells," Stem Cells and Development 17:1095-1108 (2008).
Garcia-Olmo et al., "Autologous Stem Cell Transplantation for Treatment of Rectovaginal Fistula in Perianal Crohn's Disease: A New Cell-based Therapy", Int. J. Colorectal Dis. 18:451-454 (2003).
Garcia-Olmo et al., "A Phase I Clinical Trial of the Treatment of Crohn's Fistula by Adipose Mesenchymal Stem Cell Transplantation," Stem Cells in Chron's Fistula 48(7): 1417-1423 (2005).
Sapin, "Esterification of Vitamin A by the Human Placenta Involves Villous Mesenchymal Fibrlboasts," pediatric Research 48(4):565-572 (2000).
Schwab, "Fast and Reliable Culture Method for Cells from 8-10 Week Trophoblast Tissue," Lancet 323:1082 (1984).
Sikkema-Raddatz, "Four Years' Cytogenetic Experience with the Culture of Chorionic Villi," Prenatal Diagnosis 20:950-955 (2000).
Wulf et al., "Mesengenic Progenitor Cells Derived from Human Placenta," Tissue Engineering 10(7/8): 1136-1147 (2004).
Yen, et al, "Isolation of multipotent cells from human term placenta" Stem Cells (Dayton, Ohio) 2005, vol. 23, No. 1, pp. 3-9, XP002443187 ISSN: 1065-5099 (Jan. 2005).
International Search Report and Written Opinion mailed May 28, 2008 in Application No. PCT/US2007/022545.
International Search Report and Written Opinion mailed Sep. 26, 2007 in Application No. PCT/US2006/049491.
Office Action dated Mar. 22, 2007 in U.S. Appl. No. 10/074,976, now US Patent No. 7,311,904.
Notice of Allowance dated Oct. 30, 2008 in U.S. Appl. No. 10/411,655, now US Patent No. 7,498,171.
Office Action dated Feb. 28, 2008 in U.S. Appl. No. 10/411,655, now US Patent No. 7,498,171.
Office Action dated Jul. 11, 2007 in U.S. Appl. No. 10/411,655, now US Patent No. 7,498,171.
Office Action dated May 18, 2006 in U.S. Appl. No. 10/411,655, now US Patent No. 7,498,171.
Office Action dated Nov. 20, 2006 in U.S. Appl. No. 10/411,655, now US Patent No. 7,498,171.
Advisory Action dated Oct. 25, 2007 in U.S. Appl. No. 10/449,248.
Office Action dated Apr. 26, 2007 in U.S. Appl. No. 10/449,248.
Office Action dated Aug. 29, 2006 in U.S. Appl. No. 10/449,248.
Office Action dated Feb. 7, 2008 in U.S. Appl. No. 10/449,248.
Notice of Allowance dated May 21, 2007 in U.S. Appl. No. 10/640,428 now Patent No. 7,255,879.
Office Action dated Jan. 19, 2006 in U.S. Appl. No. 10/640,428, now US Patent No. 7,255,879.
Office Action dated Oct. 18, 2006 in U.S. Appl. No. 10/640,428 now Patent No. 7,255,879.
Office Action dated Apr. 2, 2009 in U.S. Appl. No. 10/721,144.
Final Office Action dated Sep. 14, 2010 in U.S. Appl. No. 10/721,144.
Office Action dated Mar. 18, 2010 in U.S. Appl. No. 10/721,144.
Advisory Action dated Oct. 7, 2009 in U.S. Appl. No. 10/721,144.
Advisory Action dated Aug. 17, 2009 in U.S. Appl. No. 10/721,144.
Notice of Allowance dated Oct. 14, 2008 in U.S. Appl. No. 10/874,828, now US Patent No. 7,468,276.
Notice of Allowance dated Aug. 12, 2009 in U.S. Appl. No. 11/187,400.
Office Action dated Feb. 20, 2009 in U.S. Appl. No. 11/187,400.
Advisory Action dated Sep. 8, 2008 in U.S. Appl. No. 11/187,400.
Office Action dated May 22, 2008 in U.S. Appl. No. 11/187,400.

\* cited by examiner

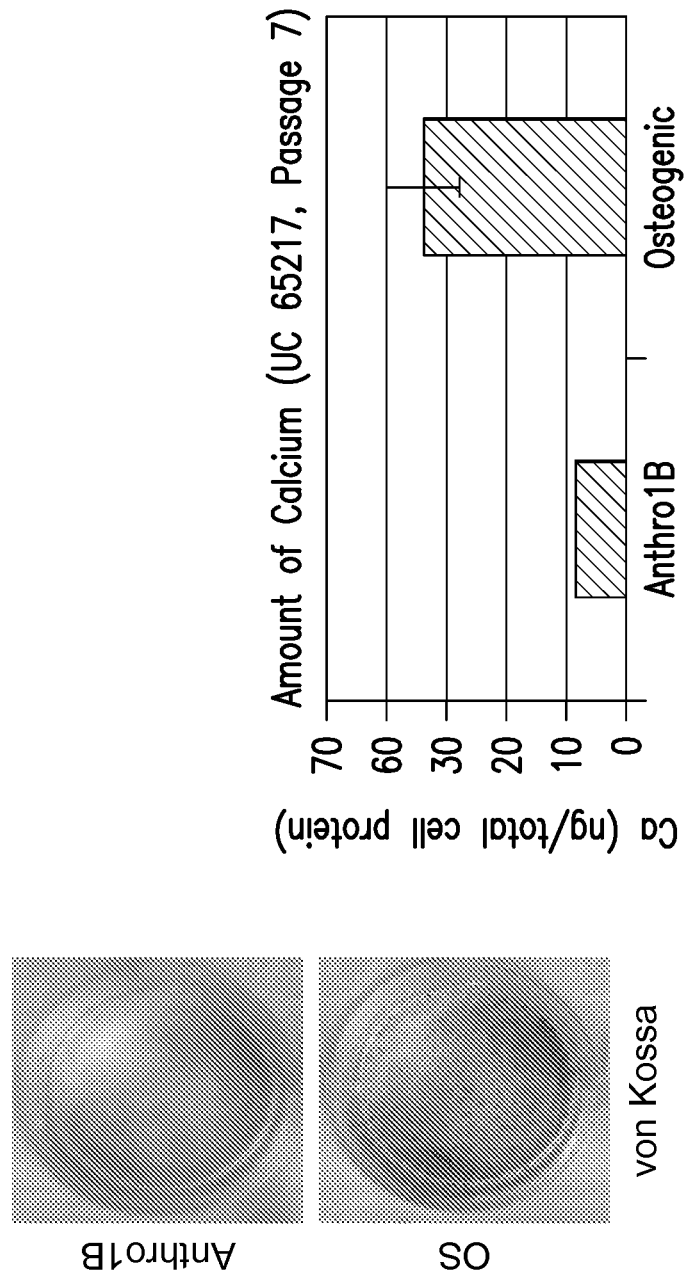

hMSCs hMSCs

HPPs

HPPs

CS061506-1(collagen)_0hrs_20x_phase001.jpg

CS062608-1_2-5hrs_20x_phase002.jpg

US 8,562,972 B2

METHODS AND COMPOSITIONS FOR TREATMENT OF BONE DEFECTS WITH PLACENTAL CELL POPULATIONS

This application claims benefit of U.S. Provisional Application No. 60/853,971, filed Oct. 23, 2006; U.S. Provisional Application No. 60/855,629, filed Oct. 30, 2006; and U.S. Provisional Application No. 60/997,022, filed Sep. 28, 2007.

1. FIELD

Provided herein are isolated placental cells, e.g., placental perfusate, adherent and nonadherent placental stem cells, populations of placental stem cells, compositions comprising the stem cells, methods of obtaining the stem cells, methods of formulating compositions comprising the stem cells, and methods of treating bone defects with the stem cells and compositions.

2. BACKGROUND

Human stem cells are totipotential or pluripotential precursor cells capable of generating a variety of mature human cell lineages. Evidence exists that demonstrates that stem cells can be employed to repopulate many, if not all, tissues and restore physiologic and anatomic functionality.

Many different types of mammalian stem cells have been characterized. See, e.g., Caplan et al., U.S. Pat. No. 5,486,359 (human mesenchymal stem cells); Boyse et al., U.S. Pat. No. 5,004,681 (fetal and neonatal hematopoietic stem and progenitor cells); Boyse et al., U.S. Pat. No. 5,192,553 (same); Beltrami et al., *Cell* 114(6):763-766 (2003) (cardiac stem cells); Forbes et al., *J. Pathol.* 197(4):510-518 (2002) (hepatic stem cells). Umbilical cord blood, and total nucleated cells derived from cord blood, have been used in transplants to restore, partially or fully, hematopoietic function in patients who have undergone ablative therapy.

3. SUMMARY

Provided herein are isolated placental cells, e.g., placental perfusate, adherent or nonadherent placental stem cells, populations of placental stem cells, compositions comprising the cells, methods of obtaining the placental cells, methods of formulating the compositions, and methods of using the cells to treat bone defects.

Provided herein are isolated stem cells, and cell populations comprising such stem cells, wherein the stem cells are present in, and isolatable from placental tissue (e.g., amnion, chorion, placental cotyledons, umbilical cord, etc.), that are useful in the repair of bone defects. The placental stem cells exhibit one or more characteristics of a stem cell (e.g., exhibit markers associated with stem cells, replicate at least 10-20 times in culture in an undifferentiated state, differentiate into adult cells representative of the three germ layers, etc.), and can adhere to a tissue culture substrate (e.g., tissue culture plastic such as the surface of a tissue culture dish or multiwell plate).

In one embodiment, provided herein is an isolated placental stem cell that is nonadherent. In certain embodiments, the isolated stem cell is $CD34^+$. In certain embodiments, the isolated stem cell is $CD44^-$. In certain embodiments, the isolated stem cell is $CD34^+$ and $CD44^-$. In certain embodiments, the isolated stem cell is $CD9^+$, $CD54^+$, $CD90^+$, or $CD166^+$. In certain embodiments, the isolated stem cell is $CD9^+$, $CD54^+$, $CD90^+$, and $CD166^+$. In certain embodiments, the isolated stem cell is $CD31^+$, $CD117^+$, $CD133^+$, or $CD200^+$. In certain embodiments, the isolated stem cell is $CD31^+$, $CD117^+$, $CD133^+$, and $CD200^+$. In certain embodiments, the isolated stem cell has been isolated from a human placenta by enzymatic digestion. In certain embodiments, the isolated stem cell has been isolated from a human placenta by perfusion. In certain embodiments, the isolated stem cell facilitates formation of a mineralized matrix in a population of placental cells when said population is cultured under conditions that allow the formation of a mineralized matrix.

In another embodiment, provided herein is a population of isolated placental cells that are nonadherent. In certain embodiments, the population comprises stem cells that are $CD34^+$. In certain embodiments, the population comprises stem cells that are $CD44^-$. In certain embodiments, the population comprises stem cells that are $CD34^+$ and $CD44^-$. In certain embodiments, the population comprises stem cells that are $CD9^+$, $CD54^+$, $CD90^+$, or $CD166^+$. In certain embodiments, the population comprises stem cells that are $CD9^+$, $CD54^+$, $CD90^+$, and $CD166^+$. In certain embodiments, the population comprises stem cells that are $CD31^+$, $CD117^+$, $CD133^+$, or $CD200^+$. In certain embodiments, the population comprises stem cells that are $CD31^+$, $CD117^+$, $CD133^+$, and $CD200^+$. In certain embodiments, the population comprises stem cells, wherein at least about 70% of said cells are $CD34^+$ and $CD44^-$ stem cells. In certain embodiments, the population comprises stem cells, wherein at least about 90% of said cells are $CD34^+$ and $CD44^-$ stem cells. In certain embodiments, the population has been expanded. In certain embodiments, the population has been passaged at least once. In certain embodiments, the population has been passaged at least five times. In certain embodiments, the population has been passaged at least ten times. In certain embodiments, the population has been passaged at least twenty times. In certain embodiments, the population forms, or facilitates the formation of, a mineralized matrix in a population of placental cells when said population is cultured under conditions that allow the formation of a mineralized matrix.

In another aspect, provided herein is a population of isolated placental stem cells that are $CD34^+$ and $CD44^-$. In certain embodiments, the stem cells are $CD9^+$, $CD54^+$, $CD90^+$, or $CD166^+$. In certain embodiments, the stem cells are $CD9^+$, $CD54^+$, $CD90^+$, and $CD166^+$. In certain embodiments, the stem cells are $CD31^+$, $CD117^+$, $CD133^+$, or $CD200^+$. In certain embodiments, the stem cells are $CD31^+$, $CD117^+$, $CD133^+$, and $CD200^+$. In certain embodiments, at least about 70% of the stem cells are $CD34^+$ and $CD44^-$ stem cells. In certain embodiments, at least about 90% of the stem cells are $CD34^+$ and $CD44^-$ stem cells. In certain embodiments, the population has been expanded. In certain embodiments, the population has been passaged at least once. In certain embodiments, the population has been passaged at least five times. In certain embodiments, the population has been passaged at least ten times. In certain embodiments, the population has been passaged at least twenty times. In certain embodiments, the population forms, or facilitates the formation of, a mineralized matrix in a population of placental cells when said population is cultured under conditions that allow the formation of a mineralized matrix.

In one embodiment, provided herein is an isolated placental stem cell that is $CD200^+$ or $HLA-G^+$. In a specific embodiment, the stem cell is adherent. In another specific embodiment, said cell is $CD200^+$ and $HLA-G^+$. In a specific embodiment, said stem cell is $CD73^+$ and $CD105^+$. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $CD34^-$, $CD38^-$, $CD45^-$, $CD73^+$ and $CD105^+$.

In another specific embodiment, said stem cell facilitates the formation of one or more embryoid-like bodies from a population of isolated placental cells comprising placental stem cells when said population is cultured under conditions that allow formation of embryoid-like bodies.

In another embodiment, provided herein is a population of isolated placental cells comprising $CD200^+$, $HLA-G^+$ stem cells. In a specific embodiment, said stem cells are adherent. In various embodiments, at least about 10%, at least about 20%, at least about 30%, at least about 40%, at least about 50% at least about 60%, at least about 70%, at least about 80%, at least about 90%, or at least about 95% or more of said isolated placental cells are $CD200^+$, $HLA-G^+$ stem cells. In a specific embodiment of the above populations, said stem cells are $CD73^+$ and $CD105^+$. In another specific embodiment, said stem cells are $CD34^-$, $CD38^-$ or $CD45^-$. In a more specific embodiment, said stem cells are $CD34^-$, $CD38^-$, $CD45^-$, $CD73^+$ and $CD105^+$. In other specific embodiments, said population has been expanded, e.g., passaged at least once, at least three times, at least five times, at least 10 times, at least 15 times, or at least 20 times. In another specific embodiment, said population forms one or more embryoid-like bodies when cultured under conditions that allow formation of embryoid-like bodies.

In another embodiment, provided herein is an isolated placental stem cell that is $CD73^+$, $CD105^+$, and $CD200^+$. In a specific embodiment, said stem cell is adherent. In another specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, $CD45^-$, and $HLA-G^+$. In another specific embodiment, said stem cell facilitates development of one or more embryoid-like bodies from a population of isolated placental cells comprising the stem cell when said population is cultured under conditions that allow formation of embryoid-like bodies.

In another embodiment, provided herein is a population of isolated placental cells comprising $CD73^+$, $CD105^+$, $CD200^+$ stem cells. In a specific embodiment, said stem cells are adherent. In various embodiments, at least about 10%, at least about 20%, at least about 30%, at least about 40%, at least about 50% at least about 60%, at least about 70%, at least about 80%, at least about 90%, or at least about 95% of said isolated placental cells are $CD73^+$, $CD105^+$, $CD200^+$ stem cells. In a specific embodiment of said populations, said stem cells are $HLA-G^+$. In another specific embodiment, said stem cells are $CD34^-$, $CD38^-$ or $CD45^-$. In another specific embodiment, said stem cells are $CD34^-$, $CD38^-$ and $CD45^-$. In a more specific embodiment, said stem cells are $CD34^-$, $CD38^-$, $CD45^-$, and $HLA-G^+$. In other specific embodiments, said population has been expanded, for example, passaged at least once, at least three times, at least five times, at least 10 times, at least 15 times, or at least 20 times. In another specific embodiment, said population forms one or more embryoid-like bodies in culture under conditions that allow formation of embryoid-like bodies.

Also provided herein is an isolated placental stem cell that is $CD200^+$ and $OCT-4^+$. In a specific embodiment, said stem cell is adherent. In another specific embodiment, the stem cell is $CD73^+$ and $CD105^+$. In another specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, $CD45^-$, $CD73^+$, $CD105^+$ and $HLA-G^+$. In another specific embodiment, said stem cell facilitates the formation of one or more embryoid-like bodies from a population of isolated placental cells comprising placental stem cells when said population is cultured under conditions that allow formation of embryoid-like bodies.

In another embodiment, provided herein is a population of isolated placental cells comprising $CD200^+$, $OCT-4^+$ placental stem cells. In a specific embodiment, the stem cells are adherent. In various embodiments, at least about 10%, at least about 20%, at least about 30%, at least about 40%, at least about 50%, at least about 60%, at least about 70%, at least about 80%, at least about 90%, or at least about 95% of said isolated placental cells are $CD200^+$, $OCT-4^+$ stem cells. In a specific embodiment of the above populations, said stem cells are $CD73^+$ and $CD105^+$. In another specific embodiment, said stem cells are $HLA-G^+$. In another specific embodiment, said stem cells are $CD34^-$, $CD38^-$ and $CD45^-$. In a more specific embodiment, said stem cells are $CD34^-$, $CD38^-$, $CD45^-$, $CD73^+$, $CD105^+$ and $HLA-G^+$. In other specific embodiments, said population has been expanded, for example, has been passaged at least once, at least three times, at least five times, at least 10 times, at least 15 times, or at least 20 times. In another specific embodiment, said population forms one or more embryoid-like bodies when cultured under conditions that allow the formation of embryoid-like bodies.

In another embodiment, provided herein is an isolated placental stem cell that is $CD73^+$ and $CD105^+$ and which facilitates the formation of one or more embryoid-like bodies in a population of isolated placental cells comprising said stem cell when said population is cultured under conditions that allow formation of embryoid-like bodies. In a specific embodiment, said stem cell is adherent. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $OCT4^+$. In a more specific embodiment, said stem cell is $OCT4+$, $CD34^-$, $CD38^-$ and $CD45^-$.

Further provided herein is a population of isolated placental cells comprising $CD73^+$, $CD105^+$ placental stem cells, wherein said population forms one or more embryoid-like bodies under conditions that allow formation of embryoid-like bodies. In a specific embodiment, said stem cells are adherent. In various embodiments, at least about 10%, at least about 20%, at least about 30%, at least about 40%, at least about 50% at least about 60%, at least about 70%, at least about 80%, at least about 90%, or at least about 95% of said isolated placental cells are $CD73^+$, $CD105^+$ stem cells. In a specific embodiment of the above populations, said stem cells are $CD34^-$, $CD38^-$ or $CD45^-$. In another specific embodiment, said stem cells are $CD34^-$, $CD38^-$ and $CD45^-$. In another specific embodiment, said stem cells are $OCT-4^+$. In a more specific embodiment, said stem cells are $OCT-4^+$, $CD34^-$, $CD38^-$ and $CD45^-$. In other specific embodiments, said population has been expanded, for example, has been passaged at least once, at least three times, at least five times, at least 10 times, at least 15 times, or at least 20 times.

Further provided herein is an isolated placental stem cell that is $CD73^+$, $CD105^+$ and $HLA-G^+$. In a specific embodiment, said stem cell is adherent. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $OCT-4^+$. In another specific embodiment, said stem cell is $CD200^+$. In a more specific embodiment, said stem cell is $CD34^-$, $CD38^-$, $CD45^-$, $OCT-4^+$ and $CD200^+$. In another specific embodiment, said stem cell facilitates the formation of one or more embryoid-like bodies from a population of isolated placental cells comprising placental stem cells in culture under conditions that allow formation of embryoid-like bodies.

Further provided herein is a population of isolated placental cells comprising CD73+, CD105+ and HLA-G+ placental stem cells. In a specific embodiment, the stem cells are adherent. In various embodiments, at least about 10%, at least about 20%, at least about 30%, at least about 40%, at least about 50% at least about 60%, at least about 70%, at least about 80%, at least about 90%, or at least about 95% of said isolated placental cells are CD73+, CD105+ and HLA-G+ stem cells. In a specific embodiment of the above populations, said stem cells are CD34−, CD38− or CD45−. In another specific embodiment, said stem cells are CD34−, CD38− and CD45−. In another specific embodiment, said stem cells are OCT-4+. In another specific embodiment, said stem cells are CD200+. In a more specific embodiment, said stem cells are CD34−, CD38−, CD45−, OCT-4+ and CD200+. In another specific embodiment, said population has been expanded, for example, has been passaged at least once, at least three times, at least five times, at least 10 times, at least 15 times, or at least 20 times. In another specific embodiment, said population forms embryoid-like bodies when cultured under conditions that allow the formation of embryoid-like bodies.

Further provided herein is an isolated placental stem cell that is OCT-4+ and which facilitates formation of one or more embryoid-like bodies in a population of isolated placental cells comprising said stem cell when cultured under conditions that allow formation of embryoid-like bodies. In a specific embodiment, said stem cell is adherent. In another specific embodiment, said stem cell is CD73+ and CD105+. In another specific embodiment, said stem cell is CD34−, CD38−, or CD45−. In another specific embodiment, said stem cell is CD200+. In a more specific embodiment, said stem cell is CD73+, CD105+, CD200+, CD34−, CD38−, and CD45−.

Also provided herein is a population of isolated placental cells comprising OCT-4+ placental stem cells, wherein said population forms one or more embryoid-like bodies when cultured under conditions that allow the formation of embryoid-like bodies. In a specific embodiment, the stem cells are adherent. In various embodiments, at least about 10%, at least about 20%, at least about 30%, at least about 40%, at least about 50% at least about 60%, at least about 70%, at least about 80%, at least about 90%, or at least about 95% of said isolated placental cells are OCT4+ stem cells. In a specific embodiment of the above populations, said stem cells are CD73+ and CD105+. In another specific embodiment, said stem cells are CD34−, CD38−, or CD45−. In another specific embodiment, said stem cells are CD200+. In a more specific embodiment, said stem cells are CD73+, CD105+, CD200+, CD34−, CD38−, and CD45−. In another specific embodiment, said population has been expanded, for example, passaged at least once, at least three times, at least five times, at least 10 times, at least 15 times, or at least 20 times.

Further provided herein is an isolated population of the adherent or nonadherent placental stem cells described herein that is produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises placental stem cells; and isolating a plurality of said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

Further provided herein is an isolated placental stem cell, or isolated population of the placental stem cells, described herein that is produced according to a method comprising digesting placental tissue with a tissue-disrupting enzyme to obtain a population of placental cells comprising placental stem cells, and isolating a plurality of placental stem cells from the remainder of said placental cells. In specific embodiments, said placental tissue is a whole placenta, an amniotic membrane, chorion, a combination of amnion and chorion, or a combination of any of the foregoing. In other specific embodiment, the tissue-disrupting enzyme is trypsin or collagenase.

In more specific embodiments, provided herein is an isolated placental stem cell, wherein said stem cell expresses one or more genes at a detectably higher level than a bone marrow-derived mesenchymal stem cell, wherein said one or more genes are ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and/or ZC3H12A, and wherein said bone marrow derived stem cell has undergone a number of passages in culture equivalent to a number of passages for said placental stem cell. In a more specific embodiment, said placental stem cell expresses ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and ZC3H12A at a detectably higher level than a bone marrow-derived mesenchymal stem cell.

In more specific embodiments, also provided herein is a population of isolated placental stem cells, wherein said population of stem cells express one or more genes at a detectably higher level than a population of bone marrow-derived mesenchymal stem cells, wherein said one or more genes are ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and/or ZC3H12A, and wherein said population of bone marrow derived stem cells has undergone a number of passages in culture equivalent to a number of passages for said placental stem cell, and wherein said population of bone marrow-derived mesenchymal stem cells has a number of cells equivalent to said population of isolated stem cells. In a more specific embodiment, the population of isolated stem cells expresses ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and ZC3H12A at a detectably higher level than said population of isolated bone marrow-derived mesenchymal stem cells.

Also provided herein are compositions that comprise one or more of the placental cells, e.g., placental perfusate, placental perfusate cells or placental stem cells, provided herein, wherein the cells have been isolated from the placenta. In preferred embodiments, the compositions comprising placental cells are useful for the repair of bone defects. Thus, provided herein is a composition comprising placental perfusate, or cells isolated from placental perfusate, e.g., total nucleated cells from placental perfusate.

In one aspect, provided herein is a composition comprising placental perfusate or placental perfusate cells, e.g., total nucleated cells from placental perfusate.

Further provided herein is a composition comprising a placental stem cell, wherein said stem cell is an isolated placental stem cell that is nonadherent. In certain embodiments, the stem cell is CD34$^+$. In certain embodiments, the stem cell is CD44$^-$. In certain embodiments, the stem cell is CD34$^+$ and CD44$^-$. In certain embodiments, the stem cell is CD9$^+$, CD54$^+$, CD90$^+$, or CD166$^+$. In certain embodiments, the stem cell is CD9$^+$, CD54$^+$, CD90$^+$, and CD166$^+$. In certain embodiments, the stem cell is CD31$^+$, CD117$^+$, CD133$^+$, or CD200$^+$. In certain embodiments, the stem cell is CD31$^+$, CD117$^+$, CD133$^+$, and CD200$^+$. In certain embodiments, the stem cell has been isolated from a human placenta by enzymatic digestion. In certain embodiments, the stem cell has been isolated from a human placenta by perfusion. In certain embodiments, the cell facilitates formation of a mineralized matrix in a population of placental cells when said population is cultured under conditions that allow the formation of a mineralized matrix.

In another aspect, provided herein is a composition comprising a placental stem cell, wherein said stem cell is an isolated stem cell that is CD34$^+$ and CD44$^-$. In certain embodiments, the stem cell is CD9$^+$, CD54$^+$, CD90$^+$, or CD166$^+$. In certain embodiments, the stem cell is CD9$^+$, CD54$^+$, CD90$^+$, and CD166$^+$. In certain embodiments, the stem cell is CD31$^+$, CD117$^+$, CD133$^+$, or CD200$^+$. In certain embodiments, the stem cell is CD31$^+$, CD117$^+$, CD133$^+$, and CD200$^+$. In certain embodiments, the stem cell has been isolated from a human placenta by enzymatic digestion. In certain embodiments, the stem cell has been isolated from a human placenta by perfusion. In certain embodiments, the cell facilitates formation of a mineralized matrix in a population of placental cells when said population is cultured under conditions that allow the formation of a mineralized matrix.

In certain embodiments, the composition comprises an isolated stem cell provided herein and a compound that induces the differentiation of said stem cell into an osteogenic cell. In certain embodiments, the composition comprises an isolated stem cell, or a population of isolated stem cells, provided herein, and a compound that induces the differentiation of a plurality of stem cells in said population of stem cells into osteogenic cells. In certain embodiments, the compound is dexamethasone or ascorbic acid.

In certain embodiments, provided herein is a composition comprising an isolated placental stem cell, wherein said stem cell is CD200$^+$ and HLA-G$^+$. In a specific embodiment, the stem cell is adherent. In another specific embodiment, said stem cell is CD73$^+$ and CD105$^+$. In another specific embodiment, said stem cell is CD34$^-$, CD38$^-$ or CD45$^-$. In another specific embodiment, said stem cell is CD34$^-$, CD38$^-$ and CD45$^-$. In a more specific embodiment, said stem cell is CD34$^-$, CD38$^-$, CD45$^-$, CD73$^+$, CD105$^+$, CD200$^+$ and HLA-G$^+$.

In another embodiment, provided herein is a composition comprising an isolated placental stem cell, wherein said stem cell is CD73$^+$, CD105$^+$ and CD200$^+$. In a specific embodiment, the stem cell is adherent. In another specific embodiment, said stem cell is HLA-G$^+$. In another specific embodiment, said stem cell is CD34$^-$, CD38$^-$ or CD45$^-$. In another specific embodiment, said stem cell is CD34$^-$, CD38$^-$ and CD45$^-$. In another specific embodiment, said stem cell is CD34$^-$, CD38$^-$, CD45$^-$, and HLA-G$^+$.

In another embodiment, provided herein is a composition comprising an isolated placental stem cell, wherein said stem cell is CD200$^+$ and OCT-4$^+$. In a specific embodiment, the stem cell is adherent. In another specific embodiment, said stem cell is CD73$^+$ and CD105$^+$. In another specific embodiment, said stem cell is HLA-G$^+$. In another specific embodiment, said stem cell is CD34$^-$, CD38$^-$ or CD45$^-$. In another specific embodiment, said stem cell is CD34$^-$, CD38$^-$ and CD45$^-$. In another specific embodiment, said stem cell is CD34$^-$, CD38$^-$, CD45$^-$, CD73$^+$, CD105$^+$, and HLA-G$^+$.

In another embodiment, provided herein is a composition comprising an isolated placental stem cell that is CD73$^+$ and CD105$^+$, wherein said stem cell facilitates formation of an embryoid-like body in a population of isolated placental cells comprising said stem cell under conditions that allow the formation of an embryoid-like body. In a specific embodiment, the stem cell is adherent. In another specific embodiment, said stem cell is CD34$^-$, CD38$^-$ or CD45$^-$. In another specific embodiment, said stem cell is OCT-4$^+$. In another specific embodiment, said stem cell is CD200$^+$. In another specific embodiment, said stem cell is OCT-4 +, CD200$^+$, CD34$^-$, CD38$^-$ and CD45$^-$.

In yet another embodiment, provided herein is a composition comprising an isolated placental stem cell that is CD73$^+$, CD105$^+$ and HLA-G$^+$. In a specific embodiment, the stem cell is adherent. In another specific embodiment, said stem cell is CD34$^-$, CD38$^-$ or CD45$^-$. In another specific embodiment, said stem cell is OCT-4$^+$. In another specific embodiment, said stem cell is CD200$^+$. In another specific embodiment, said stem cell is OCT-4$^+$, CD200$^+$, CD34$^-$, CD38$^-$ and CD45$^-$.

In another embodiment, provided herein is a composition comprising an isolated placental stem cell that is OCT-4$^+$, wherein said stem cell facilitates formation of an embryoid-like body in a population of isolated placental cells comprising said stem cell under conditions that allow the formation of an embryoid-like body. In a specific embodiment, said stem cell is CD73$^+$ and CD105$^+$. In another specific embodiment, said stem cell is CD34$^-$, CD38$^-$ and CD45$^-$. In another specific embodiment, said stem cell is CD200$^+$. In another specific embodiment, said stem cell is CD73$^+$, CD105$^+$, CD200$^+$, CD34$^-$, CD38$^-$ and CD45$^-$.

Further provided herein is a composition comprising a placental stem cells that expresses one or more genes at a detectably higher level than a bone marrow-derived mesenchymal stem cell, wherein said one or more genes are selected from the group consisting of ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and ZC3H12A, and wherein said bone marrow derived stem cell has undergone a number of passages in culture equivalent to a number of passages for said placental stem cell. In a more specific embodiment of the above composition, said stem cells express ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and ZC3H12A at a detectably higher level than a population of isolated bone marrow-derived mesenchymal stem cell, wherein said population of stem cells and said population of bone marrow-derived mesenchymal cells have equivalent numbers of cells.

In another specific embodiment, any of the foregoing compositions comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons. In certain embodiments, the matrix is a synthetic degradable polymer such as, for example, polylactic acid or polyglycolic acid. In certain embodiments, the matrix is an implantable scaffolding substrate. In certain embodiments, the implantable scaffolding substrate is selected from the group consisting of a β-tricalcium phosphate substrate, a β-tricalcium phosphate-collagen substrate, a collagen substrate, a calcium phosphate substrate, a mineralized human placental collagen substrate, a hyaluronic acid substrate, and a ceramic substrate. In certain embodiments, the implantable scaffolding substrate is a β-tricalcium phosphate substrate. In certain embodiments, the implantable scaffolding substrate is a β-tricalcium phosphate-collagen substrate. In certain embodiments, the implantable scaffolding substrate is a collagen substrate. In certain embodiments, the implantable scaffolding substrate is a calcium phosphate substrate. In certain embodiments, the implantable scaffolding substrate is a mineralized human placental collagen substrate.

In another embodiment, further provided herein is a composition comprising medium conditioned by any of the foregoing stem cells, or any of the foregoing stem cell populations. In a specific embodiment, any such composition comprises a stem cell that is not derived from a placenta. In a more specific embodiment, said stem cell is an embryonic stem cell. In another more specific embodiment, said stem cell is a mesenchymal stem cell. In another more specific embodiment, said stem cell is a bone marrow-derived stem cell. In another more specific embodiment, said stem cell is a hematopoietic progenitor cell. In another more specific embodiment, said stem cell is a somatic stem cell. In an even more specific embodiment, said somatic stem cell is a neural stem cell, a hepatic stem cell, a pancreatic stem cell, an endothelial stem cell, a cardiac stem cell, or a muscle stem cell.

In another aspect, provided herein is a composition comprising medium conditioned by a placental stem cell or population of placental stem cells provided herein. In certain embodiments, the composition comprises medium conditioned by a cell population, e.g., a stem cell population, provided herein.

Also provided herein is a method of producing a cell population comprising selecting cells that do not adhere to a substrate, and isolating said cells from other cells to form a cell population. In certain embodiments, the method further comprises selecting cells that express CD34 and do not express CD44 and increasing the concentration of, e.g., isolating said cells from other cells, to form a cell population.

In certain embodiments, provided herein is a method of producing a cell population, comprising selecting cells that (a) do not adhere to a substrate, (b) express CD34 and do not express CD44, and (c) facilitate the formation of mineralized matrix in a population of placental cells when said population is cultured under conditions that allow for the formation of a mineralized matrix; and isolating said cells from other cells to form a cell population. In certain embodiments, the substrate comprises fibronectin.

In certain embodiments, the method further comprises selecting cells that express CD9, CD29, CD54, CD90, CD166, or a combination of the foregoing.

In certain embodiments, the method further comprises selecting cells that express CD31, CD34, CD117, CD133, CD200, or a combination of the foregoing.

In certain embodiments, the selecting is accomplished using an antibody. In certain embodiments, the selecting is accomplished using flow cytometry. In certain embodiments, the selecting is accomplished using magnetic beads. In certain embodiments, the selecting is accomplished by fluorescence-activated cell sorting. In certain embodiments, the cell population is expanded.

In another aspect, provided herein is a population of non-adherent placental stem cells, wherein said cells have been cryopreserved, and wherein said population is contained within a container. In certain embodiments, the stem cells are $CD34^+$ and $CD44^-$. In certain embodiments, the cells have been cryopreserved, and wherein said population is contained within a container, and wherein said stem cells form a mineralized matrix when cultured under conditions allowing the formation of a mineralized matrix. In certain embodiments, the container is a bag suitable for the intravenous delivery of a liquid. In certain embodiments, the population comprises $1 \times 10^6$ said stem cells. In certain embodiments, the population comprises $5 \times 10^6$ said stem cells. In certain embodiments, the population comprises $1 \times 10^7$ said stem cells. In certain embodiments, the population comprises $5 \times 10^7$ said stem cells. In certain embodiments, the population comprises $1 \times 10^8$ said stem cells. In certain embodiments, the population comprises $5 \times 10^8$ said stem cells. In certain embodiments, the population comprises $1 \times 10^9$ said stem cells. In certain embodiments, the population comprises $5 \times 10^9$ said stem cells. In certain embodiments, the population comprises $1 \times 10^{10}$ said stem cells. In certain embodiments, the stem cells have been passaged no more than 5 times. In certain embodiments, the stem cells have been passaged no more than 10 times. In certain embodiments, the stem cells have been passaged no more than 15 times. In certain embodiments, the stem cells have been passaged no more than 20 times. In certain embodiments, the stem cells have been expanded within said container. In certain embodiments, the population is contained in a 0.9% NaCl solution.

In another aspect, provided herein is a method of producing osteogenic cells with the ability to mineralize matrix, comprising culturing a plurality of stem cells provided herein or a population of isolated stem cells provided herein, under conditions in which said stem cells differentiate into osteogenic cells, said culturing being for a time sufficient for said osteogenic cells to produce, or facilitate the production of, detectable amounts of mineralized matrix rich in calcium and/or phosphate. In certain embodiments, the osteogenic cells produce bone.

In still another aspect, provided herein is a method for formulating a matrix, comprising combining a population of stem cells provided herein with an implantable scaffolding substrate. In certain embodiments, the stem cells are nonadherent. In certain embodiments, the stem cells are $CD34^+$. In certain embodiments, the stem cells are $CD44^-$. In certain embodiments, the stem cells are $CD34^+$ and $CD44^-$. In certain embodiments, the stem cells are $CD9^+$, $CD54^+$, $CD90^+$, or $CD166^+$. In certain embodiments, the stem cells are $CD9^+$, $CD54^+$, $CD90^+$, and $CD166^+$. In certain embodiments, the stem cells are $CD31^+$, $CD117^+$, $CD133^+$, or $CD200^+$. In certain embodiments, the stem cells are $CD31^+$, $CD117^+$, $CD133^+$, and $CD200^+$. In certain embodiments, at least about 70% of the stem cells are $CD34^+$ and $CD44^-$ stem cells. In certain embodiments, at least about 90% of the stem cells are $CD34^+$ and $CD44^-$ stem cells. In certain embodiments, the population comprises $1\times10^6$ said stem cells. In certain embodiments, the population comprises $5\times10^6$ said stem cells. In certain embodiments, the population comprises $1\times10^7$ said stem cells. In certain embodiments, the population comprises $5\times10^7$ said stem cells. In certain embodiments, the population comprises $1\times10^8$ said stem cells. In certain embodiments, the population comprises $5\times10^8$ said stem cells. In certain embodiments, the population comprises $1\times10^9$ said stem cells. In certain embodiments, the population comprises $5\times10^9$ said stem cells. In certain embodiments, the population comprises $1\times10^{10}$ said stem cells. In certain embodiments, the stem cells have been passaged at least, about, or no more than 5 times. In certain embodiments, the stem cells have been passaged at least, about, or no more than 10 times. In certain embodiments, the stem cells have been passaged at least, about, or no more than 15 times. In certain embodiments, the stem cells have been passaged at least, about, or no more than 20 times. In certain embodiments, the population has been expanded.

In certain embodiments, the implantable scaffolding substrate is selected from the group consisting of a β-tricalcium phosphate substrate, a β-tricalcium phosphate-collagen substrate, a collagen substrate, a calcium phosphate substrate, a mineralized human placental collagen substrate, a hyaluronic acid substrate, and a ceramic substrate. In certain embodiments, the implantable scaffolding substrate is a β-tricalcium phosphate substrate. In certain embodiments, the implantable scaffolding substrate is a β-tricalcium phosphate-collagen substrate. In certain embodiments, the implantable scaffolding substrate is a collagen substrate. In certain embodiments, the implantable scaffolding substrate is a calcium phosphate substrate. In certain embodiments, the implantable scaffolding substrate is a mineralized human placental collagen substrate.

In another aspect, provided herein is a method for formulating an injectable composition, comprising combining a population of placental stem cells with injectable hyaluronic acid or collagen. In certain embodiments, the stem cells are nonadherent. In certain embodiments, the stem cells are $CD34^+$. In certain embodiments, the stem cells are $CD44^-$. In certain embodiments, the said stem cells are $CD34^+$ and $CD44^-$. In certain embodiments, the said stem cells are $CD9^+$, $CD54^+$, $CD90^+$, or $CD166^+$. In certain embodiments, the said stem cells are $CD9^+$, $CD54^+$, $CD90^+$, and $CD166^+$. In certain embodiments, the said stem cells are $CD31^+$, $CD117^+$, $CD133^+$, or $CD200^+$. In certain embodiments, the said stem cells are $CD31^+$, $CD117^+$, $CD133^+$, and $CD200^+$. In certain embodiments, at least about 70% of said cells are $CD34^+$ and $CD44^-$ stem cells. In certain embodiments, the at least about 90% of said cells are $CD34^+$ and $CD44^-$ stem cells. In certain other embodiments, the placental stem cells are adherent. In specific embodiments, the placental stem cells are $CD200^+$ and $HLA-G^+$; $CD73^+$, $CD105^+$, and $CD200^+$; $CD200^+$ and $OCT-4^+$; $CD73^+$, $CD105^+$ and $HLA-G^+$; $CD73^+$ and $CD105^+$ and facilitates the formation of one or more embryoid-like bodies in a population of placental cells comprising said stem cell when said population is cultured under conditions that allow the formation of an embryoid-like body; or $OCT-4^+$ and facilitates the formation of one or more embryoid-like bodies in a population of placental cells comprising the stem cell when said population is cultured under conditions that allow formation of embryoid-like bodies; or any combination thereof. In more specific embodiments of the nonadherent placental stem cells, the isolated $CD200^+$, $HLA-G^+$ stem cell is $CD34^-$, $CD38^-$, $CD45^-$, $CD73^+$ and $CD105^+$; the isolated $CD73^+$, $CD105^+$, and $CD200^+$ stem cell is $CD34^-$, $CD38^-$, $CD45^-$, and $HLA-G^+$; the isolated $CD200^+$, $OCT-4^+$ stem cell is $CD34^-$, $CD38^-$, $CD45^-$, $CD73^+$, $CD105^+$ and $HLA-G^+$; the isolated stem cell of claim 1, wherein said $CD73^+$, $CD105^+$ and $HLA-G^+$ stem cell is $CD34^-$, $CD45^-$, $OCT-4^+$ and $CD200^+$; the isolated $CD73^+$ and $CD105^+$ stem cell that facilitates the formation of one or more embryoid-like bodies is $OCT4^+$, $CD34^-$, $CD38^-$ and $CD45^-$; and/or the isolated $OCT-4^+$ and which facilitates the formation of one or more embryoid-like bodies is $CD73^+$, $CD105^+$, $CD200^+$, $CD34^-$, $CD38^-$ and $CD45^-$. In certain embodiments, the population of placental stem cells has been expanded. In certain embodiments, the said composition comprises injectable hyaluronic acid. In certain embodiments, the composition comprises injectable collagen. Provided herein are also compositions comprising a population of nonadherent stem cells and injectable hyaluronic acid or collagen.

In another aspect, provided herein is a method for treating bone defects in a subject, comprising administering to a subject in need thereof an implantable or injectable composition comprising a population of stem cells provided herein, thereby treating the bone defect in the subject. In certain embodiments, the bone defect is an osteolytic lesion associated with a cancer, a bone fracture, or a spine, e.g., in need of fusion. In certain embodiments, the osteolytic lesion is associated with multiple myeloma, bone cancer, or metastatic cancer. In certain embodiments, the bone fracture is a non-union fracture. In certain embodiments, an implantable composition comprising a population of nonadherent stem cells is administered to the subject. In certain embodiments, an implantable composition is surgically implanted, e.g., at the site of the bone defect. In certain embodiments, an injectable composition comprising a population of nonadherent stem cells is administered to the subject. In certain embodiments, an injectable composition is surgically administered to the region of the bone defect. In certain embodiments, the injectable composition is systemically administered.

In certain embodiments, the stem cells are nonadherent. In certain embodiments, the stem cells are $CD34^+$. In certain embodiments, the stem cells are $CD44^-$. In certain embodiments, the stem cells are $CD34^+$ and $CD44^-$. In certain embodiments, the stem cells are $CD9^+$, $CD54^+$, $CD90^+$, or $CD166^+$. In certain embodiments, the stem cells are $CD9^+$, $CD54^+$, $CD90^+$, and $CD166^+$. In certain embodiments, the stem cells are $CD31^+$, $CD117^+$, $CD133^+$, or $CD200^+$. In certain embodiments, the stem cells are $CD31^+$, $CD117^+$, $CD133^+$, and $CD200^+$. In certain embodiments, at least about 70% of the cells are $CD34^+$ and $CD44^-$ stem cells. In certain embodiments, at least about 90% of the cells are $CD34^+$ and $CD44^-$ stem cells. In certain other embodiments, the placental stem cells are adherent. In specific embodiments, the placental stem cells are CD200+ and HLA-G+; CD73+, CD105+, and CD200+; CD200+ and OCT-4+; CD73+, CD105+ and HLA-G+; CD73+ and CD105+ and facilitates the formation of one or more embryoid-like bodies in a population of placental cells comprising said stem cell when said population is cultured under conditions that allow the formation of an embryoid-like body; or OCT-4+ and facilitates the formation of one or more embryoid-like bodies in a population of placental cells comprising the stem cell when said population is cultured under conditions that allow formation of embryoid-like bodies; or any combination thereof. In more specific embodiments of the nonadherent placental stem cells, the isolated CD200+, HLA-G+ stem cell is CD34−, CD38−, CD45−, CD73+ and CD105+; the isolated CD73+, CD105+, and CD200+ stem cell is CD34−, CD38−, CD45−, and HLA-G+; the isolated CD200+, OCT-4+ stem cell is CD34−, CD38−, CD45−, CD73+, CD105+ and HLA-G+; the isolated stem cell of claim 1, wherein said CD73+, CD105+ and HLA-G+ stem cell is CD34−, CD45−, OCT-4+ and CD200+; the isolated CD73+ and CD105+ stem cell that facilitates the formation of one or more embryoid-like bodies is OCT4+, CD34−, CD38− and CD45−; and/or the isolated OCT-4+ and which facilitates the formation of one or more embryoid-like bodies is CD73+, CD105+, CD200+, CD34−, CD38−, and CD45−. In certain embodiments, the population has been expanded.

In yet another aspect, provided herein is a method of producing a cell population comprising selecting cells that a) adhere to a substrate, and b) express CD34 and do not express CD44, and isolating said cells from other cells to form a cell population. In certain embodiments, the method further comprises isolating said cells from other cells to form a cell population. In certain embodiments, the method of producing a cell population, comprises selecting cells that (a) adhere to a substrate, (b) express CD34 and do not express CD44, and (c) facilitate the formation of mineralized matrix in a population of placental cells when said population is cultured under conditions that allow for the formation of a mineralized matrix; and isolating said cells from other cells to form a cell population. In certain embodiments, the said substrate comprises fibronectin. In certain embodiments, provided herein is a method of producing a cell population comprising selecting cells that a) do not adhere to a substrate, and b) express CD34 and do not express CD44, and isolating said cells from other cells to form a cell population. In certain embodiments, the method further comprises isolating said cells from other cells to form a cell population. In certain embodiments, the method of producing a cell population, comprises selecting cells that (a) do not adhere to a substrate, (b) express CD34 and do not express CD44, and (c) facilitate the formation of mineralized matrix in a population of placental cells when said population is cultured under conditions that allow for the formation of a mineralized matrix; and isolating said cells from other cells to form a cell population. In certain embodiments, the said substrate comprises fibronectin. In certain embodiments, the method comprises selecting cells that express at least one of the following: CD9, CD29, CD54, CD90, CD166, or a combination of the foregoing. In certain embodiments, the method comprises selecting cells that express at least one of the following: CD31, CD34, CD117, CD133, CD200, or a combination of the foregoing.

In certain embodiments, the selecting is accomplished using an antibody. In certain embodiments, the selecting is accomplished using flow cytometry. In certain embodiments, the selecting is accomplished using magnetic beads. In certain embodiments, the selecting is accomplished by fluorescence-activated cell sorting. In certain embodiments, the cell population is expanded.

In certain embodiments, the stem cells are CD34+ and CD44−, wherein the cells have been cryopreserved, and wherein the population is contained within a container. In certain embodiments, the cells have been cryopreserved, and wherein said population is contained within a container, and wherein said stem cells form a mineralized matrix when cultured under conditions allowing the formation of a mineralized matrix.

In certain embodiments, the container is a bag suitable for the intravenous delivery of a liquid. In certain embodiments, the population comprises $1\times10^6$ said stem cells. In certain embodiments, the population comprises $5\times10^6$ said stem cells. In certain embodiments, the population comprises $1\times10^7$ said stem cells. In certain embodiments, the population comprises $5\times10^7$ said stem cells. In certain embodiments, the population comprises $1\times10^8$ said stem cells. In certain embodiments, the population comprises $5\times10^8$ said stem cells. In certain embodiments, the population comprises $1\times10^9$ said stem cells. In certain embodiments, the comprises $5\times10^9$ said stem cells. In certain embodiments, the population comprises $1\times10^{10}$ said stem cells. In certain embodiments, the stem cells have been passaged no more than 5 times. In certain embodiments, the stem cells have been passaged no more than 10 times. In certain embodiments, the stem cells have been passaged no more than 15 times. In certain embodiments, the stem cells have been passaged no more than 20 times. In certain embodiments, the stem cells have been expanded within said container. In certain embodiments, the said population is contained in a 0.9% NaCl solution.

In another aspect, provided herein is a method of producing osteogenic cells comprising culturing a plurality of placental stem cells or a population of isolated placental stem cells, under conditions in which said stem cells differentiate into osteogenic cells, said culturing being for a time sufficient for said osteogenic cells to produce, or facilitate the production of, detectable amounts of mineralized calcium.

In another aspect, provided herein is a method for formulating an matrix, comprising combining a population of placental stem cells with an implantable scaffolding substrate, wherein said stem cells are CD34+ and CD44−. In certain embodiments, the stem cells are CD9+, CD54+, CD90+, or CD166+. In certain embodiments, the stem cells are CD9+, CD54+, CD90+, and CD166+. In certain embodiments, the stem cells are CD31+, CD117+, CD133+, or CD200+. In certain embodiments, the stem cells are CD31+, CD117+, CD133+, and CD200+. In certain embodiments, at least about 70% of said cells are CD34+ and CD44− stem cells. In certain embodiments, at least about 90% of said cells are CD34+ and CD44− stem cells. In certain embodiments, the stem cells are adherent. In specific embodiments, the adherent placental stem cells are CD200+ and HLA-G+; CD73+, CD105+, and CD200+; CD200+ and OCT-4+; CD73+, CD105+ and HLA-G+; CD73+ and CD105+ and facilitates the formation of one or more embryoid-like bodies in a population of placental cells comprising said stem cell when said population is cultured under conditions that allow the formation of an embryoid-like body; or OCT-4+ and facilitates the formation of one or more embryoid-like bodies in a population of placental cells comprising the stem cell when said population is cultured under conditions that allow formation of embryoid-like bodies; or any combination thereof. In more specific embodiments of the nonadherent placental stem cells, the isolated CD200+, HLA-G+ stem cell is CD34−, CD38−, CD45−, CD73+ and CD105+; the isolated CD73+, CD105+, and CD200$^+$ stem cell is CD34$^-$, CD38$^-$, CD45$^-$, and HLA-G$^+$; the isolated CD200$^+$, OCT-4$^+$ stem cell is CD34$^-$, CD38$^-$, CD45$^-$, CD73$^+$, CD105$^+$ and HLA-G$^+$; the isolated stem cell of claim 1, wherein said CD73$^+$, CD105$^+$ and HLA-G$^+$ stem cell is CD34$^-$, CD45$^-$, OCT-4$^+$ and CD200$^+$; the isolated CD73$^+$ and CD105$^+$ stem cell that facilitates the formation of one or more embryoid-like bodies is OCT4$^+$, CD34$^-$, CD38$^-$ and CD45$^-$; and/or the isolated OCT-4$^+$ and which facilitates the formation of one or more embryoid-like bodies is CD73$^+$, CD105$^+$, CD200$^+$, CD34$^-$, CD38$^-$, and CD45$^-$. In certain embodiments, the population comprises 1×10$^6$ said stem cells. In certain embodiments, the population comprises 5×10$^6$ said stem cells. In certain embodiments, the population comprises 1×10$^7$ said stem cells. In certain embodiments, the population comprises 5×10$^7$ said stem cells. In certain embodiments, the population comprises 1×10$^8$ said stem cells. In certain embodiments, the population comprises 5×10$^8$ said stem cells. In certain embodiments, the population comprises 1×10$^9$ said stem cells. In certain embodiments, the population comprises 5×10$^9$ said stem cells. In certain embodiments, the population comprises 1×10$^{10}$ said stem cells. In certain embodiments, the stem cells have been passaged no more than 5 times. In certain embodiments, the stem cells have been passaged no more than 10 times. In certain embodiments, the stem cells have been passaged no more than 15 times. In certain embodiments, the stem cells have been passaged no more than 20 times. In certain embodiments, the population has been expanded.

In certain embodiments, the implantable scaffolding substrate is selected from the group consisting of a β-tricalcium phosphate substrate, a β-tricalcium phosphate-collagen substrate, a collagen substrate, a calcium phosphate substrate, a mineralized human placental collagen substrate, and a hyaluronic acid substrate. In certain embodiments, the implantable scaffolding substrate is a β-tricalcium phosphate substrate. In certain embodiments, the implantable scaffolding substrate is a β-tricalcium phosphate-collagen substrate. In certain embodiments, the implantable scaffolding substrate is a collagen substrate. In certain embodiments, the implantable scaffolding substrate is a calcium phosphate substrate. In certain embodiments, the implantable scaffolding substrate is a mineralized human placental collagen substrate and/or scaffold.

In certain embodiments, provided herein is a method for formulating an injectable composition, comprising combining a population of placental stem cells with injectable hyaluronic acid or collagen, wherein said stem cells are CD34$^+$ and CD44$^-$. In certain embodiments, the stem cells are CD9$^+$, CD54$^+$, CD90$^+$, or CD166$^+$. In certain embodiments, the stem cells are CD9$^+$, CD54$^+$, CD90$^+$, and CD166$^+$. In certain embodiments, the stem cells are CD31$^+$, CD117$^+$, CD133$^+$, or CD200$^+$. In certain embodiments, the stem cells are CD31$^+$, CD117$^+$, CD133$^+$, and CD200$^+$. In certain embodiments, at least about 70% of said cells are CD34$^+$ and CD44$^-$ stem cells. In certain embodiments, at least about 90% of said cells are CD34$^+$ and CD44$^-$ stem cells. In certain embodiments, the population has been expanded. In certain embodiments, the stem cells are adherent. In certain embodiments, the composition comprises injectable hyaluronic acid. In certain embodiments, the composition comprises injectable collagen. Also provided herein are compositions comprising a population of nonadherent stem cells and injectable hyaluronic acid or collagen.

In yet another aspect, provided herein is a method for treating bone defects in a subject, comprising administering to a subject in need thereof an implantable or injectable composition comprising a population of stem cells, wherein said stem cells are CD34$^+$ and CD44$^-$, thereby treating the bone defect in the subject. In certain embodiments, the bone defect is (a) an osteolytic lesion associated with a cancer, (b) a bone fracture, or (c) a spine in need of fusion. In certain embodiments, the osteolytic lesion is associated with multiple myeloma, bone cancer, or metastatic cancer. In certain embodiments, the bone fracture is a non-union fracture. In certain embodiments, an implantable composition comprising a population of nonadherent stem cells is administered to the subject. In certain embodiments, the implantable composition is surgically implanted. In certain embodiments, an injectable composition comprising a population of nonadherent stem cells is administered to the subject. In certain embodiments, the injectable composition is surgically administered to the region of the bone defect. In certain embodiments, the injectable composition is systemically administered.

In certain embodiments, the stem cells are CD9$^+$, CD54$^+$, CD90$^+$, or CD166$^+$. In certain embodiments, the stem cells are CD9$^+$, CD54$^+$, CD90$^+$, and CD166$^+$. In certain embodiments, the stem cells are CD31$^+$, CD117$^+$, CD133$^+$, or CD200$^+$. In certain embodiments, the stem cells are CD31$^+$, CD117$^+$, CD133$^+$, and CD200$^+$. In certain embodiments, at least about 70% of said cells are CD34$^+$ and CD44$^-$ stem cells. In certain embodiments, at least about 90% of said cells are CD34$^+$ and CD44$^-$ stem cells. In certain embodiments, the population has been expanded.

In yet another aspect, provided herein is a method for treating bone defects in a subject, comprising administering to a subject in need thereof an implantable or injectable composition comprising a population of stem cells, wherein said stem cells are CD34$^-$ and, thereby treating the bone defect in the subject. In certain embodiments, the bone defect is (a) an osteolytic lesion associated with a cancer, (b) a bone fracture, or (c) a spine in need of fusion. In certain embodiments, the osteolytic lesion is associated with multiple myeloma, bone cancer, or metastatic cancer. In certain embodiments, the bone fracture is a non-union fracture. In certain embodiments, an implantable composition comprising a population of adherent stem cells is administered to the subject. In certain embodiments, the implantable composition is surgically implanted. In certain embodiments, an injectable composition comprising a population of adherent stem cells is administered to the subject. In certain embodiments, the injectable composition is surgically administered to the region of the bone defect. In certain embodiments, the injectable composition is systemically administered.

In more specific embodiments of the nonadherent placental stem cells, the isolated CD200$^+$, HLA-G$^+$ stem cell is CD34$^-$, CD38$^-$, CD45$^-$, CD73$^+$ and CD105$^+$; the isolated CD73$^+$, CD105$^+$, and CD200$^+$ stem cell is CD34$^-$, CD38$^-$, CD45$^-$, and HLA-G$^+$; the isolated CD200$^+$, OCT-4$^+$ stem cell is CD34$^-$, CD38$^-$, CD45$^-$, CD73$^+$, CD105$^+$ and HLA-G$^+$; the isolated stem cell of claim 1, wherein said CD73$^+$, CD105$^+$ and HLA-G$^+$ stem cell is CD34$^-$, CD45$^-$, OCT-4$^+$ and CD200$^+$; the isolated CD73$^+$ and CD105$^+$ stem cell that facilitates the formation of one or more embryoid-like bodies is OCT4$^+$, CD34$^-$, CD38$^-$ and CD45$^-$; and/or the isolated OCT-4$^+$ and which facilitates the formation of one or more embryoid-like bodies is CD73$^+$, CD105$^+$, CD200$^+$, CD34$^-$, CD38$^-$, and CD45$^-$. In certain embodiments, the population comprises 1×10$^6$ said stem cells. In certain embodiments, the population comprises 5×10$^6$ said stem cells. In certain embodiments, the population comprises 1×10$^7$ said stem cells. In certain embodiments, the population comprises 5×10$^7$ said stem cells. In certain embodiments, the population comprises 1×10$^8$ said stem cells. In certain embodiments, the population comprises 5×10⁸ said stem cells. In certain embodiments, the population comprises 1×10⁹ said stem cells. In certain embodiments, the population comprises 5×10⁹ said stem cells. In certain embodiments, the population comprises 1×10¹⁰ said stem cells. In certain embodiments, the stem cells have been passaged no more than 5 times. In certain embodiments, the stem cells have been passaged no more than 10 times. In certain embodiments, the stem cells have been passaged no more than 15 times. In certain embodiments, the stem cells have been passaged no more than 20 times. In certain embodiments, the population has been expanded.

Also provided herein are methods for producing populations of stem cells derived from mammalian placenta. In one embodiment, for example, provided herein is a method of producing a cell population comprising selecting cells that (a) adhere to a substrate, and (b) express CD200 and HLA-G; and isolating said cells from other cells to form a cell population. In another embodiment, provided herein is a method of producing a cell population, comprising selecting cells that (a) adhere to a substrate, and (b) express CD73, CD105, and CD200; and isolating said cells from other cells to form a cell population. In another embodiment, provided herein is a method of producing a cell population, comprising selecting cells that (a) adhere to a substrate and (b) express CD200 and OCT-4; and isolating said cells from other cells to form a cell population. In yet another embodiment, provided herein is a method of producing a cell population, comprising selecting cells that (a) adhere to a substrate, (b) express CD73 and CD105, and (c) facilitate the formation of one or more embryoid-like bodies when cultured with a population of placental cells under conditions that allow for the formation of embryoid-like bodies; and isolating said cells from other cells to form a cell population. In another embodiment, provided herein is a method of producing a cell population, comprising selecting cells that (a) adhere to a substrate, and (b) express CD73, CD105 and HLA-G; and isolating said cells from other cells to form a cell population. Also provided herein is a method of producing a cell population, comprising selecting cells that (a) adhere to a substrate, (b) express OCT-4, and (c) facilitate the formation of one or more embryoid-like bodies when cultured with a population of placental cells under conditions that allow for the formation of embryoid-like bodies; and isolating said cells from other cells to form a cell population. In a specific embodiment of any of the foregoing methods, said substrate comprises fibronectin. In another specific embodiment, the methods comprise selecting cells that express ABC-p. In another specific embodiment, the methods comprise selecting cells exhibiting at least one characteristic specific to a mesenchymal stem cell. In a more specific embodiment, said characteristic specific to a mesenchymal stem cell is expression of CD29, expression of CD44, expression of CD90, or expression of a combination of the foregoing. In another specific embodiment of the methods, said selecting is accomplished using an antibody. In another specific embodiment, said selecting is accomplished using flow cytometry. In another specific embodiment, said selecting is accomplished using magnetic beads. In another specific embodiment, said selecting is accomplished by fluorescence-activated cell sorting. In another specific embodiment of the above methods, said cell population is expanded.

Also provided herein is a method of producing a stem cell line, comprising transforming a stem cell with a DNA sequence that encodes a growth-promoting protein; and exposing said stem cell to conditions that promote production of said growth-promoting protein. In a specific embodiment, said growth-promoting protein is v-myc, N-myc, c-myc, p53, SV40 large T antigen, polyoma large T antigen, E1a adenovirus or human papillomavirus E7 protein. In a more specific embodiment, said DNA sequence is regulatable. In more specific embodiment, said DNA sequence is regulatable by tetracycline. In another specific embodiment, said growth-promoting protein has a regulatable activity. In another specific embodiment, said growth-promoting protein is a temperature-sensitive mutant.

Also provided herein are cryopreserved stem cell populations. For example, provided herein is a population of CD200⁺, HLA-G⁺ stem cells, wherein said cells have been cryopreserved, and wherein said population is contained within a container. Also provided herein is a population of CD73⁺, CD105⁺, CD200⁺ stem cells, wherein said stem cells have been cryopreserved, and wherein said population is contained within a container. Also provided herein is a population of CD200⁺, OCT-4⁺ stem cells, wherein said stem cells have been cryopreserved, and wherein said population is contained within a container. Also provided herein is a population of CD73⁺, CD105⁺ stem cells, wherein said cells have been cryopreserved, and wherein said population is contained within a container, and wherein said stem cells facilitate the formation of one or more embryoid-like bodies when cultured with a population of placental cells under conditions that allow for the formation of embryoid-like bodies. Further provided herein is a population of CD73⁺, CD105⁺, HLA-G⁺ stem cells, wherein said cells have been cryopreserved, and wherein said population is contained within a container. Also provided herein is a population of OCT-4⁺ stem cells, wherein said cells have been cryopreserved, wherein said population is contained within a container, and wherein said stem cells facilitate the formation of one or more embryoid-like bodies when cultured with a population of placental cells under conditions that allow for the formation of embryoid-like bodies. In a specific embodiment of any of the foregoing cryopreserved populations, said container is a bag. In various specific embodiments, said population comprises about, at least, or at most $1\times10^6$ said stem cells, $5\times10^6$ said stem cells, $1\times10^7$ said stem cells, $5\times10^7$ said stem cells, $1\times10^8$ said stem cells, $5\times10^8$ said stem cells, $1\times10^9$ said stem cells, $5\times10^9$ said stem cells, or $1\times10^{10}$ said stem cells. In other specific embodiments of any of the foregoing cryopreserved populations, said stem cells have been passaged about, at least, or no more than 5 times, no more than 10 times, no more than 15 times, or no more than 20 times. In another specific embodiment of any of the foregoing cryopreserved populations, said stem cells have been expanded within said container.

Further provided herein is a method for preparing a mineralized collagen matrix, comprising mineralizing collagen and crosslinking the mineralized collagen matrix. In certain embodiments, the collagen is placental collagen. In certain embodiments, the collagen is mineralized with calcium phosphate. In certain embodiments, the collagen is crosslinked with butane diol diglycidyl ether. In certain embodiments, the ratio of calcium phosphate to collagen in the mineralization reaction is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5.

3.1 Definitions

As used herein, the term "SH2" refers to an antibody that binds an epitope on the marker CD105. Thus, cells that are referred to as SH2⁺ are CD105⁺.

As used herein, the terms "SH3" and SH4" refer to antibodies that bind epitopes present on the marker CD73. Thus, cells that are referred to as SH3⁺ and/or SH4⁺ are CD73⁺.

As used herein, the term "isolated stem cell" means a stem cell that is substantially separated from other, non-stem cells of the tissue, e.g., placenta, from which the stem cell is derived. A stem cell is "isolated" if at least about 50%, 60%, 70%, 80%, 90%, 95%, or at least 99% of the non-stem cells with which the stem cell is naturally associated are removed from the stem cell, e.g., during collection and/or culture of the stem cell.

As used herein, the term "population of isolated cells" means a population of cells that is substantially separated from other cells of the tissue, e.g., placenta, from which the population of cells is derived. A stem cell is "isolated" if at least about 50%, 60%, 70%, 80%, 90%, 95%, or at least 99% of the cells with which the population of cells, or cells from which the population of cells is derived, is naturally associated are removed from the stem cell, e.g., during collection and/or culture of the stem cell.

As used herein, the term "placental stem cell" refers to a stem cell or progenitor cell that is derived from a mammalian placenta, regardless of morphology, cell surface markers, or the number of passages after a primary culture. The term "placental stem cell" as used herein does not, however, refer to a trophoblast. A cell is considered a "stem cell" if the cell retains at least one attribute of a stem cell, e.g., a marker or gene expression profile associated with one or more types of stem cells; the ability to replicate at least 10-40 times in culture, the ability to differentiate into cells of all three germ layers; the lack of adult (i.e., differentiated) cell characteristics, or the like. The terms "placental stem cell" and "placenta-derived stem cell" may be used interchangeably.

As used herein, "placental perfusate" means perfusion solution that has been passed through at least part of a placenta, e.g., a human placenta, e.g., through the placental vasculature, including a plurality of cells collected by the perfusion solution during passage through the placenta.

As used herein, "placental perfusate cells" means nucleated cells, e.g., total nucleated cells, isolated from, or isolatable from, placental perfusate.

As used herein, a stem cell is "positive" for a particular marker when that marker is detectable. For example, a placental stem cell is positive for, e.g., CD73 because CD73 is detectable on placental stem cells in an amount detectably greater than background (in comparison to, e.g., an isotype control). A cell is also positive for a marker when that marker can be used to distinguish the cell from at least one other cell type, or can be used to select or isolate the cell when present or expressed by the cell.

As used herein, an "osteogenic cell" is a cell that is capable of either depositing hydroxyapatite, the main component of bone, or differentiating into a cell that is capable of depositing hydroxyapatite. An "osteogenic cell" is specifically contemplated as encompassing a cell ordinarily referred to as an osteoblast or an osteocyte.

As used herein, a "matrix" refers to a three-dimensional substance that is characterized by lacunae dispersed throughout the substance. The lacunae are suitable, for example, for growth of cells, e.g., stem cells, placenta-derived adherent stem cells, and/or osteogenic cells, within the matrix, Exemplary matrices include, but are not limited to, a β-tricalcium phosphate substrate, a β-tricalcium phosphate-collagen substrate, a collagen substrate, a calcium phosphate substrate, a mineralized human placental collagen substrate, a hyaluronic acid substrate, and a ceramic substrate. Preferably, the matrix can be mineralized by an osteogenic cell present in the lacunae of the matrix.

4. BRIEF DESCRIPTION OF THE FIGURES

FIG. 1: Viability of placental stem cells from perfusion (A), amnion (B), chorion (C), amnion-chorion plate (D) or umbilical cord (E). Numbers on X-axis designate placenta from which stem cells were obtained.

Figure 2:
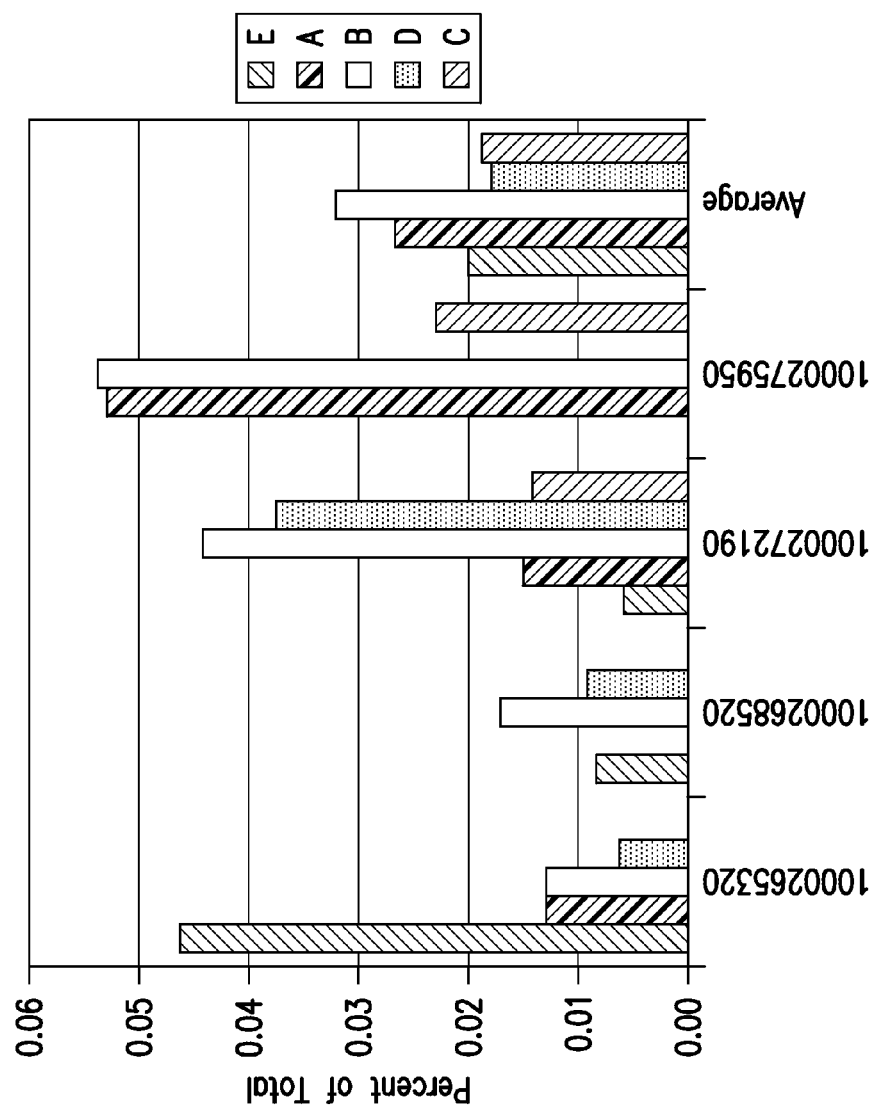

FIG. 2: Percent HLA ABC$^-$/CD45$^{31}$/CD34$^-$/CD133$^+$ cells from perfusion (A), amnion (B), chorion (C), amnion-chorion plate (D) or umbilical cord (E) as determined by FACSCalibur. Numbers on X-axis designate placenta from which stem cells were obtained.

Figure 3:
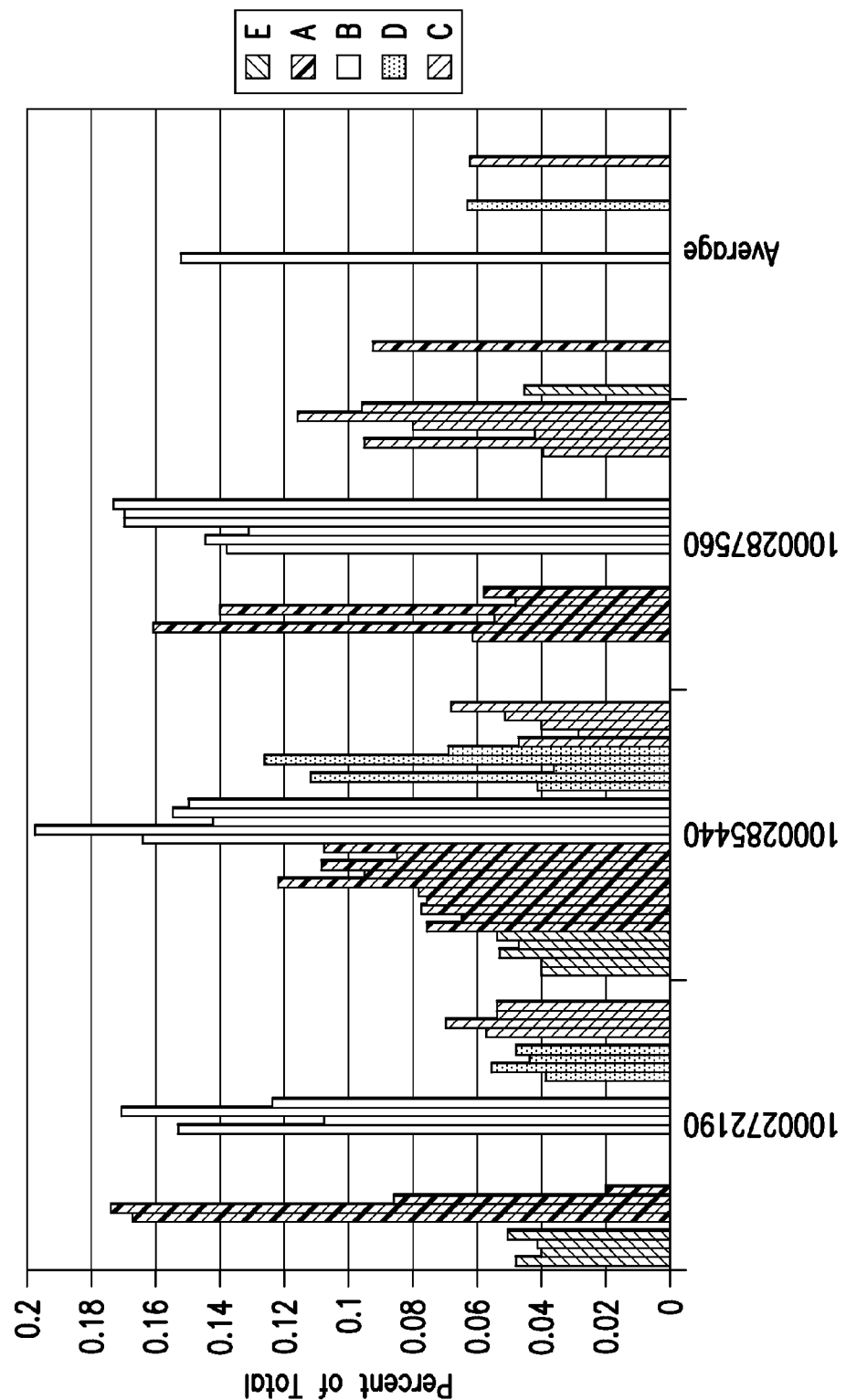

FIG. 3: Percent HLA ABC$^-$/CD45$^-$/CD34$^-$/CD133$^+$ cells from perfusion (A), amnion (B), chorion (C), amnion-chorion plate (D) or umbilical cord (E), as determined by FACS Aria. Numbers on X-axis designate placenta from which stem cells were obtained.

Figure 4:
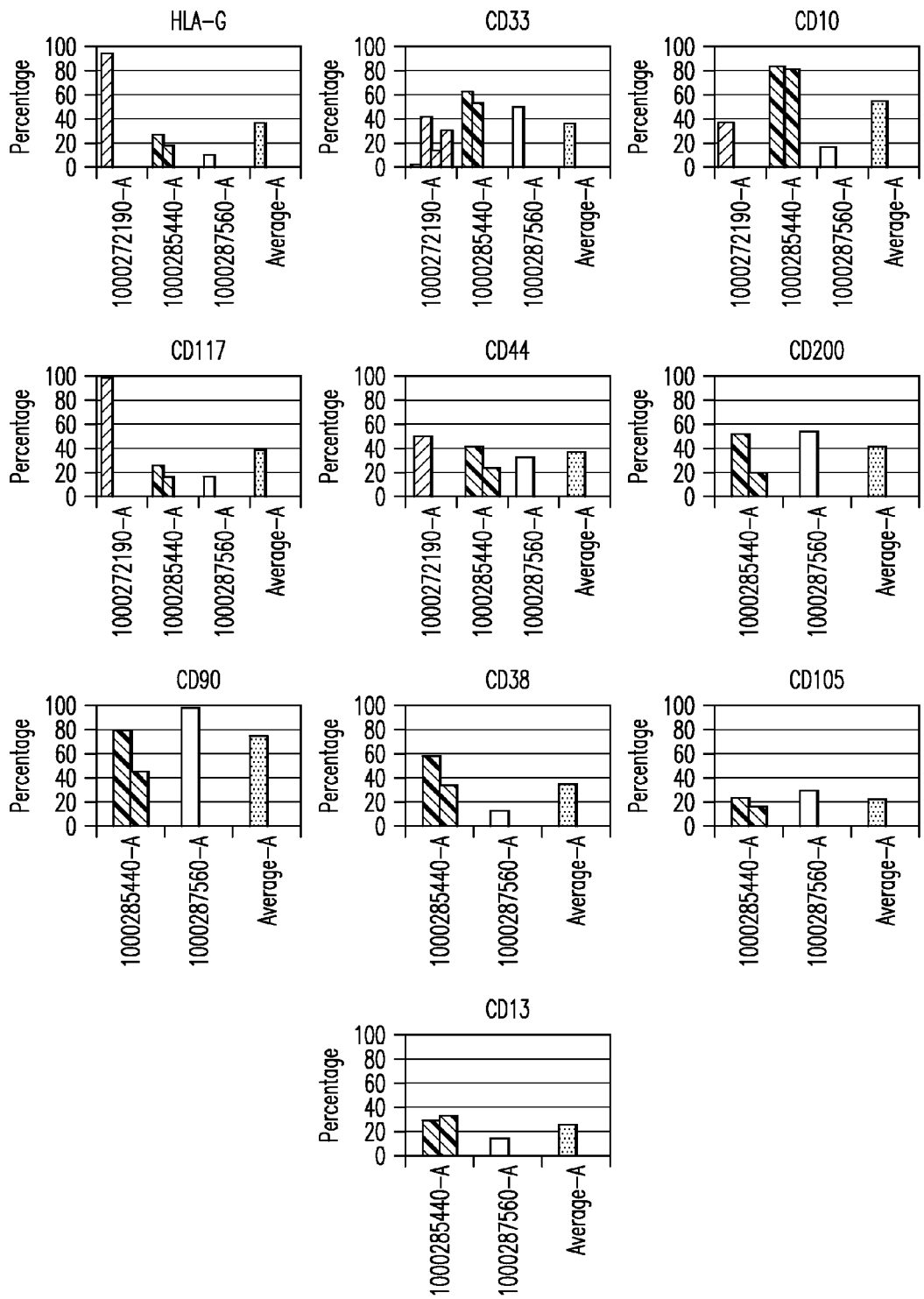

FIG. 4: HLA-G, CD10, CD13, CD33, CD38, CD44, CD90, CD105, CD117, CD200 expression in stem cells derived from placental perfusate.

Figure 5:
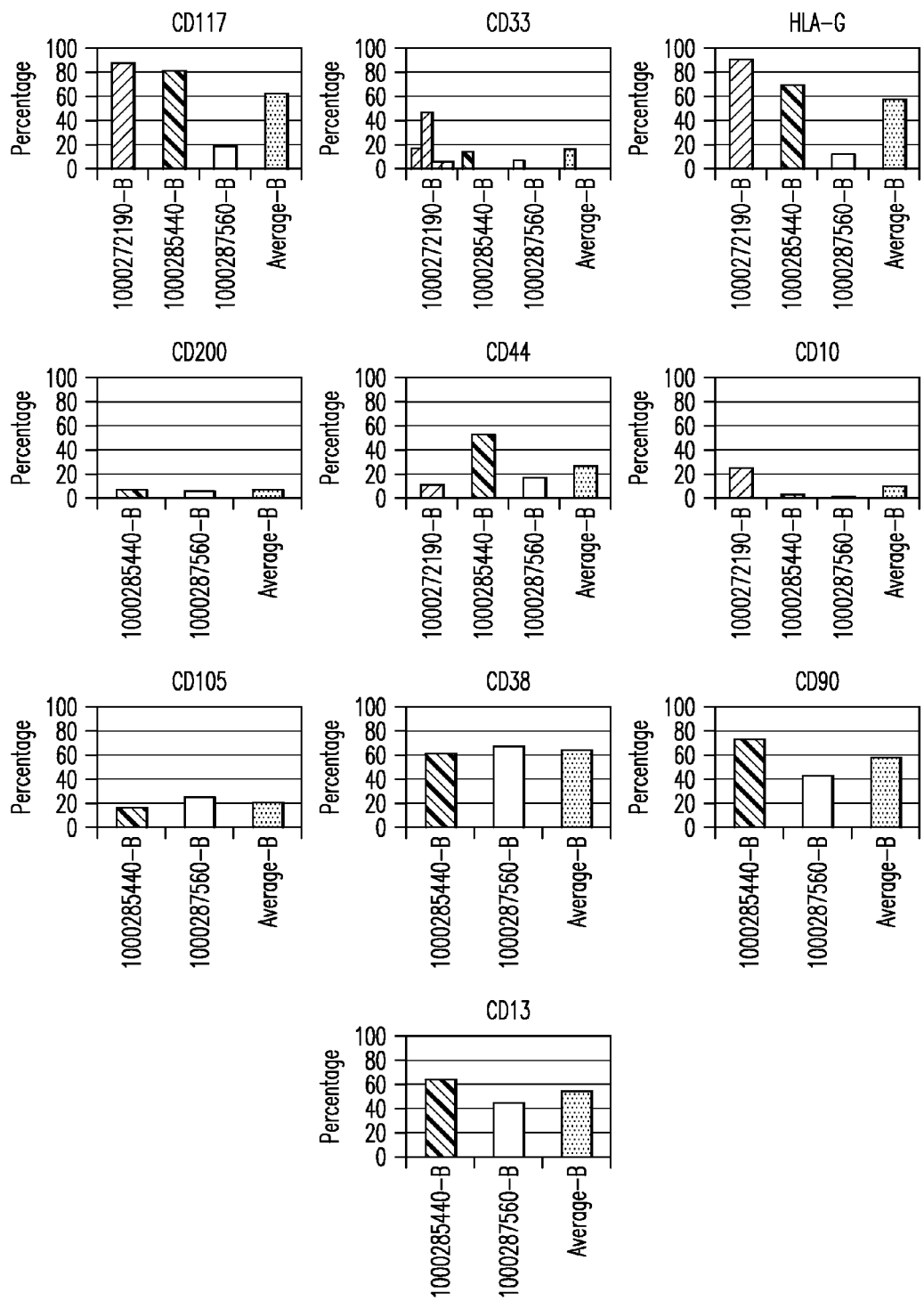

FIG. 5: HLA-G, CD10, CD13, CD33, CD38, CD44, CD90, CD105, CD117, CD200 expression in stem cells derived from amnion.

Figure 6:
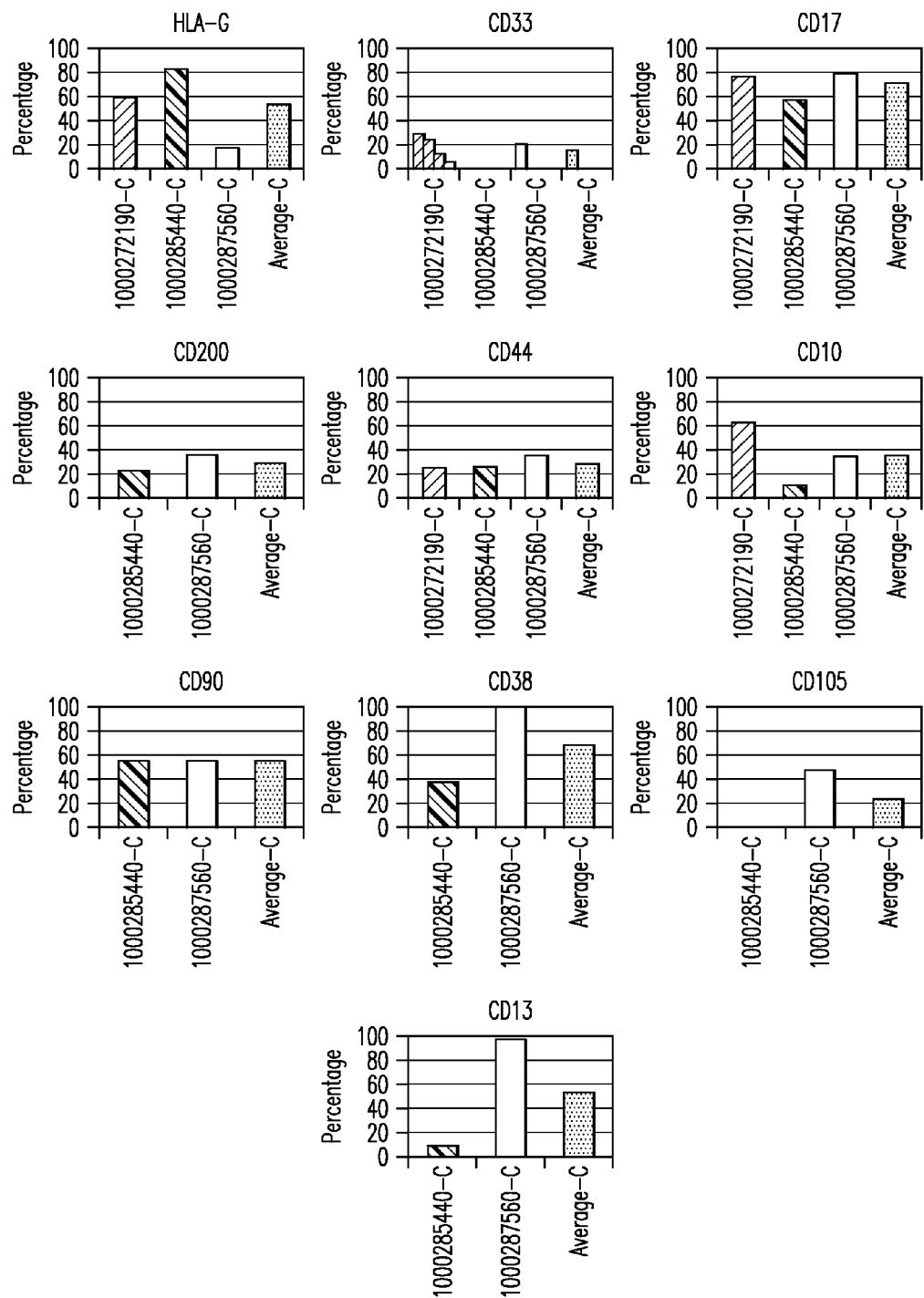

FIG. 6: HLA-G, CD10, CD13, CD33, CD38, CD44, CD90, CD105, CD117, CD200 expression in stem cells derived from chorion.

Figure 7:
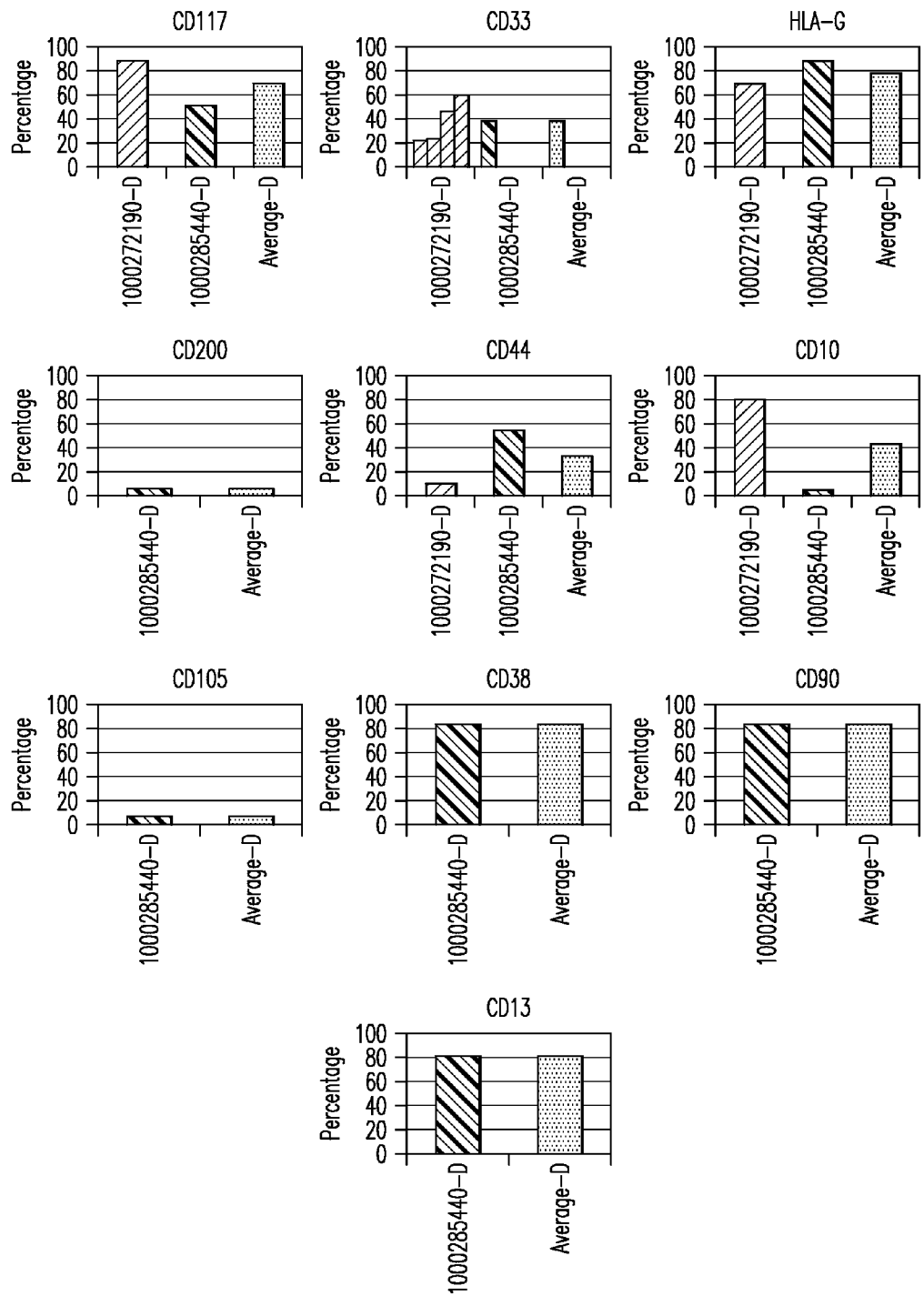

FIG. 7: HLA-G, CD10, CD13, CD33, CD38, CD44, CD90, CD105, CD117, CD200 expression in stem cells derived from amnion-chorion plate.

Figure 8:
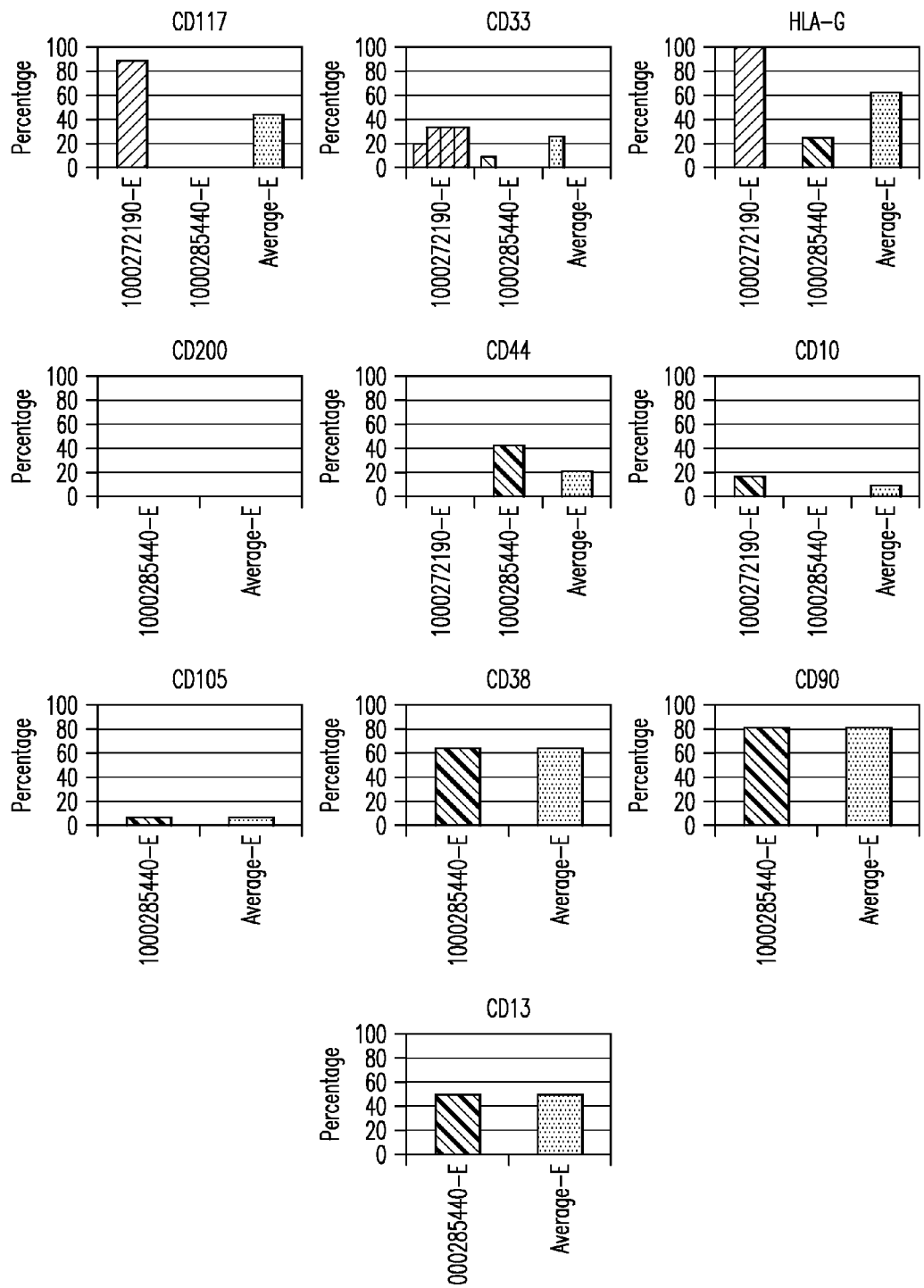

FIG. 8: HLA-G, CD10, CD13, CD33, CD38, CD44, CD90, CD105, CD117, CD200 expression in stem cells derived from umbilical cord.

Figure 9:
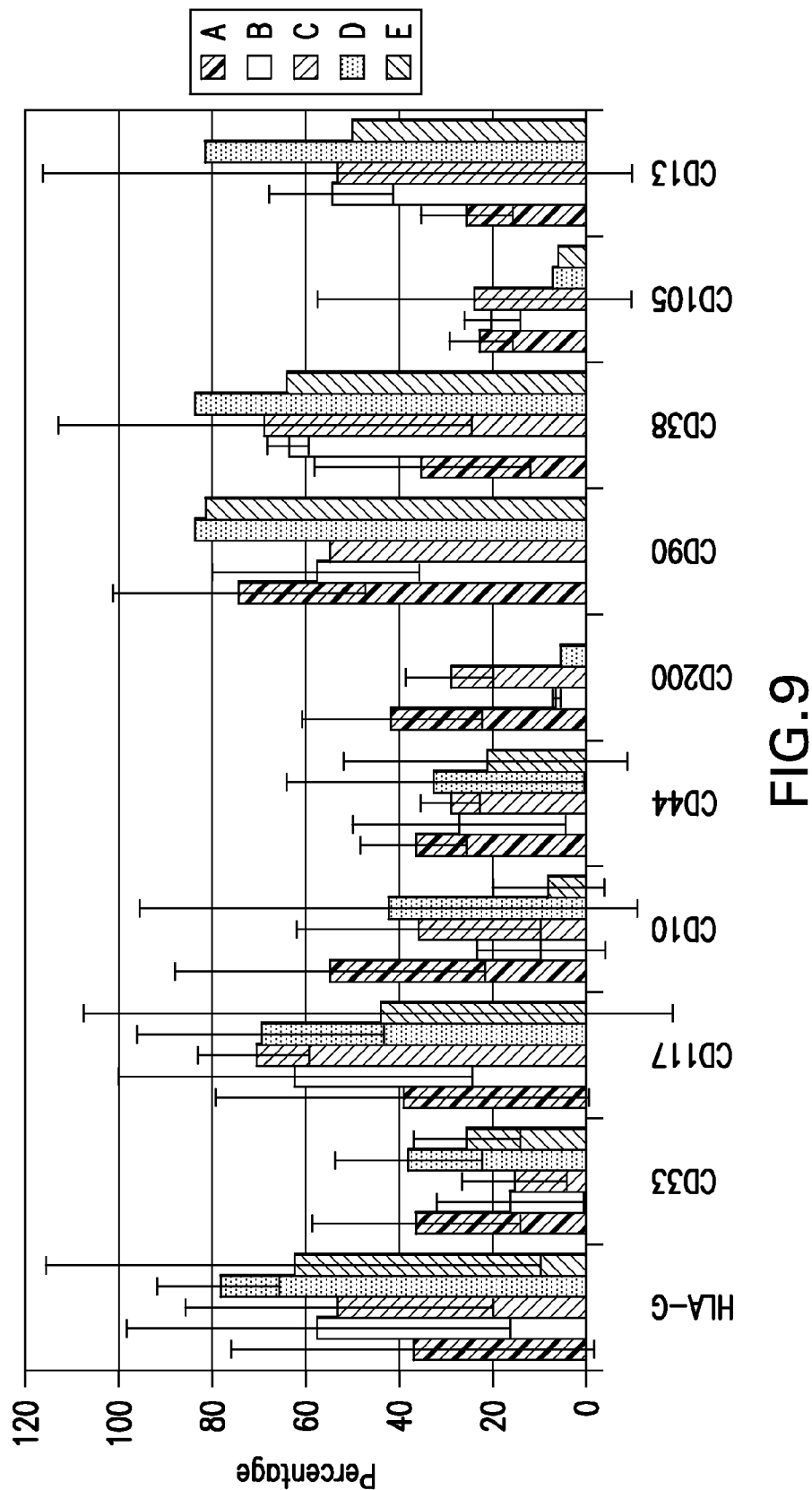

FIG. 9: Average expression of HLA-G, CD10, CD13, CD33, CD38, CD44, CD90, CD105, CD117, CD200 expression in stem cells derived from perfusion (A), amnion (B), chorion (C), amnion-chorion plate (D) or umbilical cord (E).

Figure 10:
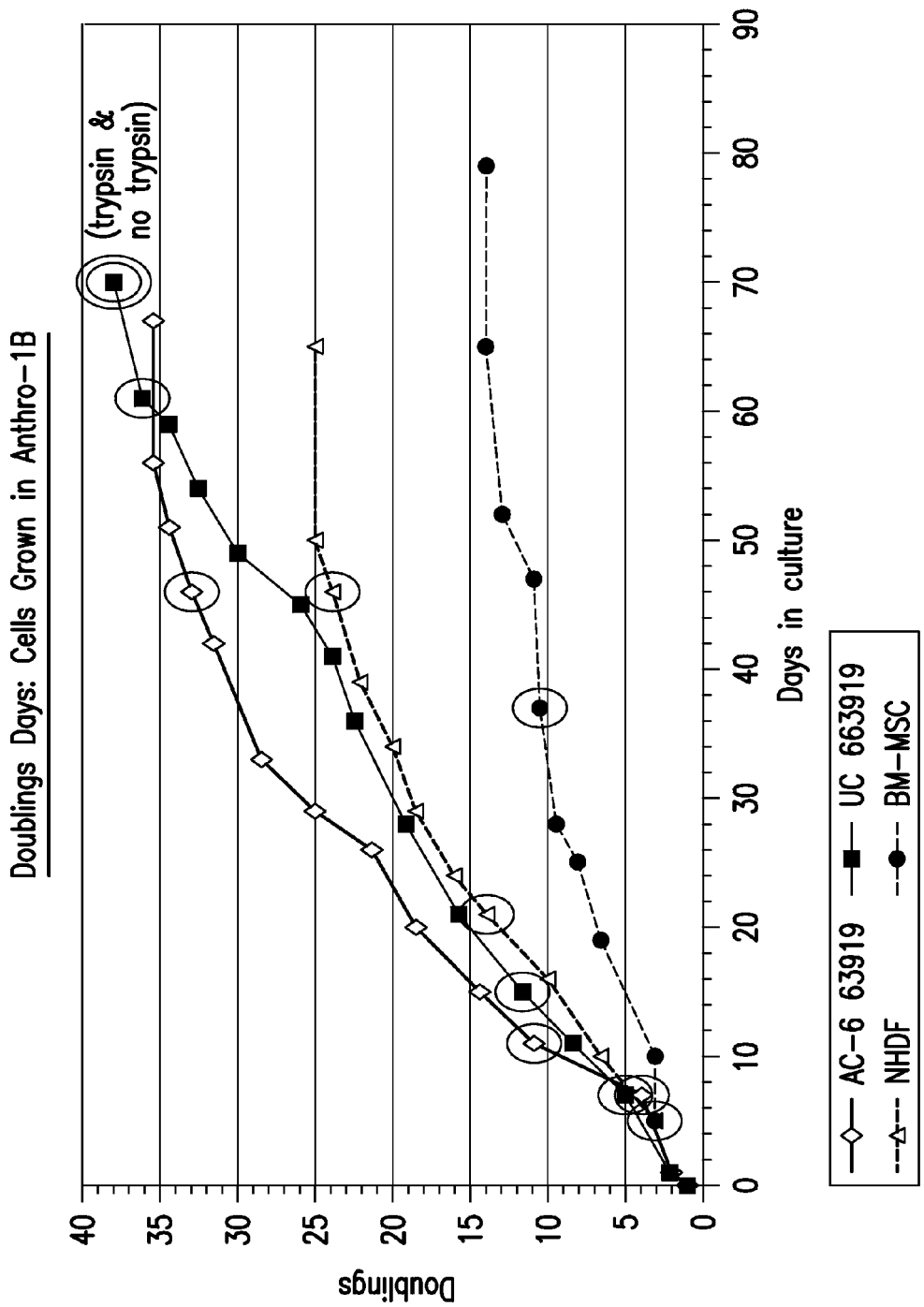

FIG. 10: Culture time courses for amnion/chorion (AC), umbilical cord (UC), bone marrow-derived stem cell (BM-MSC) and human dermal fibroblast (NHDF) cell lines used in this study. All cultures were grown and propagated using the same seeding and passage densities. Circles indicate which cultures were used for RNA isolation. Late cultures were harvested just prior to senescence. Two UC cultures were harvested at 38 doublings (UC-38) to compare the effect of trypsinization on gene expression. All other cultures were lysed directly in their culture flasks prior to RNA isolation.

Figure 11:
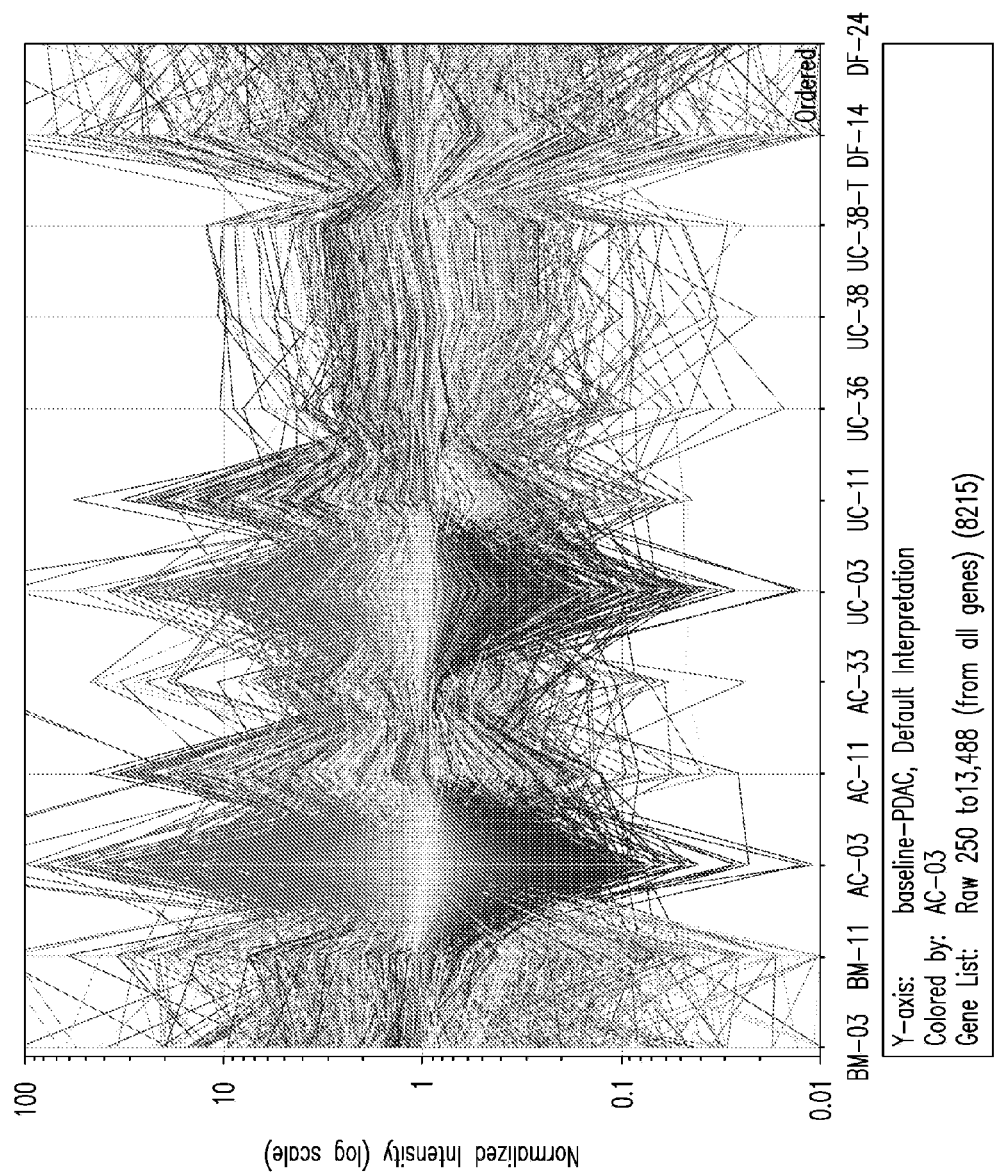

FIG. 11: Line plot of relative expression levels of 8215 genes in amnion/chorion (AC), umbilical cord (UC), bone marrow-derived stem cell (BM-MSC) and human dermal fibroblast (DF) cells. The number associated with each cell line designation on the X-axis indicates the number of days the cell line was cultured prior to evaluation of gene expression levels. The chart was generated from RNA expression data analyzed by GeneSpring software. AC-03 was used as the selected condition.

Figure 12:
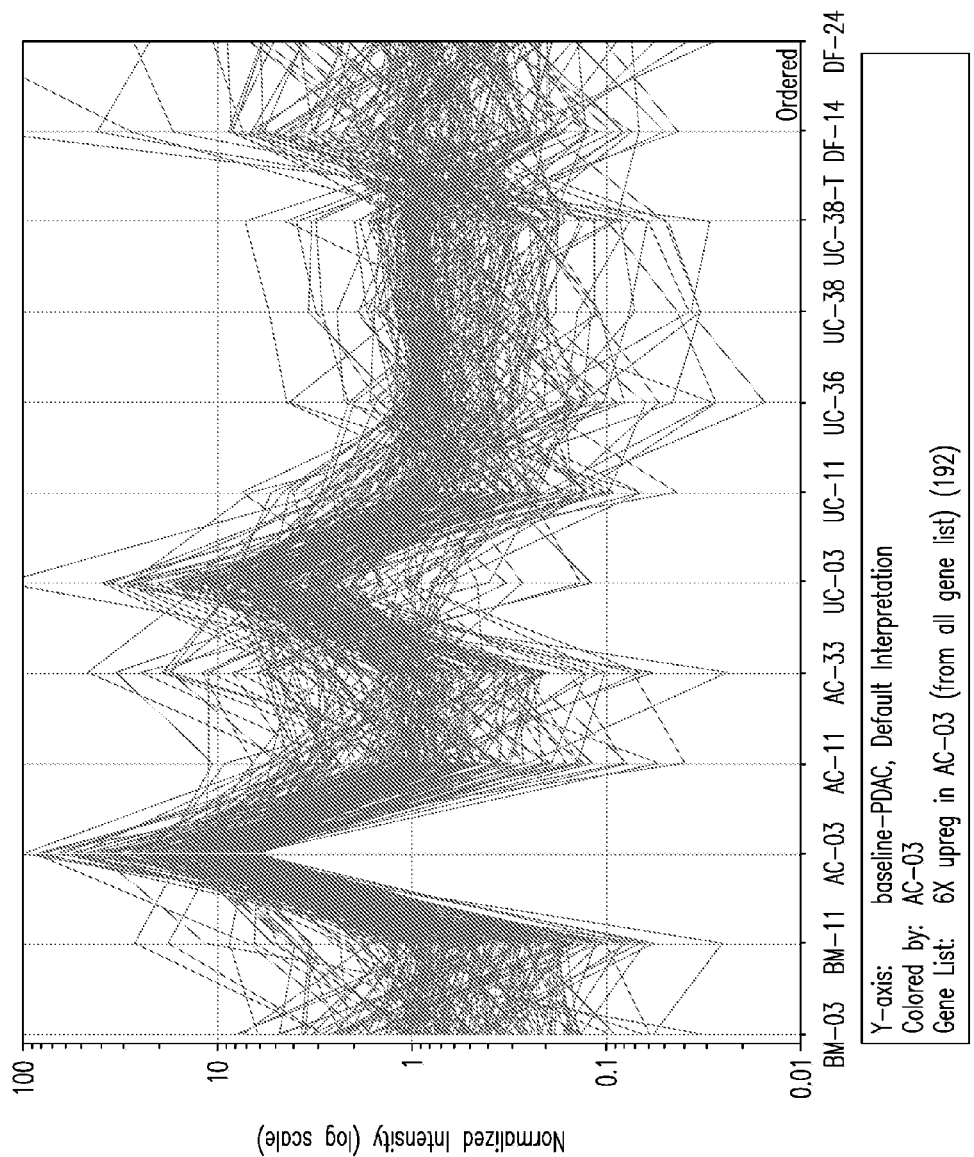

FIG. 12: Subset of the all genes list showing genes over-expressed ≥6-fold in AC-03 for amnion/chorion (AC), umbilical cord (UC), bone marrow-derived stem cell (BM-MSC) and human dermal fibroblast (DF) cells. The number associated with each cell line designation on the X-axis indicates the number of days the cell line was cultured prior to evaluation of gene expression levels. The chart was generated from RNA expression data analyzed by GeneSpring software. AC-03 was used as the selected condition.

Figure 13:
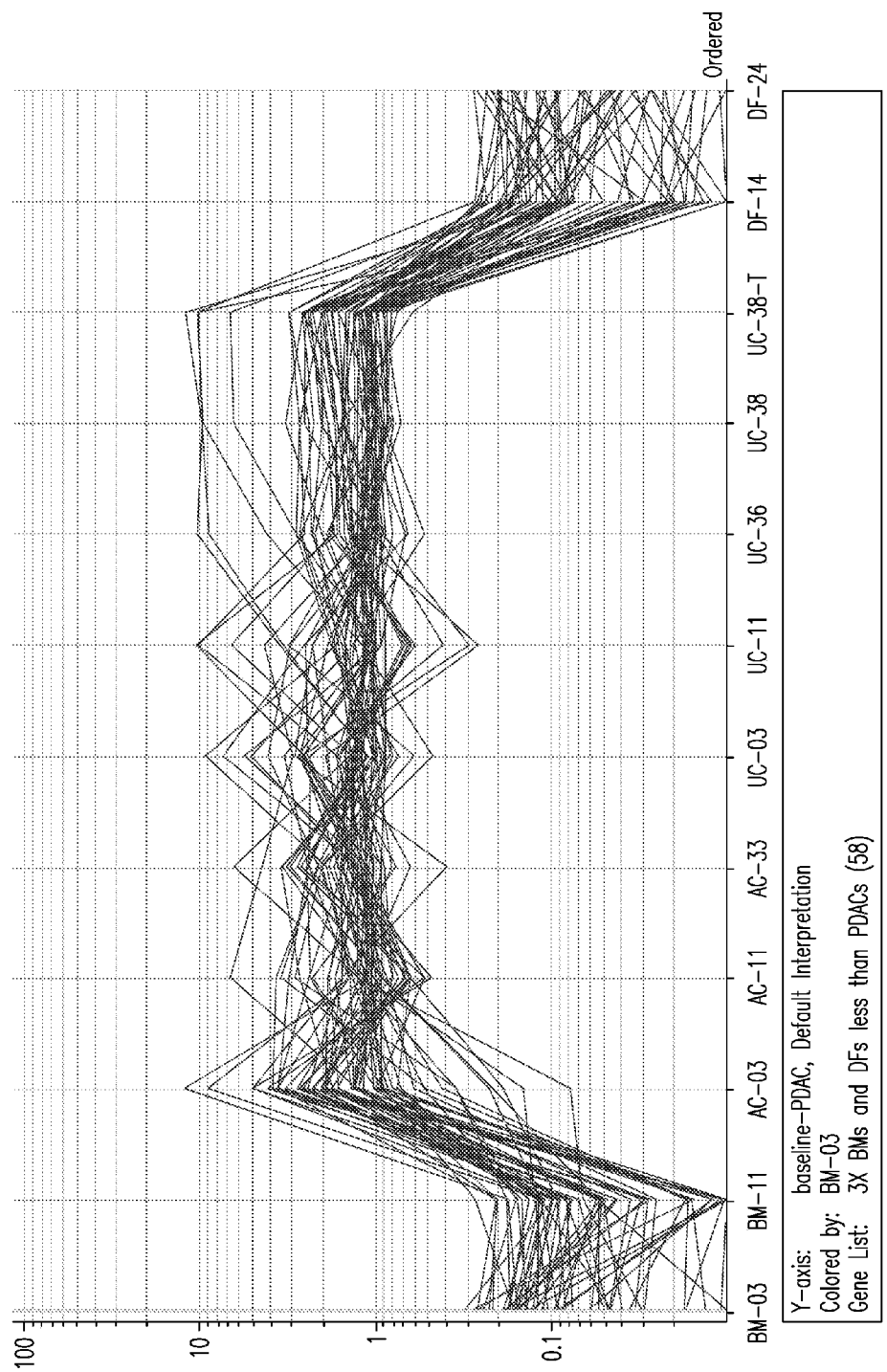

FIG. 13: Placental stem cell-specific or umbilical cord stem cell-specific genes found by fold change filtering for amnion/chorion (AC), umbilical cord (UC), bone marrow-derived stem cell (BM-MSC) and human dermal fibroblast (DF) cells. The number associated with each cell line designation on the X-axis indicates the number of days the cell line was cultured prior to evaluation of gene expression levels. The chart was generated from RNA expression data analyzed by Gene-Spring software. AC-03 was used as the selected condition.

Figure 14A:
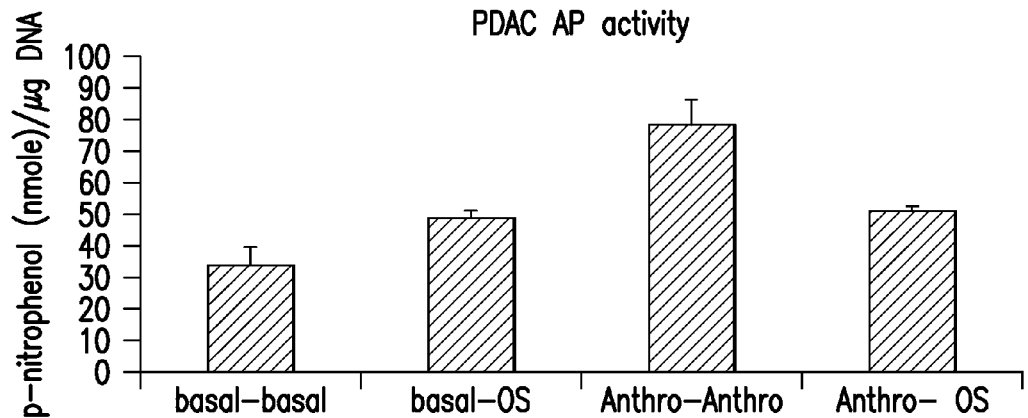
Figure 14B:
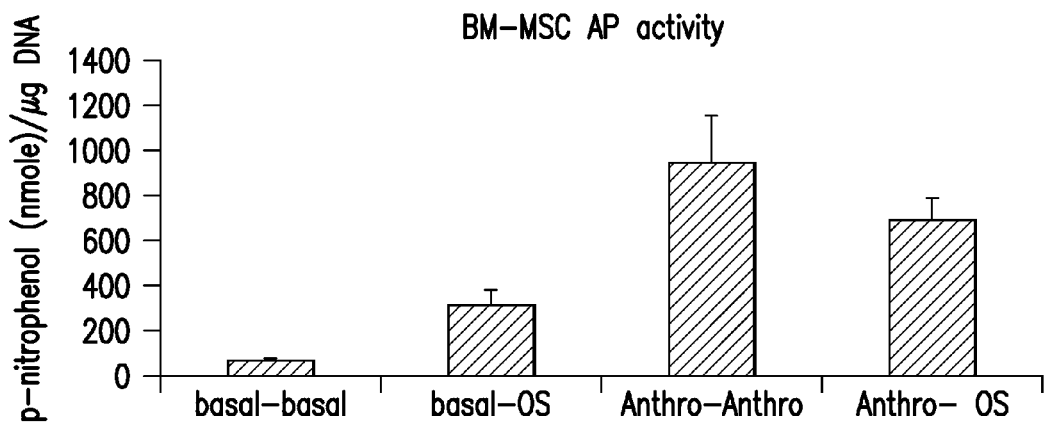

FIG. 14: Alkaline phosphate activity of both placental stem cells (FIG. 14A) and mesenchymal stem cells (FIG. 14B) cultured in two different media formulations.

FIG. 15: Mineralization of placental stem cells (FIG. 15A) cultured in two different media formulations.

Figure 16A:
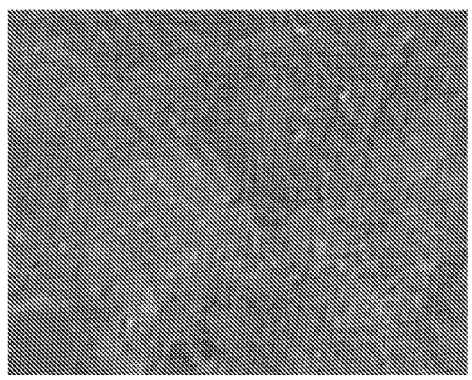
Figure 16B:
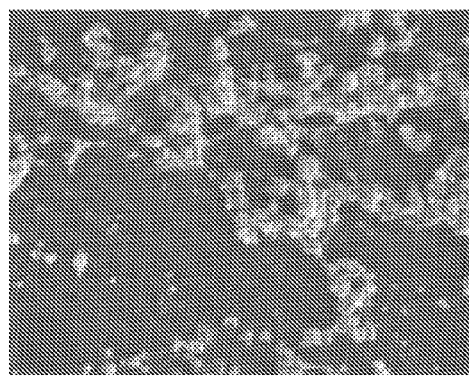

FIG. 16: Deposits of minerals by placental stem cells induced in OS medium, but not in Anthro1B medium.

Figure 17:
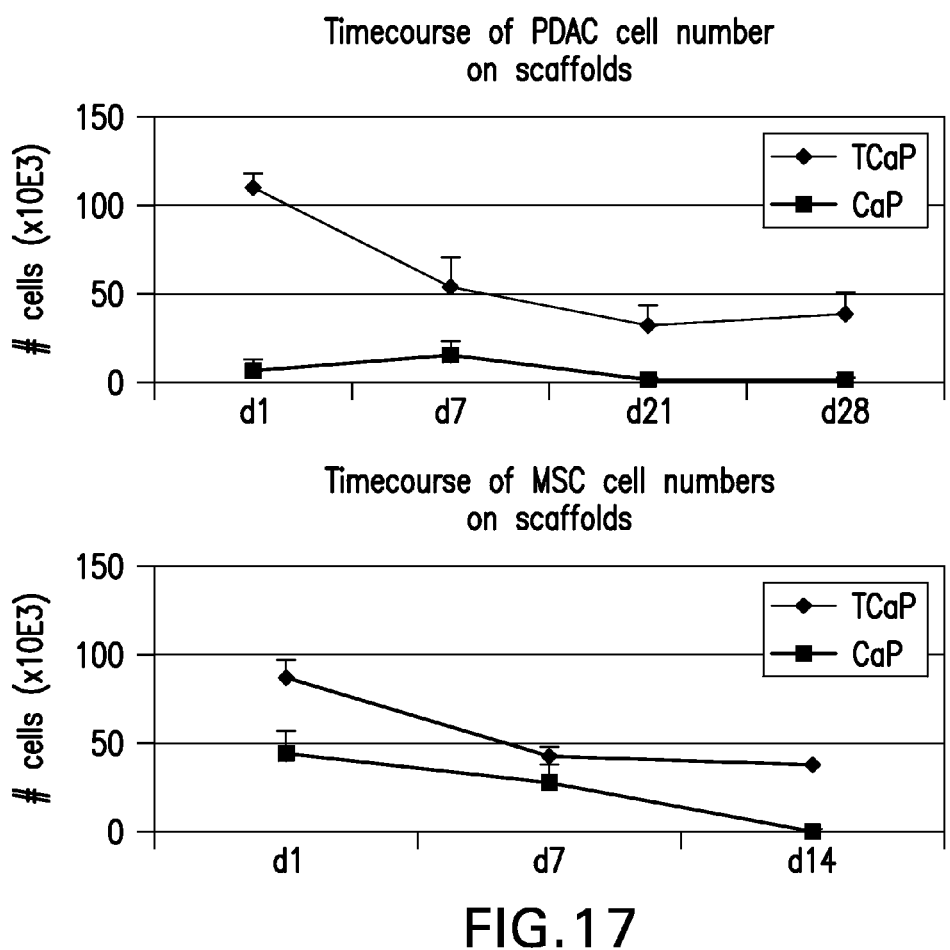

FIG. 17: Time course of growth of placental stem cells and mesenchymal stem cells grown on two different scaffolds.

Figure 18:
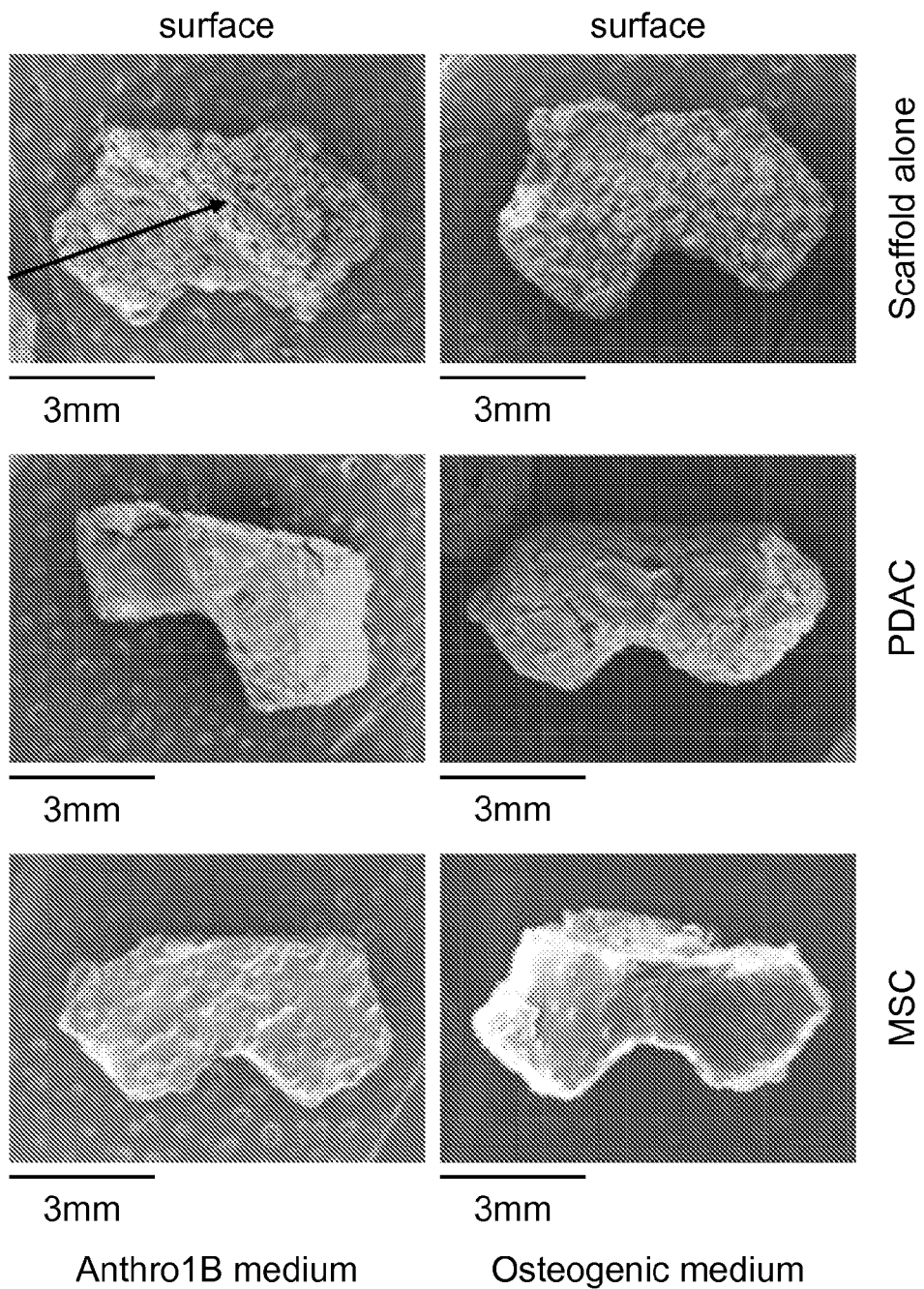

FIG. 18: Scanning electron micrographs (20×) of placental stem cells and mesenchymal stem cells grown in OS medium and Anthro1B on a β-tricalcium phosphate substrate.

Figure 19:
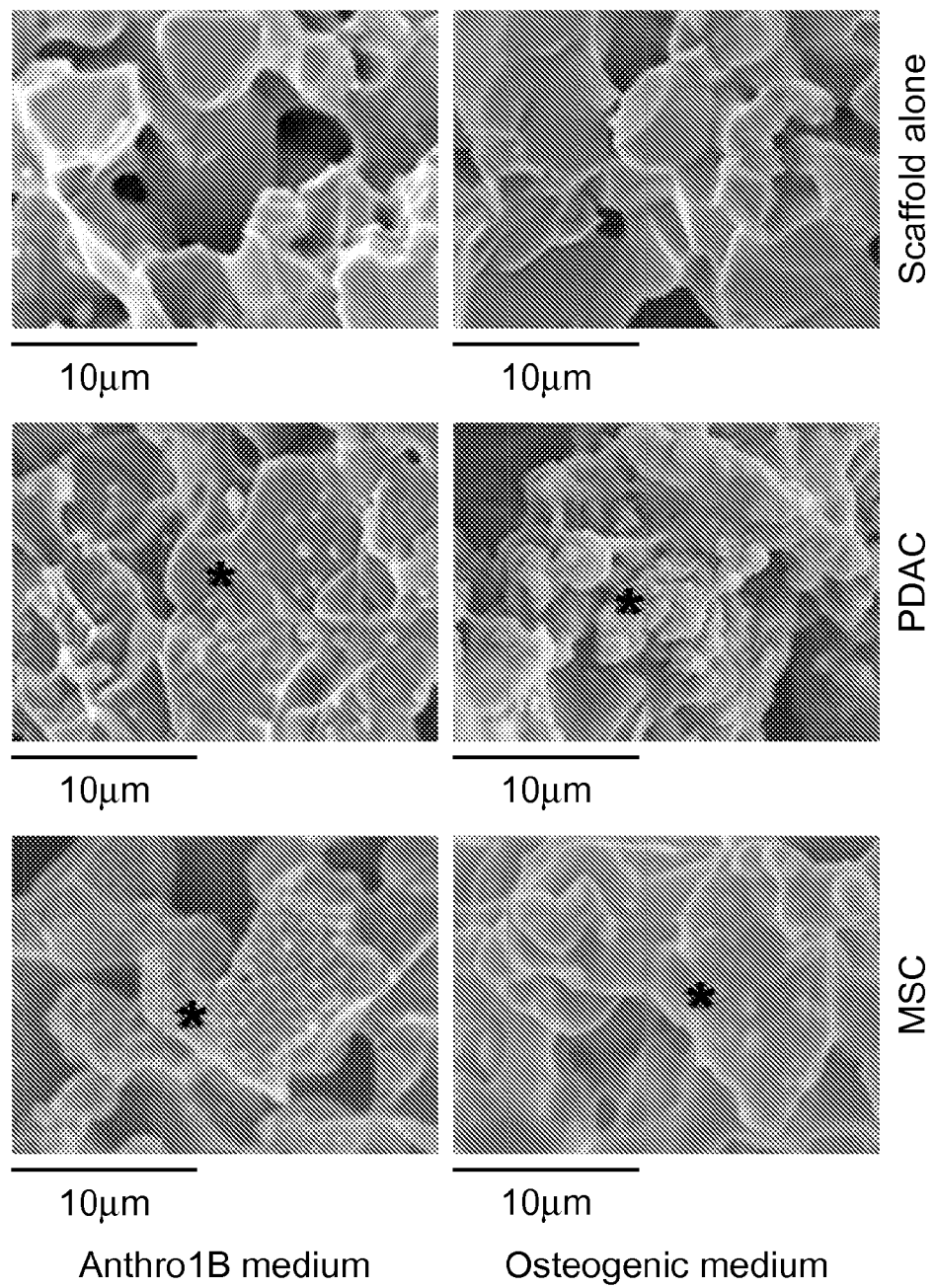
Figure 20A:
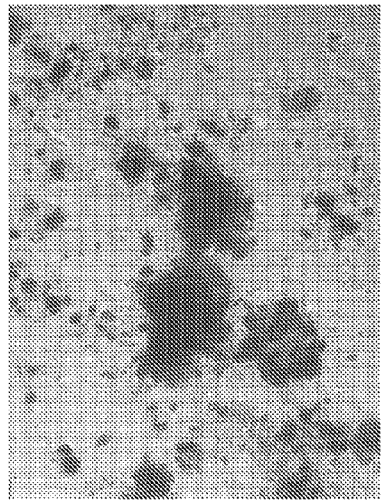
Figure 20B:
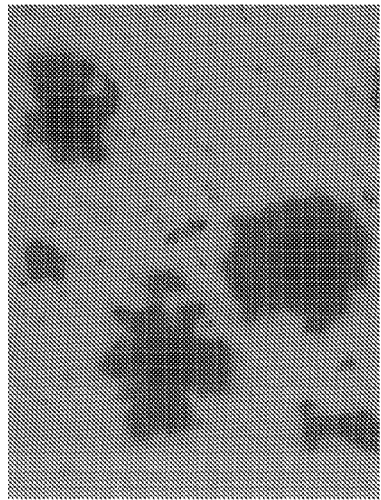
Figure 20C:
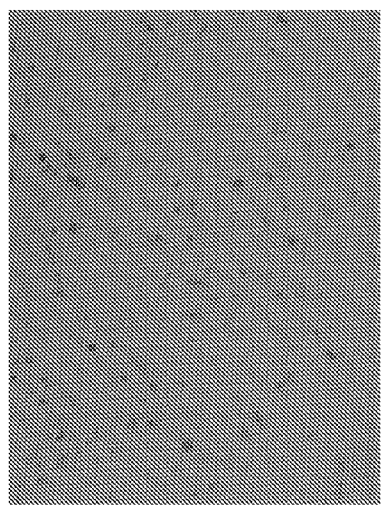
Figure 20D:
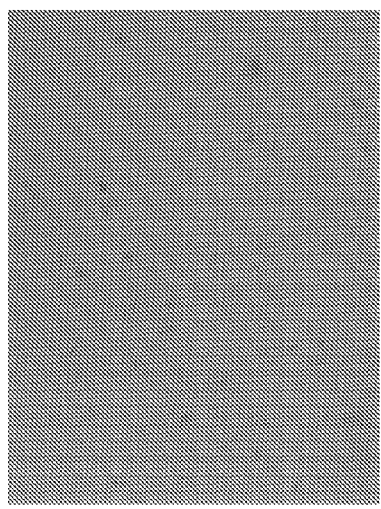

FIG. 19: Scanning electron micrographs (5000×) of placental stem cells and mesenchymal stem cells grown in OS medium and Anthro1B on a β-tricalcium phosphate substrate.

FIG. 20: Alizarin red staining of mesenchymal stem cells and stem cells obtained from human perfused placenta cells showing calcium mineralization following culture in OS medium, but not DMEM.

Figure 21:
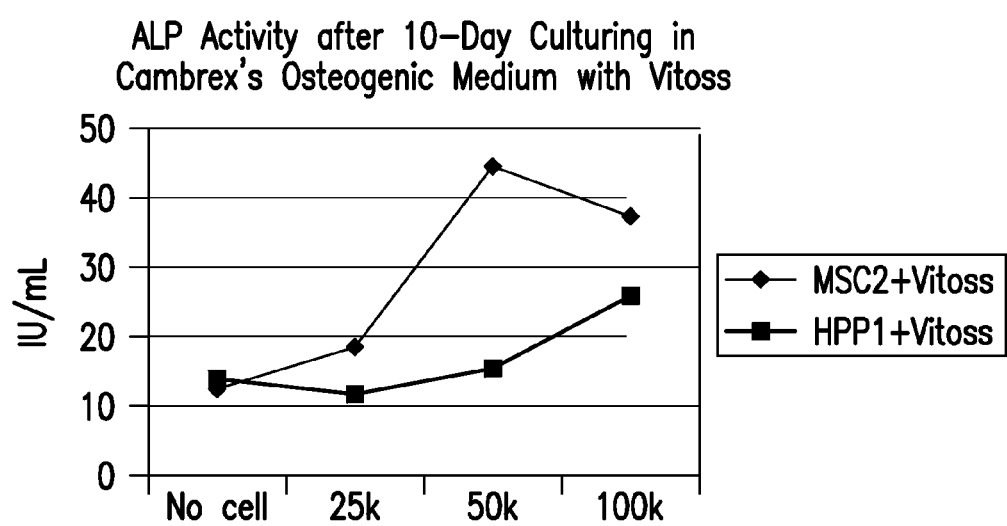

FIG. 21: AP activity of mesenchymal stem cells and stem cells following 10 days culturing in OS medium in the presence of a β-tricalcium phosphate substrate.

FIG. 22: Electromicrographs showing collagen fibrils (panel A) and mineralized collagen fibrils (panel B).

Figure 23:
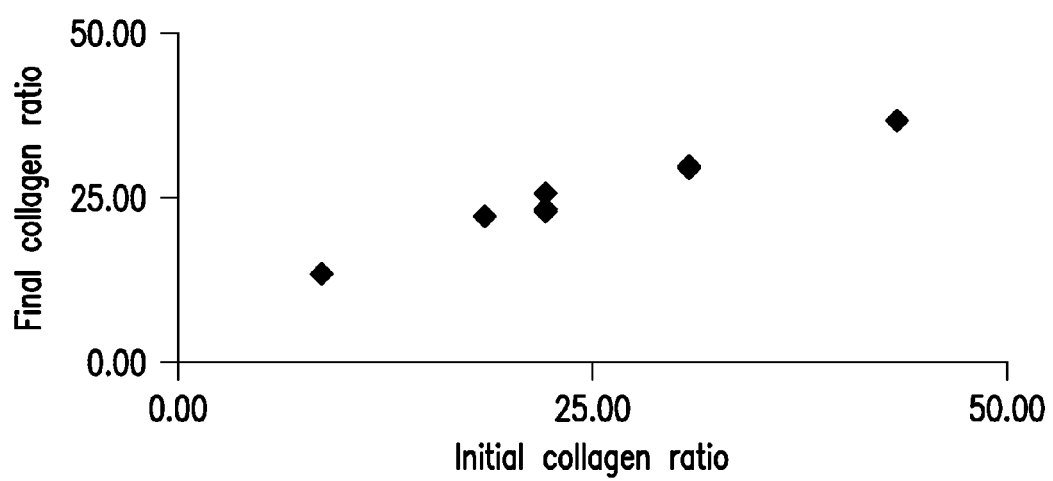

FIG. 23: Diagram showing that the final mineral/collagen ratio of crosslinked mineralized collagen was close to the input mineral/collagen ratio.

Figure 24:
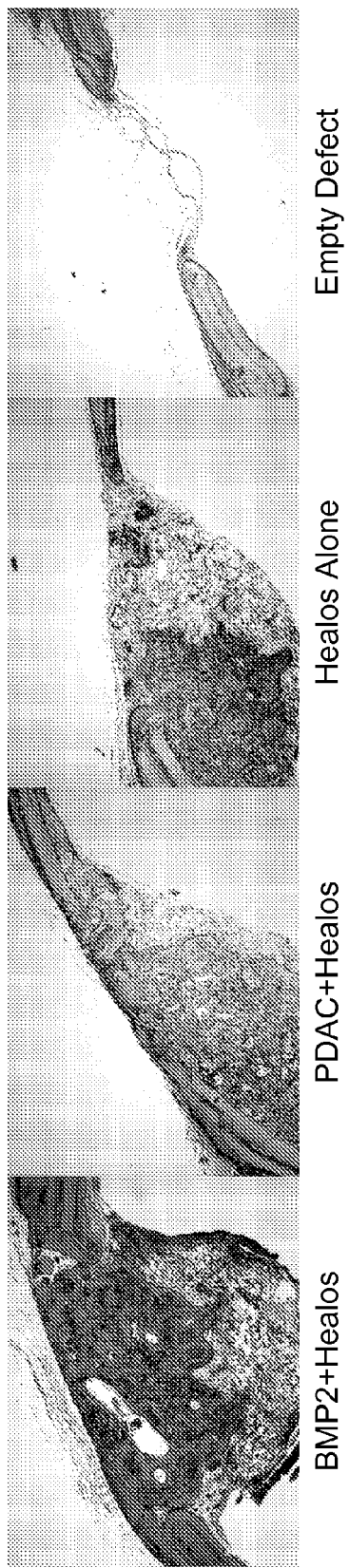

FIG. 24: Histological section of cranial defect 3 weeks post-implantation. Massive deposition of bond within the defect can be seen in the placental stem cell-HEALOS™ explant.

Figure 25A:
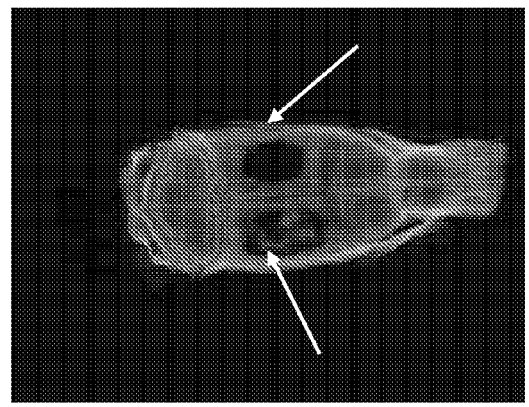
Figure 25B:
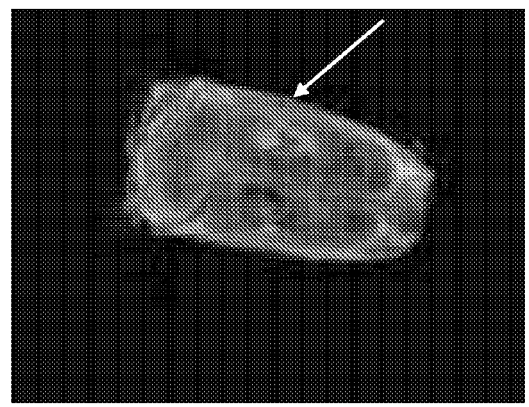
Figure 25C:
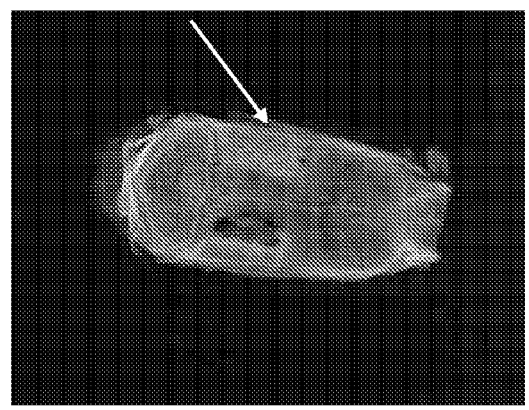

FIGS. 25A-25C: X-ray analysis of cranial defects at 7 weeks post-implantation. FIG. 25A: arrow indicates positive control explant BMP-2+HEALOS™. FIG. 25B: arrow indicates placental stem cell+HEALOS™ explant showing bone deposition. FIG. 25C: Negative controls HEALOS™ alone and cranial defect without explant.

Figure 26:
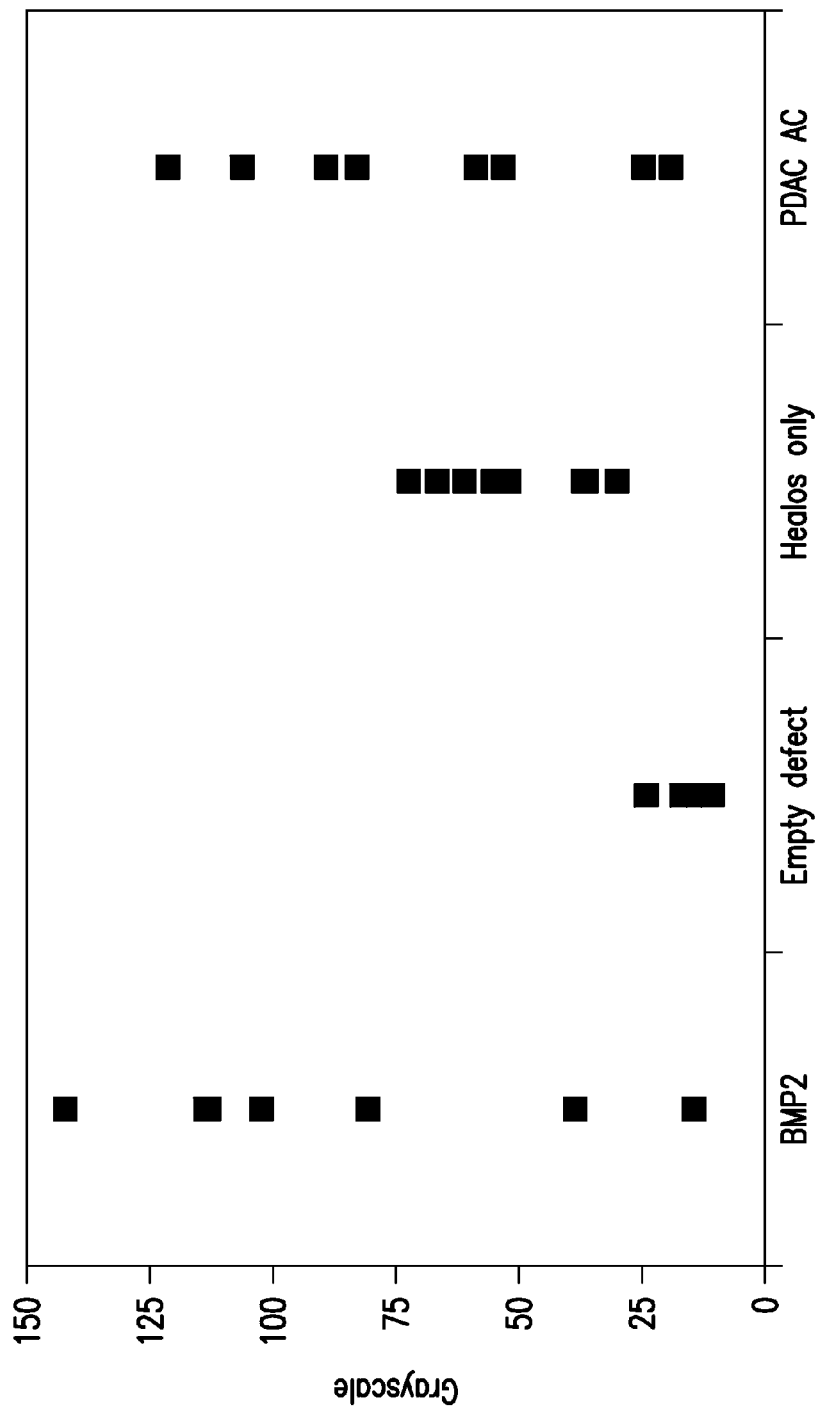

FIG. 26: Quantification of bone formation by densitometry. Increasing grayscale (Y axis) indicates increasing bone density/deposition. X axis: Treatment class.

5. DETAILED DESCRIPTION

5.1 Placental Stem Cells and Placental Stem Cell Populations

Placental stem cells are stem cells, obtainable from a placenta or part thereof, that adhere to a tissue culture substrate and have the capacity to differentiate into non-placental cell types. Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristic discussed below.

5.1.1 Physical and Morphological Characteristics

The nonadherent, $CD34^+$ stem cells provided herein, when cultured in primary cultures or in cell culture, do not typically adhere to the tissue culture substrate. The nonadherent stem cells in culture typically appear rounded, similar to $CD34^+$ stem cells from bone marrow or peripheral blood.

The adherent placental stem cells provided herein, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cyotplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

5.1.2 Cell Surface, Molecular and Genetic Markers

Nonadherent Placental Stem Cells: In one embodiment, provided herein is an isolated placental stem cell that is nonadherent. In certain embodiments, the isolated stem cell is $CD34^+$. In certain embodiments, the isolated stem cell is $CD44^-$. In certain embodiments, the isolated stem cell is $CD34^+$ and $CD44^-$. In certain embodiments, the isolated stem cell is $CD9^+$, $CD54^+$, $CD90^+$, or $CD166^+$. In certain embodiments, the isolated stem cell is $CD9^+$, $CD54^+$, $CD90^+$, and $CD166^+$. In certain embodiments, the isolated stem cell is $CD31^+$, $CD117^+$, $CD133^+$, or $CD200^+$. In certain embodiments, the isolated stem cell is $CD31^+$, $CD117^+$, $CD133^+$, and $CD200^+$. In certain embodiments, the isolated stem cell has been isolated from a human placenta by perfusion, or by physical or biochemical disruption of placental tissue, e.g., enzymatic digestion. In certain embodiments, the isolated stem cell has been isolated from a human placenta by perfusion. In certain embodiments, the isolated stem cell facilitates formation of a mineralized matrix in a population of placental cells when said population is cultured under conditions that allow the formation of a mineralized matrix.

In another embodiment, provided herein is a population of isolated placental cells that are nonadherent. In certain embodiments, the population comprises stem cells that are $CD34^+$. In certain embodiments, the population comprises nonadherent stem cells that are $CD44^-$. In certain embodiments, the population comprises stem cells that are $CD34^+$ and $CD44^-$. In certain embodiments, the population comprises stem cells that are $CD9^+$, $CD54^+$, $CD90^+$, or $CD166^+$. In certain embodiments, the population comprises stem cells that are $CD9^+$, $CD54^+$, $CD90^+$, and $CD166^+$. In certain embodiments, the population comprises stem cells that are $CD31^+$, $CD117^+$, $CD133^+$, or $CD200^+$. In certain embodiments, the population comprises stem cells that are $CD31^+$, $CD117^+$, $CD133^+$, and $CD200^+$. In certain embodiments, the population comprises stem cells, wherein at least about 70% of said cells are $CD34^+$ and $CD44^-$ stem cells. In certain embodiments, the population comprises stem cells, wherein at least about 90% of said cells are $CD34^+$ and $CD44^-$ stem cells.

In another aspect, provided herein is a population of isolated placental stem cells that are $CD34^+$ and $CD44^-$. In certain embodiments, the stem cells are $CD9^+$, $CD54^+$, $CD90^+$, or $CD166^+$. In certain embodiments, the stem cells are $CD9^+$, $CD54^+$, $CD90^+$, and $CD166^+$. In certain embodiments, the stem cells are $CD31^+$, $CD117^+$, $CD133^+$, or $CD200^+$. In certain embodiments, the stem cells are $CD31^+$, $CD117^+$, $CD133^+$, and $CD200^+$. In certain embodiments, at least about 70% of the stem cells are $CD34^+$ and $CD44^-$ stem cells. In certain embodiments, at least about 90% of the stem cells are CD34$^+$ and CD44$^-$ stem cells.

Adherent Placental Stem Cells: Adherent placental stem cells provided herein, and populations of placental stem cells, express a plurality of markers that can be used to identify and/or isolate the stem cells, or populations of cells that comprise the stem cells. The adherent placental stem cells, and stem cell populations provided herein (that is, two or more placental stem cells) include stem cells and stem cell-containing cell populations obtained directly from the placenta, or any part thereof (e.g., amnion, chorion, placental cotyledons, umbilical cord, and the like). Placental stem cell populations also includes populations of (that is, two or more) adherent placental stem cells in culture, and a population in a container, e.g., a bag. Placental stem cells are not, however, trophoblasts.

Adherent placental stem cells provided herein generally express the markers CD73, CD105, CD200, HLA-G, and/or OCT-4, and do not express CD34, CD38, or CD45. Placental stem cells can also express HLA-ABC (MHC-1) and HLA-DR. These markers can be used to identify placental stem cells, and to distinguish placental stem cells from other stem cell types. Because the placental stem cells can express CD73 and CD105, they can have mesenchymal stem cell-like characteristics. However, because the placental stem cells can express CD200 and HLA-G, a fetal-specific marker, they can be distinguished from mesenchymal stem cells, e.g., bone marrow-derived mesenchymal stem cells, which express neither CD200 nor HLA-G. In the same manner, the lack of expression of CD34, CD38 and/or CD45 identifies the placental stem cells as non-hematopoietic stem cells. However, certain subsets of placental stem cells can express, for example, CD34, and still be considered a placental stem cell as provided herein.

Thus, in one embodiment, provided herein is an isolated adherent placental stem cell that is CD200$^+$ or HLA-G$^+$. In a specific embodiment, said stem cell is a placental stem cell. In a specific embodiment, the stem cell is CD200$^+$ and HLA-G$^+$. In a specific embodiment, said stem cell is CD73$^+$ and CD105$^+$. In another specific embodiment, said stem cell is CD34$^-$, CD38$^-$ or CD45$^-$. In another specific embodiment, said stem cell is CD34$^-$, CD38$^-$ and CD45$^-$. In another specific embodiment, said stem cell is CD34$^-$, CD38$^-$, CD45$^-$, CD73$^+$ and CD105$^+$. In another specific embodiment, said CD200$^+$ or HLA-G$^+$ stem cell facilitates the formation of embryoid-like bodies in a population of placental cells comprising the stem cells, under conditions that allow the formation of embryoid-like bodies.

In another embodiment, also provided herein is a method of selecting a placental stem cell from a plurality of placental cells, comprising selecting a CD200 or HLA-G placental cell, whereby said cell is a placental stem cell. In a specific embodiment, said selecting comprises selecting a placental cell that is both CD200$^+$ and HLA-G$^+$. In a specific embodiment, said selecting comprises selecting a placental cell that is also CD73$^+$ and CD105$^+$. In another specific embodiment, said selecting comprises selecting a placental cell that is also CD34$^-$, CD38$^-$ or CD45$^-$. In another specific embodiment, said selecting comprises selecting a placental cell that is also CD34$^-$, CD38$^-$ and CD45$^-$. In another specific embodiment, said selecting comprises selecting a placental cell that is also CD34$^-$, CD38$^-$, CD45$^-$, CD73$^+$ and CD105$^+$. In another specific embodiment, said selecting comprises selecting a placental cell that also facilitates the formation of embryoid-like bodies in a population of placental cells comprising the stem cells, under conditions that allow the formation of embryoid-like bodies.

In another embodiment, provided herein is an isolated population of cells comprising isolated CD200$^+$, HLA-G$^+$ placental stem cells. In a specific embodiment, said population is a population of placental cells. In another specific embodiment, the population is a population of isolated CD200$^+$, HLA-G$^+$ placental stem cells. In various embodiments, at least about 10%, at least about 20%, at least about 30%, at least about 40%, at least about 50%, or at least about 60% of said cells are CD200$^+$, HLA-G$^+$ stem cells. Preferably, at least about 70% of said cells are CD200$^+$, HLA-G$^+$ stem cells. More preferably, at least about 90%, 95%, or 99% of said cells are CD200$^+$, HLA-G$^+$ stem cells. In a specific embodiment of the isolated populations, said stem cells are also CD73$^+$ and CD105$^+$. In another specific embodiment, said stem cells are also CD34$^-$, CD38$^-$ or CD45$^-$. In a more specific embodiment, said stem cells are also CD34$^-$, CD38$^-$, CD45$^-$, CD73$^+$ and CD105$^+$. In another embodiment, said isolated population produces one or more embryoid-like bodies when cultured under conditions that allow the formation of embryoid-like bodies.

In another embodiment, provided herein is a method of selecting a placental stem cell population from a plurality of placental cells, comprising selecting a population of placental cells wherein at least about 10%, at least about 20%, at least about 30%, at least about 40%, at least about 50% at least about 60%, at least about 70%, at least about 80%, at least about 90%, or at least about 95% of said cells are CD200$^+$, HLA-G$^+$ stem cells. In a specific embodiment, said selecting comprises selecting stem cells that are also CD73$^+$ and CD105$^+$. In another specific embodiment, said selecting comprises selecting stem cells that are also CD34$^-$, CD38$^-$ or CD45$^-$. In another specific embodiment, said selecting comprises selecting stem cells that are also CD34$^-$, CD38$^-$, CD45$^-$, CD73$^+$ and CD105$^+$. In another specific embodiment, said selecting also comprises selecting a population of placental stem cells that forms one or more embryoid-like bodies when cultured under conditions that allow the formation of embryoid-like bodies.

In another embodiment, provided herein is an isolated stem cell that is CD73$^+$, CD105$^+$, and CD200$^+$. In an specific embodiment, said isolated stem cell is an isolated adherent placental stem cell. In another specific embodiment, said stem cell is HLA-G$^+$. In another specific embodiment, said stem cell is CD34$^-$, CD38$^-$ or CD45$^-$. In another specific embodiment, said stem cell is CD34$^-$, CD38$^-$ and CD45$^-$. In a more specific embodiment, said stem cell is CD34$^-$, CD38$^-$, CD45$^-$, and HLA-G$^+$. In another specific embodiment, the isolated CD73$^+$, CD105$^+$, and CD200$^+$ stem cell facilitates the formation of one or more embryoid-like bodies in a population of placental cells comprising the stem cell, when the population is cultured under conditions that allow the formation of embryoid-like bodies.

In another embodiment, provided herein is provides a method of selecting a placental stem cell from a plurality of placental cells, comprising selecting a CD73$^+$, CD105$^+$, and CD200$^+$ placental cell, whereby said cell is a placental stem cell. In a specific embodiment, said selecting comprises selecting a placental cell that is also HLA-G$^+$. In another specific embodiment, said selecting comprises selecting a placental cell that is also CD34$^-$, CD38$^-$ or CD45$^-$. In another specific embodiment, said selecting comprises selecting a placental cell that is also CD34$^-$, CD38$^-$ and CD45$^-$. In another specific embodiment, said selecting comprises selecting a placental cell that is also CD34$^-$, CD38$^-$, CD45$^-$, and HLA-G$^+$. In another specific embodiment, said selecting additionally comprises selecting a CD73$^+$, CD105$^+$, and CD200$^+$ stem cell that facilitates the formation of one or more embryoid-like bodies in a population of placental cells comprising the stem cell, when the population is cultured under conditions that facilitate formation of embryoid-like bodies.

In another embodiment, provided herein is an isolated population of cells comprising $CD73^+$, $CD105^+$, $CD200^+$ stem cells. In a specific embodiment, said stem cells are placental stem cells. In another specific embodiment, the population is a population of $CD73^+$, $CD105^+$, $CD200^+$ isolated placental stem cells. In various embodiments, at least about 10%, at least about 20%, at least about 30%, at least about 40%, at least about 50%, or at least about 60% of said cells are $CD73^+$, $CD105^+$, $CD200^+$ stem cells. In another embodiment, at least about 70% of said cells in said population of cells are $CD73^+$, $CD105^+$, $CD200^+$ stem cells. In another embodiment, at least about 90%, 95% or 99% of said cells in said population of cells are $CD73^+$, $CD105^+$, $CD200^+$ stem cells. In a specific embodiment of said populations, said stem cells are $HLA-G^+$. In another specific embodiment, said stem cells are CD34, $CD38^-$ or $CD45^-$. In another specific embodiment, said stem cells are $CD34^-$, $CD38^-$ and $CD45^-$. In a more specific embodiment, said stem cells are $CD34^-$, $CD38^-$, $CD45^-$, and $HLA-G^+$. In another specific embodiment, said population of cells produces one or more embryoid-like bodies when cultured under conditions that allow the formation of embryoid-like bodies.

In another embodiment, provided herein is a method of selecting a placental stem cell population from a plurality of placental cells, comprising selecting a population of placental cells wherein at least about 10%, at least about 20%, at least about 30%, at least about 40%, at least about 50% at least about 60%, at least about 70%, at least about 80%, at least about 90%, or at least about 95% of said cells are $CD73^+$, $CD105^+$, $CD200^+$ stem cells. In a specific embodiment, said selecting comprises selecting stem cells that are also $HLA-G^+$. In another specific embodiment, said selecting comprises selecting stem cells that are also $CD34^-$, $CD38^-$ or $CD45^-$. In another specific embodiment, said selecting comprises selecting stem cells that are also $CD34^-$, $CD38^-$ and $CD45^-$. In another specific embodiment, said selecting comprises selecting stem cells that are also $CD34^-$, $CD38^-$, $CD45^-$, and $HLA-G^+$. In another specific embodiment, said selecting additionally comprises selecting a population of placental cells that produces one or more embryoid-like bodies when the population is cultured under conditions that allow the formation of embryoid-like bodies.

Also provided herein is an isolated stem cell that is $CD200^+$ and $OCT-4^+$. In a specific embodiment, the stem cell is $CD73^+$ and $CD105^+$. In a specific embodiment, the stem cell is a placental stem cell. In another specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, $CD45^-$, $CD73^+$, $CD105^+$ and $HLA-G^+$. In another specific embodiment, the stem cell facilitates the production of one or more embryoid-like bodies by a population of placental cells that comprises the stem cell, when the population is cultured under conditions that allow the formation of embryoid-like bodies.

In another embodiment, provided herein is a method of selecting a placental stem cell from a plurality of placental cells, comprising selecting a $CD200^+$ and $OCT-4^+$ placental cell, whereby said cell is a placental stem cell. In a specific embodiment, said selecting comprises selecting a placental cell that is also $HLA-G^+$. In another specific embodiment, said selecting comprises selecting a placental cell that is also $CD34^-$, $CD38^-$ or $CD45^-$. In another specific embodiment, said selecting comprises selecting a placental cell that is also $CD34^-$, $CD38^-$ and $CD45^-$. In another specific embodiment, said selecting comprises selecting a placental cell that is also $CD34^-$, $CD38^-$, $CD45^-$, $CD73^+$, $CD105^+$ and $HLA-G^+$. In another specific embodiment, said selecting comprises selecting a placental stem cell that also facilitates the production of one or more embryoid-like bodies by a population of placental cells that comprises the stem cell, when the population is cultured under conditions that allow the formation of embryoid-like bodies.

Also provided herein is an isolated population of cells comprising $CD200^+$, $OCT-4^+$ stem cells. In a specific embodiment, the stem cells are placental stem cells. In another specific embodiment, the population is a population of $CD200^+$, $OCT-4^+$ stem cells. In various embodiments, at least about 10%, at least about 20%, at least about 30%, at least about 40%, at least about 50%, or at least about 60% of said cells are $CD200^+$, $OCT-4^+$ stem cells. In another embodiment, at least about 70% of said cells are said $CD200^+$, $OCT-4^+$ stem cells. In another embodiment, at least about 90%, 95%, or 99% of said cells are said $CD200^+$, $OCT-4^+$ stem cells. In a specific embodiment of the isolated populations, said stem cells are $CD73^+$ and $CD105^+$. In another specific embodiment, said stem cells are $HLA-G^+$. In another specific embodiment, said stem cells are $CD34^-$, $CD38^-$ and $CD45^-$. In a more specific embodiment, said stem cells are $CD34^-$, $CD38^-$, $CD45^-$, $CD73^+$, $CD105^+$ and $HLA-G^+$. In another specific embodiment, the population produces one or more embryoid-like bodies when cultured under conditions that allow the formation of embryoid-like bodies.

In another embodiment, provided herein is a method of selecting a placental stem cell population from a plurality of placental cells, comprising selecting a population of placental cells wherein at least about 10%, at least about 20%, at least about 30%, at least about 40%, at least about 50% at least about 60%, at least about 70%, at least about 80%, at least about 90%, or at least about 95% of said cells are $CD200^+$, $OCT-4^+$ stem cells. In a specific embodiment, said selecting comprises selecting stem cells that are also $CD73^+$ and $CD105^+$. In another specific embodiment, said selecting comprises selecting stem cells that are also $HLA-G^+$. In another specific embodiment, said selecting comprises selecting stem cells that are also $CD34^-$, $CD38^-$ and $CD45^-$. In another specific embodiment, said stem cells are also $CD34^-$, $CD38^-$, $CD45^-$, $CD73^+$, $CD105^+$ and $HLA-G^+$.

Further provided herein is an isolated stem cell that is $CD73^+$, $CD105^+$ and $HLA-G^+$. In a specific embodiment, the stem cell is a placental stem cell. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $OCT-4^+$. In another specific embodiment, said stem cell is $CD200^+$. In a more specific embodiment, said stem cell is $CD34^-$, $CD38^-$, $CD45^-$, $OCT-4^+$ and $CD200^+$. In another specific embodiment, said stem cell facilitates the formation of embryoid-like bodies in a population of placental cells comprising said stem cell, when the population is cultured under conditions that allow the formation of embryoid-like bodies.

In another embodiment, also provided herein is a method of selecting a placental stem cell from a plurality of placental cells, comprising selecting a $CD73^+$, $CD105^+$ and $HLA-G^+$ placental cell, whereby said cell is a placental stem cell. In a specific embodiment, said selecting comprises selecting a placental cell that is also $CD34^-$, $CD38^-$ or $CD45^-$. In another specific embodiment, said selecting comprises selecting a placental cell that is also $CD34^-$, $CD38^-$ and $CD45^-$. In another specific embodiment, said selecting comprises selecting a placental cell that is also OCT-4$^+$. In another specific embodiment, said selecting comprises selecting a placental cell that is also CD200$^+$. In another specific embodiment, said selecting comprises selecting a placental cell that is also CD34$^-$, CD38$^-$, CD45$^-$, OCT-4$^+$ and CD200$^+$. In another specific embodiment, said selecting comprises selecting a placental cell that also facilitates the formation of one or more embryoid-like bodies in a population of placental cells that comprises said stem cell, when said population is culture under conditions that allow the formation of embryoid-like bodies.

Also provided herein is an isolated population of cells comprising CD73$^+$, CD105$^+$ and HLA-G$^+$ stem cells. In a specific embodiment, said stem cells are placental stem cells. In another specific embodiment, said population is a population of CD73$^+$, CD105$^+$ and HLA-G$^+$ stem cells. In various embodiments, at least about 10%, at least about 20%, at least about 30%, at least about 40%, at least about 50%, or at least about 60% of said cells are CD73$^+$, CD105$^+$ and HLA-G$^+$ stem cells. In another embodiment, at least about 70% of said cells are CD73$^+$, CD105$^+$ and HLA-G$^+$. In another embodiment, at least about 90%, 95% or 99% of said cells are CD73$^+$, CD105$^+$ and HLA-G$^+$ stem cells. In a specific embodiment of the above populations, said stem cells are CD34$^-$, CD38$^-$ or CD45$^-$. In another specific embodiment, said stem cells are CD34$^-$, CD38$^-$ and CD45$^-$. In another specific embodiment, said stem cells are OCT-4$^+$. In another specific embodiment, said stem cells are CD200$^+$. In a more specific embodiment, said stem cells are CD34$^-$, CD38$^-$, CD45$^-$, OCT-4$^+$ and CD200$^+$. In another embodiment, provided herein is a method of selecting a placental stem cell population from a plurality of placental cells, comprising selecting a population of placental cells wherein a majority of said cells are CD73$^+$, CD105$^+$ and HLA-G$^+$. In a specific embodiment, said majority of cells are also CD34$^-$, CD38$^-$ or CD45$^-$. In another specific embodiment, said majority of cells are also CD34$^-$, CD38$^-$ and CD45$^-$. In another specific embodiment, said majority of cells are also CD200$^+$. In another specific embodiment, said majority of cells are also CD34$^-$, CD38$^-$, CD45$^-$, OCT-4$^+$ and CD200$^+$.

In another embodiment, provided herein is an isolated stem cell that is CD73$^+$ and CD105$^+$ and which facilitates the formation of one or more embryoid-like bodies in a population of isolated placental cells comprising said stem cell when said population is cultured under conditions that allow formation of embryoid-like bodies. In a specific embodiment, said stem cell is CD34$^-$, CD38$^-$ or CD45$^-$. In another specific embodiment, said stem cell is CD34$^-$, CD38$^-$ and CD45$^-$. In another specific embodiment, said stem cell is OCT4$^+$. In a more specific embodiment, said stem cell is OCT4$^+$, CD34$^-$, CD38$^-$ and CD45$^-$.

Further provided herein is a population of isolated placental cells comprising CD73$^+$, CD105$^+$ stem cells, wherein said population forms one or more embryoid-like bodies under conditions that allow formation of embryoid-like bodies. In a specific embodiment, said stem cell is a placental stem cell. In another specific embodiment, said population is a population of placental stem cells that are CD73$^+$, CD105$^+$ stem cells, wherein said population forms one or more embryoid-like bodies under conditions that allow formation of embryoid-like bodies. In various embodiments, at least about 10%, at least about 20%, at least about 30%, at least about 40%, at least about 50% at least about 60%, at least about 70%, at least about 80%, at least about 90%, or at least about 95% of said isolated placental cells are CD73$^+$, CD105$^+$ stem cells. In a specific embodiment of the above populations, said stem cells are CD34$^-$, CD38$^-$ or CD45$^-$. In another specific embodiment, said stem cells are CD34$^-$, CD38$^-$ and CD45$^-$. In another specific embodiment, said stem cells are OCT-4$^+$. In a more specific embodiment, said stem cells are OCT-4$^+$, CD34$^-$, CD38$^-$ and CD45$^-$. In other specific embodiments, said population has been expanded, for example, has been passaged at least once, at least three times, at least five times, at least 10 times, at least 15 times, or at least 20 times.

Further provided herein is an isolated stem cell that is OCT-4$^+$ and which facilitates formation of one or more embryoid-like bodies in a population of isolated placental cells comprising said stem cell when cultured under conditions that allow formation of embryoid-like bodies. In a specific embodiment, said stem cell is CD73$^+$ and CD105$^+$. In another specific embodiment, said stem cell is CD34$^-$, CD38$^-$, or CD45$^-$. In another specific embodiment, said stem cell is CD200$^+$. In a more specific embodiment, said stem cell is CD73$^+$, CD105$^+$, CD200$^+$, CD34$^-$, CD38$^-$, and CD45$^-$.

Also provided herein is a population of isolated placental cells comprising OCT-4$^+$ stem cells, wherein said population forms one or more embryoid-like bodies when cultured under conditions that allow the formation of embryoid-like bodies. In a specific embodiment, the stem cells are placental stem cells. I another specific embodiment, said population is a population of placental stem cells that are OCT-4$^+$ stem cells, wherein said population forms one or more embryoid-like bodies when cultured under conditions that allow the formation of embryoid-like bodies. In various embodiments, at least about 10%, at least about 20%, at least about 30%, at least about 40%, at least about 50% at least about 60%, at least about 70%, at least about 80%, at least about 90%, or at least about 95% of said isolated placental cells are OCT4$^+$ stem cells. In a specific embodiment of the above populations, said stem cells are CD73$^+$ and CD105$^+$. In another specific embodiment, said stem cells are CD34$^-$, CD38$^-$, or CD45$^-$. In another specific embodiment, said stem cells are CD200$^+$. In a more specific embodiment, said stem cells are CD73$^+$, CD105$^+$, CD200$^+$, CD34$^-$, CD38$^-$, and CD45$^-$. In another specific embodiment, said population has been expanded, for example, passaged at least once, at least three times, at least five times, at least 10 times, at least 15 times, or at least 20 times.

Further provided herein are placental stem cells that are obtained by enzymatic digestion (see Section 5.2.3) or perfusion (see Section 5.2.4). For example, provided herein is an isolated population of placental stem cells that is produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises placental stem cells; and isolating a plurality of said placental stem cells from said population of cells. In a specific embodiment, the perfusion solution is passed through both the umbilical vein and umbilical arteries and collected after it exudes from the placenta. Populations of placental stem cells produced by this method typically comprise a mixture of fetal and maternal cells. In another specific embodiment, the perfusion solution is passed through the umbilical vein and collected from the umbilical arteries, or passed through the umbilical arteries and collected from the umbilical vein. Populations of placental stem cells produced by this method typically are substantially exclusively fetal in origin; that is, e.g., greater than 90%, 95%, 99%, or 99.5% of the placental stem cells in the population are fetal in origin.

In various embodiments, the placental stem cells, contained within a population of cells obtained from perfusion of a placenta, are at least about 50%, 60%, 70%, 80%, 90%, 95%, 99% or at least 99.5% of said population of placental cells. In another specific embodiment, the placental stem cells collected by perfusion comprise fetal and maternal cells. In another specific embodiment, the placental stem cells collected by perfusion are at least about 50%, 60%, 70%, 80%, 90%, 95%, 99% or at least 99.5% fetal cells.

In another specific embodiment, provided herein is a composition comprising a population of isolated placental stem cells collected by perfusion, wherein said composition comprises at least a portion of the perfusion solution used to collect the placental stem cells.

Further provided herein is an isolated population of the placental stem cells described herein that is produced according to a method comprising digesting placental tissue with a tissue-disrupting enzyme to obtain a population of placental cells comprising placental stem cells, and isolating a plurality of placental stem cells from the remainder of said placental cells. The whole, or any part of, the placenta can be digested to obtain placental stem cells. In specific embodiments, for example, said placental tissue is a whole placenta, an amniotic membrane, chorion, a combination of amnion and chorion, or a combination of any of the foregoing. In other specific embodiment, the tissue-disrupting enzyme is trypsin or collagenase. In various embodiments, the placental stem cells, contained within a population of cells obtained from digesting a placenta, are at least about 50%, 60%, 70%, 80%, 90%, 95%, 99% or at least 99.5% of said population of placental cells.

Gene profiling confirms that isolated adherent placental stem cells, and populations of isolated placental stem cells, are distinguishable from other cells, e.g., mesenchymal stem cells, e.g., bone marrow-derived stem cells. The adherent placental stem cells described herein, can be distinguished from mesenchymal stem cells on the basis of the expression of one or more genes, the expression of which is specific to placental stem cells or umbilical cord stem cells in comparison to bone marrow-derived mesenchymal stem cells. In particular, adherent placental stem cells can be distinguished from mesenchymal stem cells on the basis of the expression of one or more gene, the expression of which is significantly higher (that is, at least twofold higher) in placental stem cells than in mesenchymal stem cells, wherein the one or more gene is(are) ACTG2, ADARB1, AMIGO2, ATRS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, ZC3H12A, or a combination of any of the foregoing, wherein the expression of these genes is higher in placental stem cells or umbilical cord stem cells than in bone marrow-derived stem cells, when the stem cells are grown under equivalent conditions. In a specific embodiment, the placental stem cell-specific or umbilical cord stem cell-specific gene is CD200.

The level of expression of these genes can be used to confirm the identity of a population of placental cells, to identify a population of cells as comprising at least a plurality of placental stem cells, or the like. The population of placental stem cells, the identity of which is confirmed, can be clonal, e.g., a population of placental stem cells expanded form a single placental stem cell, or a mixed population of stem cells, e.g., a population of cells comprising solely placental stem cells that are expanded from multiple placental stem cells, or a population of cells comprising placental stem cells and at least one other type of cell.

The level of expression of these genes can be used to select populations of adherent placental stem cells. For example, a population of cells, e.g., clonally-expanded cells, is selected if the expression of one or more of these genes is significantly higher in a sample from the population of cells than in an equivalent population of mesenchymal stem cells. Such selecting can be of a population from a plurality of placental stem cells populations, from a plurality of cell populations, the identity of which is not known, etc.

Adherent placental stem cells can be selected on the basis of the level of expression of one or more such genes as compared to the level of expression in said one or more genes in a mesenchymal stem cell control. In one embodiment, the level of expression of said one or more genes in a sample comprising an equivalent number of mesenchymal stem cells is used as a control. In another embodiment, the control, for placental stem cells tested under certain conditions, is a numeric value representing the level of expression of said one or more genes in mesenchymal stem cells under said conditions.

The isolated populations of adherent or nonadherent placental stem cells described above, and populations of placental stem cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

5.1.3 Growth in Culture

The growth of the placental stem cells described herein, as for any mammalian cell, depends in part upon the particular medium selected for growth. Under optimum conditions, placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated adherent placental cells that comprise the placental stem cells provided herein, when cultured under appropriate conditions, form embryoid-like bodies, that is, three-dimensional clusters of cells grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental stem cells thus facilitate the growth of one or more embryoid-like bodies in a population of placental cells that comprise the adherent placental stem cells. Without wishing to be bound by theory, the cells of the embryoid-like bodies are thought to grow on the adherent placental stem cells much as embryonic stem cells grow on a feeder layer of cells. Mesenchymal stem cells, e.g., bone marrow-derived mesenchymal stem cells, do not develop embryoid-like bodies in culture.

5.2 Methods of Obtaining Placental Stem Cells 5.2.1 Stem Cell Collection Composition Further provided herein are methods of collecting and isolating placental stem cells. Generally, stem cells are obtained from a mammalian placenta using a physiologically-acceptable solution, e.g., a stem cell collection composition. A stem cell collection composition is described in detail in related U.S. Provisional Application No. 60/754,969, entitled "Improved Medium for Collecting Placental Stem Cells and Preserving Organs," filed on Dec. 29, 2005.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.2.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental stem cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.2.3 Physical Disruption and Enzymatic Digestion of Placental Tissue

In one embodiment, stem cells are collected from a mammalian placenta by physical disruption, e.g., enzymatic digestion, of the organ. For example, the placenta, or a portion thereof, may be, e.g., crushed, sheared, minced, diced, chopped, macerated or the like, while in contact with the stem cell collection composition provided herein, and the tissue subsequently digested with one or more enzymes. The placenta, or a portion thereof, may also be physically disrupted and digested with one or more enzymes, and the resulting material then immersed in, or mixed into, the stem cell collection composition. Any method of physical disruption can be used, provided that the method of disruption leaves a plurality, more preferably a majority, and more preferably at least about 60%, 70%, 80%, 90%, 95%, 98%, or 99% of the cells in said organ viable, as determined by, e.g., trypan blue exclusion.

The placenta can be dissected into components prior to physical disruption and/or enzymatic digestion and stem cell recovery. For example, placental stem cells can be obtained from the amniotic membrane, chorion, umbilical cord, placental cotyledons, or any combination thereof. Preferably, placental stem cells are obtained from placental tissue comprising amnion and chorion. Typically, placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred stem cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

It will be appreciated that where an entire placenta, or portion of a placenta comprising both fetal and maternal cells (for example, where the portion of the placenta comprises the chorion or cotyledons), the placental stem cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

5.2.4 Placental Perfusion

Placental stem cells can also be obtained by perfusion of the mammalian placenta. Methods of perfusing mammalian placenta to obtain stem cells are disclosed, e.g., in Hariri, U.S. Application Publication No. 2002/0123141, and in related U.S. Provisional Application No. 60/754,969, entitled "Improved Medium for Collecting Placental Stem Cells and Preserving Organs," filed on Dec. 29, 2005.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature in the closed circuit method, whereby perfusion fluid is passed through one or two placental vessels and is collected solely through the remaining vessel(s), results in the collection of a population of placental stem cells almost exclusively of fetal origin.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental stem cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion according to the methods provided herein results in the collection of significantly more placental stem cells than the number obtainable from a mammalian placenta not perfused with said solution, and not otherwise treated to obtain stem cells (e.g., by tissue disruption, e.g., enzymatic digestion). In this context, "significantly more" means at least about 10% more. Perfusion yields significantly more placental stem cells than, e.g., the number of placental stem cells obtainable from culture medium in which a placenta, or portion thereof, has been cultured.

Stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition provided herein.

5.2.5 Placental Perfusate and Placental Perfusate Cells

Placental perfusate, and placental perfusate cells, e.g., total nucleated cells isolated from placental perfusate, comprise a heterogeneous collection of cells. Typically, placental perfusate, and placental perfusate cells, are depleted of erythrocytes prior to use. Such depletion can be carried out by known methods of separating red blood cells from nucleated blood cells. In certain embodiment, the placental perfusate or perfusate cells are cryopreserved. In certain other embodiments, the placental perfusate comprises, or the perfusate cells comprise, only fetal cells, or a combination of fetal cells and maternal cells.

Typically, placental perfusate from a single placental perfusion comprises about 100 million to about 500 million nucleated cells. In certain embodiments, the placental perfusate or perfusate cells comprise $CD34^+$ cells, e.g., hematopoietic stem or progenitor cells. Such cells can, in a more specific embodiment, comprise $CD34^+$ $CD45^-$ stem or progenitor cells, $CD34^+$ $CD45^+$ stem or progenitor cells, myeloid progenitors, lymphoid progenitors, and/or erythroid progenitors. In other embodiments, placental perfusate and placental perfusate cells comprise adherent placental stem cells, e.g., $CD34^-$ stem cells, e.g., adherent placental stem cells as described in Section 5.1, above. In other embodiment, the placental perfusate and placental perfusate cells comprise, e.g., endothelial progenitor cells, osteoprogenitor cells, and natural killer cells. In certain embodiments, placental perfusate as collected from the placenta and depleted of erythrocytes, or perfusate cells isolated from such perfusate, comprise about 6-7% natural killer cells ($CD3^-$, $CD56^+$); about 21-22% T cells ($CD3^+$); about 6-7% B cells ($CD19^+$); about 1-2% endothelial progenitor cells ($CD34^+$, $CD31^+$); about 2-3% neural progenitor cells ($nestin^+$); about 2-5% hematopoietic progenitor cells ($CD34^+$); and about 0.5-1.5% adherent placental stem cells (e.g., $CD34^-$, $CD17^-$, $CD105^+$ and $CD44^+$), as determined, e.g. by flow cytometry, e.g., by FACS analysis.

The $CD34^+$ stem or progenitor cells in human placental perfusate express detectably higher levels of angiogenesis-related markers, e.g., CD31, VEGF-R and/or CXCR4 than do an equivalent number of $CD34^+$ cells isolated from umbilical cord blood. In certain embodiments, human placental perfusate mononuclear cells from a single perfusion that are cultured in ENDOCULT® medium with VEGF (for growth of CFU-Hill colonies; StemCell Technologies, Inc.) generate up to about 20, e.g., about 1, 2, 3, 4, 5, 6, 7, 8, 9, 10, 11, 12, 13, 14, 15, 16, 17, 18, 19 or 20 CFU-Hill colonies (endothelial cell progenitors). Development of CFU-Hill colonies in liquid culture can be demonstrated and assessed, e.g., by measuring uptake of diacetylated low density lipoprotein (Dil-acLDL) by endothelial progenitor cells obtained from human placental perfusate at, e.g., seven days of culture in ENDOCULT® medium.

Moreover, $CD34^+$ $CD45^-$ cells from human placental perfusate have a detectably higher expression of angiogenesis related markers CD31 and/or VEGFR than $CD34^+$ $CD45^+$ cells.

Typically, placental perfusate and perfusate cells have low expression of MHC class I compared to umbilical cord blood cells, and are largely negative for MHC class II markers.

5.2.6 Isolation, Sorting, and Characterization of Placental Stem Cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means to remove at least about 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about $5-10\times10^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is CD34+. Likewise, if a cell produces enough OCT-4 RNA to be detectable by RT-PCR, or significantly more OCT-4 RNA than an adult cell, the cell is OCT-4+ Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers CD34, CD38, CD44, CD45, CD73, CD105, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; CD34− cells are retained, and cells that are CD200+ HLA-G+, are separated from all other CD34− cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are CD200+, HLA-G+, CD73+, CD105+, CD34−, CD38− and CD45− are isolated from other placental cells for further use.

In another embodiment, magnetic beads can be used to separate cells. The cells may be sorted using a magnetic activated cell sorting (MACS) technique, a method for separating particles based on their ability to bind magnetic beads (0.5-100 µm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4+ placental cells that produce one or more embryoid-like bodies in culture are isolated from other placental cells.

In another embodiment, placental stem cells can be identified and characterized by a colony forming unit assay. Colony forming unit assays are commonly known in the art, such as MESEN CULT™ medium (Stem Cell Technologies, Inc., Vancouver British Columbia)

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.3 Culture of Placental Stem Cells

5.3.1 Culture Media

Isolated placental stem cells, or placental stem cell population, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GLUTAMAX™ and gentamicin; DMEM comprising 10% FBS, GLUTAMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Placental stem cells can be cultured in standard tissue culture conditions, e.g., in tissue culture dishes or multiwell plates. Placental stem cells can also be cultured using a hanging drop method. In this method, placental stem cells are suspended at about $1 \times 10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

5.3.2 Expansion and Proliferation of Placental Stem Cells

Once an isolated placental stem cell, or isolated population of stem cells (e.g., a stem cell or population of stem cells separated from at least about 50% of the placental cells with which the stem cell or population of stem cells is normally associated in vivo), the stem cell or population of stem cells can be proliferated and expanded in vitro. For example, a population of placental stem cells can be cultured in tissue culture containers, e.g., dishes, flasks, multiwell plates, or the like, for a sufficient time for the stem cells to proliferate to 70-90% confluence, that is, until the stem cells and their progeny occupy 70-90% of the culturing surface area of the tissue culture container.

Placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells preferably are grown under low oxidative stress (e.g., with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium. Typically, the new medium is the same type of medium from which the stem cells were removed. Provided herein are populations of placental stem cells that have been passaged at least 1, 2, 3, 4, 5, 6, 7, 8, 9, 10, 12, 14, 16, 18, or 20 times, or more.

5.3.3 Placental Stem Cell Populations

Further provided herein are populations of placental stem cells. Placental stem cell population can be isolated directly from one or more placentas; that is, the placental stem cell population can be a population of placental cells, comprising placental stem cells, obtained from, or contained within, perfusate, or obtained from, or contained within, digestate (that is, the collection of cells obtained by enzymatic digestion of a placenta or part thereof). Isolated placental stem cells provided herein can also be cultured and expanded to produce placental stem cell populations. Populations of placental cells comprising placental stem cells can also be cultured and expanded to produce placental stem cell populations.

Placental stem cell populations provided herein comprise placental stem cells, for example, placental stem cells as described herein. In various embodiments, at least about 10%, 20%, 30%, 40%, 50%, 60%, 70%, 80%, 90%, 95%, or 99% of the cells in an isolated placental stem cell population are placental stem cells. That is, a placental stem cell population can comprise, e.g., as much as 1%, 5%, 10%, 20%, 30%, 40%, 50%, 60%, 70%, 80%, 90% non-stem cells.

Provided herein are methods of producing isolated placental stem cell population by, e.g., selecting placental stem cells, whether derived from enzymatic digestion or perfusion, that express particular markers and/or particular culture or morphological characteristics. In one embodiment, for example, provided herein is a method of producing a cell population comprising selecting placental cells that (a) adhere to a substrate, and (b) express CD200 and HLA-G; and isolating said cells from other cells to form a cell population. In another embodiment, the method of producing a cell population comprises selecting placental cells that (a) adhere to a substrate, and (b) express CD73, CD105, and CD200; and isolating said cells from other cells to form a cell population. In another embodiment, the method of producing a cell population comprises selecting placental cells that (a) adhere to a substrate and (b) express CD200 and OCT-4; and isolating said cells from other cells to form a cell population. In another embodiment, the method of producing a cell population comprises selecting placental cells that (a) adhere to a substrate, (b) express CD73 and CD105, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, the method of producing a cell population comprises selecting placental cells that (a) adhere to a substrate, and (b) express CD73, CD105 and HLA-G; and isolating said cells from other cells to form a cell population. In another embodiment, the method of producing a cell population comprises selecting placental cells that (a) adhere to a substrate, (b) express OCT-4, and (c) facilitate the formation of one or more embryoid-like bodies in a population of placental cells comprising said stem cell when said population is cultured under conditions that allow for the formation of an embryoid-like body; and isolating said cells from other cells to form a cell population. In any of the above embodiments, the method can additionally comprise selecting placental cells that express ABC-p (a placenta-specific ABC transporter protein; see, e.g., Allikmets et al., *Cancer Res.* 58(23):5337-9 (1998)). The method can also comprise selecting cells exhibiting at least one characteristic specific to, e.g., a mesenchymal stem cell, for example, expression of CD29, expression of CD44, expression of CD90, or expression of a combination of the foregoing.

In the above embodiments, the substrate can be any surface on which culture and/or selection of cells, e.g., placental stem cells, can be accomplished. Typically, the substrate is plastic, e.g., tissue culture dish or multiwell plate plastic. Tissue culture plastic can be coated with a biomolecule, e.g., laminin or fibronectin.

Cells, e.g., placental stem cells, can be selected for a placental stem cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental stem cell population can comprise placental cells that are not stem cells, or cells that are not placental cells.

Isolated placental stem cell populations can be combined with one or more populations of non-stem cells or non-placental cells. For example, an isolated population of placental stem cells can be combined with blood (e.g., placental blood or umbilical cord blood), blood-derived stem cells (e.g., stem cells derived from placental blood or umbilical cord blood), populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. Cells in an isolated placental stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental stem cell population can be combined with a plurality of cells of a plurality of cell types, as well.

In one, an isolated population of placental stem cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

5.4 Combinations of Placental Stem Cells and Placental Perfusate or Placental Perfusate Cells Provided herein are combinations of placental perfusate with isolated placental perfusate cells and/or the placental stem cells provided. Herein, the placental stem cells can be $CD34^+$ placental stem cells, $CD34^-$ placental stem cells, or a combination thereof. In one embodiment, for example, provided herein is a volume of placental perfusate supplemented with a plurality of placental perfusate cells and/or a plurality of placental stem cells. In specific embodiments, for example, each milliliter of placental perfusate is supplemented with about $1\times10^4$, $5\times10^4$, $1\times10^5$, $5\times10^5$, $1\times10^6$, $5\times10^6$ or more placental perfusate cells or placental stem cells. In another embodiment, a plurality of placental perfusate cells is supplemented with placental perfusate and/or placental stem cells. In another embodiment, a plurality of placental stem cells is supplemented with placental perfusate and/or a plurality of placental perfusate cells. In certain embodiments, when perfusate is used for supplementation, the volume of perfusate is about, greater than about, or less than about, 50%, 45%, 40%, 35%, 30%, 25%, 20%, 15%, 10%, 8%, 6%, 4%, 2% or 1% of the total volume of cells (in solution) plus perfusate. When placental perfusate cells are used to supplement a plurality of placental stem cells, the placental perfusate cells generally comprise about, greater than about, or fewer than about, 50%, 45%, 40%, 35%, 30%, 25%, 20%, 15%, 10%, 8%, 6%, 4%, 2% or 1% of the total number of placental perfusate cells plus placental stem cells. Similarly, when placental stem cells are used to supplement a plurality of placental perfusate cells, the placental stem cells generally comprise about, greater than about, or fewer than about, 50%, 45%, 40%, 35%, 30%, 25%, 20%, 15%, 10%, 8%, 6%, 4%, 2% or 1% of the total number of placental perfusate cells plus placental stem cells. When placental stem cells or placental perfusate cells are used to supplement placental perfusate, the volume of solution (e.g., saline solution, culture medium or the like) in which the cells are suspended comprises about, greater than about, or less than about, 50%, 45%, 40%, 35%, 30%, 25%, 20%, 15%, 10%, 8%, 6%, 4%, 2% or 1% of the total volume of perfusate plus cells, where the placental stem cells are suspended to about $1\times10^4$, $5\times10^4$, $1\times10^5$, $5\times10^5$, $1\times10^6$, $5\times10^6$, $1\times10^7$, $5\times10^7$, $1\times10^8$, $5\times10^8$ or more cells per milliliter prior to supplementation.

Further provided herein is pooled placental perfusate that is obtained from two or more sources, e.g., two or more placentas, and combined, e.g., pooled. Such pooled perfusate can comprise approximately equal volumes of perfusate from each source, or can comprise different volumes from each source. The relative volumes from each source can be randomly selected, or can be based upon, e.g., a concentration or amount of one or more cellular factors, e.g., cytokines, growth factors, hormones, or the like; the number of placental cells in perfusate from each source; or other characteristics of the perfusate from each source. Perfusate from multiple perfusions of the same placenta can similarly be pooled.

Similarly, provided herein are placental perfusate cells, and placental stem cells, that are obtained from two or more sources, e.g., two or more placentas, and pooled. Such pooled cells can comprise approximately equal numbers of cells from the two or more sources, or different numbers of cells from one or more of the pooled sources. The relative numbers of cells from each source can be selected based on, e.g., the number of one or more specific cell types in the cells to be pooled, e.g., the number of CD34⁻ stem cells, etc.

Pools can comprise, e.g., placental perfusate supplemented with placental perfusate cells; placental perfusate supplemented with placental stem cells; placental perfusate supplemented with both placental perfusate cells and placental stem cells; placental perfusate cells supplemented with placental perfusate; placental perfusate cells supplemented with placental stem cells; placental perfusate cells supplemented with both placental perfusate and placental stem cells; placental stem cells supplemented with placental perfusate; placental stem cells supplemented with placental perfusate cells; or placental stem cells supplemented with both placental perfusate cells and placental perfusate.

In certain embodiments, placental perfusate, placental perfusate cells, and placental stem cells are provided as pharmaceutical grade administrable units. Such units can be provided in discrete volumes, e.g., 100 mL, 150 mL, 200 mL, 250 mL, 300 mL, 350 mL, 400 mL, 450 mL, 500 mL, or the like. Such units can be provided so as to contain a specified number of, e.g., placental perfusate cells, placental perfusate-derived intermediate natural killer cells, or both, e.g., $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$ or more cells per milliliter, or $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more cells per unit. Such units can be provided to contain specified numbers of any two, or all three, of placental perfusate, placental perfusate cells, and/or placental stem cells.

In the above combinations of placental perfusate, placental perfusate cells and/or placental stem cells, any one, any two, or all three of the placental perfusate, placental perfusate cells and/or placental stem cells can be autologous to a recipient (that is, obtained from the recipient), or homologous to a recipient (that is, obtained from at last one other individual from said recipient).

Also provided herein are compositions comprising placental stem cells in combination with placental perfusate cells and/or placental perfusate. Thus, in another aspect, provided herein is a composition comprising isolated placental stem cells, wherein said placental stem are isolated from placental perfusate, and wherein said placental stem cells comprise at least 50% of cells in the composition. In a specific embodiment, said placental stem cells comprise at least 80% of cells in the composition. In another specific embodiment, the composition comprises isolated placental perfusate. In a more specific embodiment, said placental perfusate is from the same individual as said placental stem cells. In another more specific embodiment, said placental perfusate comprises placental perfusate from a different individual than said placental stem cells. In another specific embodiment, the composition comprises placental perfusate cells. In a more specific embodiment, said placental perfusate cells are from the same individual as said placental stem cells. In another more specific embodiment, said placental perfusate cells are from a different individual than said placental stem cells. In another specific embodiment, the composition additionally comprises isolated placental perfusate and isolated placental perfusate cells, wherein said isolated perfusate and said isolated placental perfusate cells are from different individuals. In another more specific embodiment of any of the above embodiments comprising placental perfusate, said placental perfusate comprises placental perfusate from at least two individuals. In another more specific embodiment of any of the above embodiments comprising placental perfusate cells, said isolated placental perfusate cells are from at least two individuals.

5.5 Production of a Placental Stem Cell Bank

Stem cells from postpartum placentas can be cultured in a number of different ways to produce a set of lots, e.g., a set of individually-administrable doses, of placental stem cells. Such lots can, for example, be obtained from stem cells from placental perfusate or from enzyme-digested placental tissue. Sets of lots of placental stem cells, obtained from a plurality of placentas, can be arranged in a bank of placental stem cells for, e.g., long-term storage. Generally, adherent stem cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, stem cell lots are obtained as follows. Placental tissue is first disrupted, e.g., by mincing, digested with a suitable enzyme, e.g., collagenase (see Section 5.2.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and defined as Passage 0 cells.

Passage 0 cells are then used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$ or $10 \times 10^4$ stem cells. Preferably, from about $2 \times 10^4$ to about $3 \times 10^4$ Passage 0 cells are used to seed each expansion culture. The number of expansion cultures can depend upon the number of Passage 0 cells, and may be greater or fewer in number depending upon the particular placenta(s) from which the stem cells are obtained.

Expansion cultures are grown until the density of cells in culture reaches a certain value, e.g., about $1 \times 10^5$ cells/cm². Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30, preferably about 20 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 100 million cells per ml, and can comprise between about $10^6$ and about $10^9$ cells in total.

In a specific embodiment, of the method, Passage 0 cells are cultured for approximately 4 doublings, then frozen in a first cell bank. Cells from the first cell bank are frozen and used to seed a second cell bank, the cells of which are expanded for about another eight doublings. Cells at this stage are collected and frozen and used to seed new expansion cultures that are allowed to proceed for about eight additional doublings, bringing the cumulative number of cell doublings to about 20. Cells at the intermediate points in passaging can be frozen in units of about 100,000 to about 10 million cells per ml, preferably about 1 million cells per ml for use in subsequent expansion culture. Cells at about 20 doublings can be frozen in individual doses of between about 1 million to about 100 million cells per ml for administration or use in making a stem cell-containing composition.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental stem cell lots, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.6 Differentiation of Adherent Placental Stem Cells

5.6.1 Induction of Differentiation into Neuronal or Neurogenic Cells

Neuronal differentiation of placental stem cells can be accomplished, for example, by placing placental stem cells in cell culture conditions that induce differentiation into neurons. In an example method, a neurogenic medium comprises DMEM/20% FBS and 1 mM beta-mercaptoethanol; such medium can be replaced after culture for about 24 hours with medium consisting of DMEM and 1-10 mM betamercaptoethanol. In another embodiment, the cells are contacted with DMEM/2% DMSO/200 μM butylated hydroxyanisole. In a specific embodiment, the differentiation medium comprises serum-free DMEM F-12, butylated hydroxyanisole, potassium chloride, insulin, forskolin, valproic acid, and hydrocortisone. In another embodiment, neuronal differentiation is accomplished by plating placental stem cells on laminin-coated plates in Neurobasal-A medium (Invitrogen, Carlsbad Calif.) containing B27 supplement and L-glutamine, optionally supplemented with bFGF and/or EGF. Placental stem cells can also be induced to neural differentiation by co-culture with neural cells, or culture in neuron-conditioned medium.

Neuronal differentiation can be assessed, e.g., by detection of neuron-like morphology (e.g., bipolar cells comprising extended processes) detection of the expression of e.g., nerve growth factor receptor and neurofilament heavy chain genes by RT/PCR; or detection of electrical activity, e.g., by patch-clamp.

5.6.2 Induction of Differentiation into Adipogenic Cells

Adipogenic differentiation of placental stem cells can be accomplished, for example, by placing placental stem cells in cell culture conditions that induce differentiation into adipocytes. A preferred adipogenic medium comprises MSCGM (Cambrex) or DMEM supplemented with 15% cord blood serum. In one embodiment, placental stem cells are fed Adipogenesis Induction Medium (Cambrex) and cultured for 3 days (at 37° C., 5% $CO_2$), followed by 1-3 days of culture in Adipogenesis Maintenance Medium (Cambrex). After 3 complete cycles of induction/maintenance, the cells are cultured for an additional 7 days in adipogenesis maintenance medium, replacing the medium every 2-3 days.

In another embodiment, placental stem cells are cultured in medium comprising 1 μM dexamethasone, 0.2 mM indomethacin, 0.01 mg/ml insulin, 0.5 mM IBMX, DMEM-high glucose, FBS, and antibiotics. Placental stem cells can also be induced towards adipogenesis by culture in medium comprising one or more glucocorticoids (e.g., dexamethasone, indomethasone, hydrocortisone, cortisone), insulin, a compound which elevates intracellular levels of cAMP (e.g., dibutyryl-cAMP; 8-CPT-cAMP (8-(4)chlorophenylthio)-adenosine, 3',5' cyclic monophosphate); 8-bromo-cAMP; dioctanoyl-cAMP; forskolin) and/or a compound which inhibits degradation of cAMP (e.g., a phosphodiesterase inhibitor such as isobutylmethylxanthine (IBMX), methyl isobutylxanthine, theophylline, caffeine, indomethacin).

A hallmark of adipogenesis is the development of multiple intracytoplasmic lipid vesicles that can be easily observed using the lipophilic stain oil red O. Expression of lipase and/or fatty acid binding protein genes is confirmed by RT/PCR in placental stem cells that have begun to differentiate into adipocytes.

5.6.3 Induction of Differentiation into Chondrocytic Cells

Chondrogenic differentiation of placental stem cells can be accomplished, for example, by placing placental stem cells in cell culture conditions that induce differentiation into chondrocytes. A preferred chondrocytic medium comprises MSCGM (Cambrex) or DMEM supplemented with 15% cord blood serum. In one embodiment, placental stem cells are aliquoted into a sterile polypropylene tube, centrifuged (e.g., at 150×g for 5 minutes), and washed twice in Incomplete Chondrogenesis Medium (Cambrex). The cells are resuspended in Complete Chondrogenesis Medium (Cambrex) containing 0.01 μg/ml TGF-beta-3 at a concentration of about $1-20\times10^5$ cells/ml. In other embodiments, placental stem cells are contacted with exogenous growth factors, e.g., GDF-5 or transforming growth factor beta3 (TGF-beta3), with or without ascorbate. Chondrogenic medium can be supplemented with amino acids including proline and glutamine, sodium pyruvate, dexamethasone, ascorbic acid, and insulin/transferrin/selenium. Chondrogenic medium can be supplemented with sodium hydroxide and/or collagen. The placental stem cells may be cultured at high or low density. Cells are preferably cultured in the absence of serum.

Chondrogenesis can be assessed by e.g., observation of production of esoinophilic ground substance, safranin-O staining for glycosaminoglycan expression; hematoxylin/eosin staining, assessing cell morphology, and/or RT/PCR confirmation of collagen 2 and collagen 9 gene expression. Chondrogenesis can also be observed by growing the stem cells in a pellet, formed, e.g., by gently centrifuging stem cells in suspension (e.g., at about 800 g for about 5 minutes). After about 1-28 days, the pellet of stem cells begins to form a tough matrix and demonstrates a structural integrity not found in non-induced, or non-chondrogenic, cell lines, pellets of which tend to fall apart when challenged. Chondrogenesis can also be demonstrated, e.g., in such cell pellets, by staining with a stain that stains collage, e.g., Sirius Red, and/or a stain that stains glycosaminoglycans (GAGs), such as, e.g., Alcian Blue.

5.6.4 Induction of Differentiation into Osteogenic Cells

Osteogenic differentiation of placental stem cells can be accomplished, for example, by placing placental stem cells in cell culture conditions that induce differentiation into osteogenic cells. A preferred osteocytic medium comprises MSCGM (Cambrex) or DMEM supplemented with 15% cord blood serum, followed by Osteogenic Induction Medium (Cambrex) containing 0.1 µM dexamethasone, 0.05 mM ascorbic acid-2-phosphate, 10 mM beta glycerophosphate. In another embodiment, placental stem cells are cultured in medium (e.g., DMEM-low glucose) containing about $10^{-7}$ to about $10^{-9}$ M dexamethasone, about 10-50 µM ascorbate phosphate salt (e.g., ascorbate-2-phosphate) and about 10 nM to about 10 mM β-glycerophosphate. Osteogenic medium can also include serum, one or more antibiotic/antimycotic agents, transforming growth factor-beta (e.g., TGF-β1) and/or bone morphogenic protein (e.g., BMP-2, BMP-4, or a combination thereof).

Differentiation can be assayed using a calcium-specific stain, e.g., von Kossa staining, and RT/PCR detection of, e.g., alkaline phosphatase, osteocalcin, bone sialoprotein and/or osteopontin gene expression.

5.6.5 Induction of Differentiation into Pancreatic Cells

Differentiation of placental stem cells into insulin-producing pancreatic cells can be accomplished, for example, by placing placental stem cells in cell culture conditions that induce differentiation into pancreatic cells.

An example pancreagenic medium comprises DMEM/20% CBS, supplemented with basic fibroblast growth factor, 10 ng/ml; and transforming growth factor beta-1, 2 ng/ml. This medium is combined with conditioned media from nestin-positive neuronal cell cultures at 50/50 v/v. KnockOut Serum Replacement can be used in lieu of CBS. Cells are cultured for 14-28 days, refeeding every 3-4 days.

Differentiation can be confirmed by assaying for, e.g., insulin protein production, or insulin gene expression by RT/PCR.

5.6.6 Induction of Differentiation into Cardiac Cells

Myogenic (cardiogenic) differentiation of placental stem cells can be accomplished, for example, by placing placental stem cells in cell culture conditions that induce differentiation into cardiomyocytes. A preferred cardiomyocytic medium comprises DMEM/20% CBS supplemented with retinoic acid, 1 µM; basic fibroblast growth factor, 10 ng/ml; and transforming growth factor beta-1, 2 ng/ml; and epidermal growth factor, 100 ng/ml. KnockOut Serum Replacement (Invitrogen, Carlsbad, Calif.) may be used in lieu of CBS. Alternatively, placental stem cells are cultured in DMEM/20% CBS supplemented with 50 ng/ml Cardiotropin-1 for 24 hours. In another embodiment, placental stem cells can be cultured 10-14 days in protein-free medium for 5-7 days, then stimulated with human myocardium extract, e.g., produced by homogenizing human myocardium in 1% HEPES buffer supplemented with 1% cord blood serum.

Differentiation can be confirmed by demonstration of cardiac actin gene expression, e.g., by RT/PCR.

5.7 Preservation of Placental Stem Cells

Placental stem cells can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Medium for Collecting Placental Stem Cells and Preserving Organs," filed on Dec. 25, 2005. In one embodiment, provided herein is a method of preserving a population of stem cells comprising contacting said population of stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said population of stem cells. In another more specific embodiment, said contacting is performed during freezing and thawing of said population of stem cells.

In another embodiment, provided herein is a method of preserving a population of placental stem cells comprising contacting said population of stem cells with an inhibitor of apoptosis and an organ-preserving compound, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stem et al., U.S. Pat. No. 5,552,267. In another embodiment, said organ-preserving compound is hydroxyethyl starch, lactobionic acid, raffinose, or a combination thereof. In another embodiment, the stem cell collection composition additionally comprises an oxygen-carrying perfluorocarbon, either in two phases or as an emulsion.

In another embodiment of the method, placental stem cells are contacted with a stem cell collection composition comprising an apoptosis inhibitor and oxygen-carrying perfluorocarbon, organ-preserving compound, or combination thereof, during perfusion. In another embodiment, said stem cells are contacted during a process of tissue disruption, e.g., enzymatic digestion. In another embodiment, placental stem cells are contacted with said stem cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of stem cells is exposed to said hypoxic condition for less than two hours during said preservation. In another more specific embodiment, said population of stem cells is exposed to said hypoxic condition for less than one hour, or less than thirty minutes, or is not exposed to a hypoxic condition, during collection, enrichment or isolation. In another specific embodiment, said population of stem cells is not exposed to shear stress during collection, enrichment or isolation.

The placental stem cells provided herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. Placental stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.8 Uses of Placental Stem Cells

5.8.1 Placental Perfusate, Stem Cells and Stem Cell Populations

Placental stem cell populations can be used to treat any disease, disorder or condition that is amenable to treatment by administration of a population of stem cells. As used herein, "treat" encompasses the cure of, remediation of, improvement of, lessening of the severity of, or reduction in the time course of, a disease, disorder or condition, or any parameter or symptom thereof.

Placental stem cells, and populations of placental stem cells, can be induced to differentiate into a particular cell type, either ex vivo or in vivo, in preparation for administration to an individual in need of stem cells, or cells differentiated from stem cells. For example, placental stem cells can be injected into a damaged organ, and for organ neogenesis and repair of injury in vivo. Such injury may be due to such conditions and disorders including, but not limited to, bone defects including lesions resulting from cancer, fractures, and spinal conditions treatable with, e.g., spinal fusion. The placental stem cells can be injected into the damaged bone alone or can be introduced with an implantable substrate as described herein. Isolated populations of placental stem cells can be used, in specific embodiments, to treat specific diseases or conditions, including, but not limited to multiple myeloma, cancers including bone cancer, neuroblastoma, osteosarcoma, Ewing's sarcoma, chondrosarcoma, chordoma, malignant fibrous histiocytoma of bone, fibrosarcoma of bone, metastatic cancer, multiple myeloma, and any form of metastatic cancer characterized by bone metastases. As one skilled in the art will recognize, treatment of bone defects caused by cancer will not necessarily abate the cancer itself. Treatment of bone defects as provided herein can occur before, after, or concurrently with additional cancer therapies. Accordingly, in one embodiment, bone defects are treated before the cancer is treated with an anti-cancer therapy. In another embodiment, bone defects are treated at or near the same time that the cancer is treated with an anti-cancer therapy. In another embodiment, bone defects are treated after the cancer is treated with an anti-cancer therapy.

Isolated placental perfusate, placental perfusate cells, and/or isolated populations of placental stem cells may also be used to treat bone fractures, e.g., non-union bone fractures. Isolated populations of placental stem cells may also be used to fuse vertebrae together in order to, e.g., complete a spinal fusion in a subject in need thereof. Isolated populations of placental stem cells, in combination with stem or progenitor cell populations, may also be used to treat the foregoing.

In certain embodiments of the above methods of treating bone defects, placental perfusate, placental perfusate cells and/or placental stem cells, e.g., adherent or nonadherent placental stem cells, can be administered to an individual having a bone defect. Such an individual can be administered with, e.g., placental perfusate as obtained from a placenta; placental perfusate that has been treated to remove one or more cell types, e.g., erythrocytes; placental perfusate cells isolated from placental perfusate, or combinations of any of the foregoing. Such combinations can also comprise isolated adherent placental stem cells and or isolated nonadherent placental stem cells, as described elsewhere herein. Combinations of placental perfusate, isolated placental perfusate cells and/or placental stem cells useful to treat a bone defect, or an individual having a bone defect, are described in Section 5.4, above.

In specific embodiments of the method of treatment, the placental cells are contained within whole (unprocessed) placental perfusate. In another specific embodiment, the placental cells are placental perfusate cells. In another specific embodiment, the placental cells are placental stem cells. In certain more specific embodiments, the stem cells are nonadherent. In certain embodiments, the stem cells are $CD34^+$. In certain embodiments, the stem cells are $CD44^-$. In certain embodiments, the said stem cells are $CD34^+$ and $CD44^-$. In certain embodiments, the said stem cells are $CD9^+$, $CD54^+$, $CD90^+$, or $CD166^+$. In certain embodiments, the said stem cells are $CD9^+$, $CD54^+$, $CD90^+$, and $CD166^+$. In certain embodiments, the said stem cells are $CD31^+$, $CD117^+$, $CD133^+$, or $CD200^+$. In certain embodiments, the said stem cells are $CD31^+$, $CD117^+$, $CD133^+$, and $CD200^+$. In certain embodiments, at least about 70% of said cells are $CD34^+$ and $CD44^-$ stem cells. In certain embodiments, the at least about 90% of said cells are $CD34^+$ and $CD44^-$ stem cells. In certain other embodiments of the method, the placental stem cells are adherent. In specific embodiments, the adherent placental stem cells are $CD200^+$ and $HLA-G^+$; $CD73^+$, $CD105^+$, and $CD200^+$; $CD200^+$ and $OCT-4^+$; $CD73^+$, $CD105^+$ and $HLA-G^+$; $CD73^+$ and $CD105^+$ and facilitates the formation of one or more embryoid-like bodies in a population of placental cells comprising said stem cell when said population is cultured under conditions that allow the formation of an embryoid-like body; or $OCT-4^+$ and facilitates the formation of one or more embryoid-like bodies in a population of placental cells comprising the stem cell when said population is cultured under conditions that allow formation of embryoid-like bodies; or any combination thereof. In more specific embodiments of the nonadherent placental stem cells, the isolated $CD200^+$, $HLA-G^+$ stem cell is $CD34^-$, $CD38^-$, $CD45^-$, CD73+ and CD105+; the isolated CD73+, CD105+, and CD200+ stem cell is CD34−, CD38−, CD45−, and HLA-G+; the isolated CD200+, OCT-4+ stem cell is CD34−, CD38−, CD45−, CD73+, CD105+ and HLA-G+; the isolated stem cell of claim 1, wherein said CD73+, CD105+ and HLA-G+ stem cell is CD34−, CD45−, OCT-4+ and CD200+; the isolated CD73+ and CD105+ stem cell that facilitates the formation of one or more embryoid-like bodies is OCT4+, CD34−, CD38− and CD45−; and/or the isolated OCT-4+ and which facilitates the formation of one or more embryoid-like bodies is CD73+, CD105+, CD200+, CD34−, CD38−, and CD45−. In certain embodiments, the population of placental stem cells has been expanded.

When placental perfusate, placental perfusate cells, or placental stem cells are administered as a suspension or liquid injectable, the cells can be administered intravenously, or, preferably, at the site of the bone defect, e.g., break.

Also provided herein is a method for treating bone defects in a subject, comprising administering to a subject in need thereof an implantable or injectable composition comprising a population of stem cells provided herein, thereby treating the bone defect in the subject. In certain embodiments, the bone defect is an osteolytic lesion associated with a cancer, a bone fracture, or a spine, e.g., in need of fusion. In certain embodiments, the osteolytic lesion is associated with multiple myeloma, bone cancer, or metastatic cancer. In certain embodiments, the bone fracture is a non-union fracture. In certain embodiments, an implantable composition comprising a population of nonadherent stem cells is administered to the subject. In certain embodiments, an implantable composition is surgically implanted, e.g., at the site of the bone defect. In certain embodiments, an injectable composition comprising a population of nonadherent stem cells is administered to the subject. In certain embodiments, an injectable composition is surgically administered to the region of the bone defect. In certain embodiments, the injectable composition is systemically administered.

In another aspect, provided herein is a method for formulating an injectable composition, comprising combining a population of placental cells with injectable hyaluronic acid or collagen. In a specific embodiment, the placental cells are contained within whole (unprocessed) placental perfusate. In another specific embodiment, the placental cells are placental perfusate cells. In another specific embodiment, the placental cells are placental stem cells. In certain more specific embodiments, the stem cells are nonadherent. In certain embodiments, the stem cells are CD34+. In certain embodiments, the stem cells are CD44−. In certain embodiments, the said stem cells are CD34+ and CD44−. In certain embodiments, the said stem cells are CD9+, CD54+, CD90+, or CD166+. In certain embodiments, the said stem cells are CD9+, CD54+, CD90+, and CD166+. In certain embodiments, the said stem cells are CD31+, CD117+, CD133+, or CD200+. In certain embodiments, the said stem cells are CD31+, CD117+, CD133+, and CD200+. In certain embodiments, at least about 70% of said cells are CD34+ and CD44− stem cells. In certain embodiments, the at least about 90% of said cells are CD34+ and CD44− stem cells. In certain other embodiments of the method, the placental stem cells are adherent. In specific embodiments, the adherent placental stem cells are CD200+ and HLA-G+; CD73+, CD105+, and CD200+; CD200+ and OCT-4+; CD73+, CD105+ and HLA-G+; CD73+ and CD105+ and facilitates the formation of one or more embryoid-like bodies in a population of placental cells comprising said stem cell when said population is cultured under conditions that allow the formation of an embryoid-like body; or OCT-4+ and facilitates the formation of one or more embryoid-like bodies in a population of placental cells comprising the stem cell when said population is cultured under conditions that allow formation of embryoid-like bodies; or any combination thereof. In more specific embodiments of the nonadherent placental stem cells, the isolated CD200+, HLA-G+ stem cell is CD34−, CD38−, CD45−, CD73+ and CD105+; the isolated CD73+, CD105+, and CD200+ stem cell is CD34−, CD38−, CD45−, and HLA-G+; the isolated CD200+, OCT-4+ stem cell is CD34−, CD38−, CD45−, CD73+, CD105+ and HLA-G+; the isolated stem cell of claim 1, wherein said CD73+, CD105+ and HLA-G+ stem cell is CD34−, CD45−, OCT-4+ and CD200+; the isolated CD73+ and CD105+ stem cell that facilitates the formation of one or more embryoid-like bodies is OCT4+, CD34−, CD38− and CD45−; and/or the isolated OCT-4+ and which facilitates the formation of one or more embryoid-like bodies is CD73+, CD105+, CD200+, CD34−, CD38−, and CD45−. In certain embodiments, the population of placental stem cells has been expanded. In certain embodiments, the said composition comprises injectable hyaluronic acid. In certain embodiments, the composition comprises injectable collagen. Provided herein are also compositions comprising a population of nonadherent stem cells and injectable hyaluronic acid or collagen.

Placental stem cells can be administered without being cultured under conditions that cause the stem cells to differentiate. Alternately, the stem cells can be cultured in, e.g., osteogenic medium for, e.g., about 1-20 days, prior to administration. Alternately, placental stem cells can be isolated and seeded on a matrix, then cultured in osteogenic medium for, e.g., about 1-20 days. In another embodiment, placental stem cells can be cultured in, e.g., osteogenic medium for, e.g., about 1-20 days, then seeded onto a matrix, then cultured in osteogenic medium as described herein for, e.g., about 1-20 days.

In other embodiments, isolated populations of placental stem cells may be used in autologous or heterologous tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

In certain embodiments, an isolated population of placental stem cells is used in hematopoietic reconstitution in an individual that has suffered a partial or total loss of hematopoietic stem cells, e.g., individuals exposed to lethal or sublethal doses of radiation (whether industrial, medical or military); individuals that have undergone myeloablation as part of, e.g., cancer therapy, and the like. Isolated populations of placental-derived stem cells can be used in place of, or to supplement, bone marrow or populations of stem cells derived from bone marrow. Typically, approximately $1\times10^8$ to $2\times10^8$ bone marrow mononuclear cells per kilogram of patient weight are infused for engraftment in a bone marrow transplantation (i.e., about 70 ml of marrow for a 70 kg donor). To obtain 70 ml requires an intensive donation and significant loss of donor blood in the donation process. An isolated population of placental stem cells for hematopoietic reconstitution can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

The placental stem cells provided herein, alone or in combination with other stem cell or progenitor cell populations, can be used in the manufacture of a tissue or organ in vivo.

The methods provided herein encompass using cells obtained from the placenta, e.g., stem cells or progenitor cells, to seed a matrix and to be cultured under the appropriate conditions to allow the cells to differentiate and populate the matrix. The tissues and organs obtained by the methods provided herein can be used for a variety of purposes, including research and therapeutic purposes.

In a preferred embodiment, adherent placental stem cells as provided herein, and populations of such stem cells, may be used for autologous and allogenic transplants, including matched and mismatched HLA type hematopoietic transplants. In one embodiment of the use of placental stem cells as allogenic hematopoietic transplants, the host is treated to reduce immunological rejection of the donor cells, or to create immunotolerance (see, e.g., U.S. Pat. Nos. 5,800,539 and 5,806,529). In another embodiment, the host is not treated to reduce immunological rejection or to create immunotolerance.

Placental stem cells, either alone or in combination with one or more other stem cell populations, can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair. Additionally, placental stem cells may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

Placental stem cells as provided herein, and populations of the same, can be used for augmentation, repair or replacement of cartilage, tendon, or ligaments. For example, in certain embodiments, prostheses (e.g., hip prostheses) can be coated with replacement cartilage tissue constructs grown from placental stem cells provided herein. In other embodiments, joints (e.g., knee) can be reconstructed with cartilage tissue constructs grown from placental stem cells. Cartilage tissue constructs can also be employed in major reconstructive surgery for different types of joints (see, e.g., Resnick & Niwayama, eds., 1988, Diagnosis of Bone and Joint Disorders, 2d ed., W. B. Saunders Co.).

The adherent placental stem cells provided herein can be used to repair damage to tissues and organs resulting from, e.g., trauma, metabolic disorders, or disease. In such an embodiment, a patient can be administered placental stem cells, alone or combined with other stem or progenitor cell populations, to regenerate or restore tissues or organs which have been damaged as a consequence of disease.

5.8.2 Compositions Comprising Placental Stem Cells

Provided herein are compositions comprising placental stem cells, or biomolecules therefrom. The adherent placental stem cells provided herein can be combined with any physiologically-acceptable or medically-acceptable compound, composition or device for use in, e.g., research or therapeutics.

5.8.2.1 Cryopreserved Placental Stem Cells

The placental stem cell populations provided herein can be preserved, for example, cryopreserved for later use. Methods for cryopreservation of cells, such as stem cells, are well known in the art. Placental stem cell populations can be prepared in a form that is easily administrable to an individual. For example, provided herein is a placental stem cell population that is contained within a container that is suitable for medical use. Such a container can be, for example, a sterile plastic bag, flask, jar, or other container from which the placental stem cell population can be easily dispensed. For example, the container can be a blood bag or other plastic, medically-acceptable bag suitable for the intravenous administration of a liquid to a recipient. The container is preferably one that allows for cryopreservation of the combined stem cell population.

The cryopreserved placental stem cell population can comprise placental stem cells derived from a single donor, or from multiple donors. The placental stem cell population can be completely HLA-matched to an intended recipient, or partially or completely HLA-mismatched.

Thus, in one embodiment, provided herein is a composition comprising a placental stem cell population in a container. In a specific embodiment, the stem cell population is cryopreserved. In another specific embodiment, the container is a bag, flask, or jar. In more specific embodiment, said bag is a sterile plastic bag. In a more specific embodiment, said bag is suitable for, allows or facilitates intravenous administration of said placental stem cell population. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cell population is contained within a physiologically-acceptable aqueous solution. In a more specific embodiment, said physiologically-acceptable aqueous solution is a 0.9% NaCl solution. In another specific embodiment, said placental stem cell population comprises placental cells that are HLA-matched to a recipient of said stem cell population. In another specific embodiment, said combined stem cell population comprises placental cells that are at least partially HLA-mismatched to a recipient of said stem cell population. In another specific embodiment, said placental stem cells are derived from a plurality of donors.

5.8.2.2 Pharmaceutical Compositions

Populations of placental stem cells, or populations of cells comprising placental stem cells, can be formulated into pharmaceutical compositions for use in vivo. Such pharmaceutical compositions comprise a population of placental stem cells, or a population of cells comprising placental stem cells, in a pharmaceutically-acceptable carrier, e.g., a saline solution or other accepted physiologically-acceptable solution for in vivo administration. Pharmaceutical compositions provided herein can comprise any of the placental stem cell populations, or placental stem cell types, described elsewhere herein. The pharmaceutical compositions can comprise fetal, maternal, or both fetal and maternal placental stem cells. The pharmaceutical compositions provided herein can further comprise placental stem cells obtained from a single individual or placenta, or from a plurality of individuals or placentae.

The pharmaceutical compositions provided herein can comprise any number of placental stem cells. For example, a single unit dose of placental stem cells can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more placental stem cells.

The pharmaceutical compositions provided herein can comprise populations of cells that comprise 50% viable cells or more (that is, at least about 50% of the cells in the population are functional or living). Preferably, at least about 60% of the cells in the population are viable. More preferably, at least about 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

5.8.2.3 Placental Stem Cell Conditioned Media

The placental stem cells provided herein can be used to produce conditioned medium, that is, medium comprising one or more biomolecules secreted or excreted by the stem cells. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least about 30%, 40%, 50%, 60%, 70%, 80%, 90% confluence, or up to 100% confluence. Such conditioned medium can be used to support the culture of a separate population of placental stem cells, or stem cells of another kind. In another embodiment, the conditioned medium comprises medium in which placental stem cells have been differentiated into an adult cell type. In another embodiment, the conditioned medium provided herein comprises medium in which placental stem cells and non-placental stem cells have been cultured.

5.8.2.4 Matrices Comprising Placental Stem Cells

Further provided herein are matrices, hydrogels, scaffolds, and the like that comprise a placental stem cell, or a population of placental stem cells. In certain embodiments, the matrix can be any substrate known to one skilled in the art to be useful for treating bone defects. For example, the matrix can be a β-tricalcium phosphate substrate, a β-tricalcium phosphate-collagen substrate, a collagen substrate, a calcium phosphate substrate, a mineralized collagen substrate, and a hyaluronic acid substrate. In some embodiments, the collagen in the matrix can be placental collagen. Methods and compositions for isolating and preparing placental collagen are extensively described, for example, in U.S. patent application Ser. No. 11/450,934, filed Jun. 9, 2006.

Placental stem cells can be seeded onto the matrix for treating bone prior to or after a differentiation step. For example, placental stem cells can be cultured in, e.g., osteogenic medium for, e.g., about 1-20 days, then seeded onto the matrix. Alternately, placental stem cells can be isolated and seeded onto the matrix, then cultured in osteogenic medium as described herein for, e.g., about 1-20 days. In another embodiment, placental stem cells are cultured in, e.g., osteogenic medium for, e.g., about 1-20 days, then seeded onto the matrix, then cultured in osteogenic medium as described herein for, e.g., about 1-20 days.

Placental stem cells can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796.

Placental stem cells as provided herein can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Placental stem cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix biodegradable.

In some embodiments, the formulation comprises an in situ polymerizable gel (see, e.g., U.S. Patent Application Publication 2002/0022676; Anseth et al., *J. Control Release*, 78(1-3):199-209 (2002); Wang et al., *Biomaterials*, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve repair of tissue.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

Placental stem cells provided herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells provided herein can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1 M acetic acid followed by incubation in polylysine, PBS, and/or collagen, prior to inoculation of the placental stem cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells. The scaffold can further comprise agents that stimulate bone growth and/or inhibit bone resorption. For example, the scaffold can comprise bone morphogenic proteins, e.g., BMP-2 and/or BMP-7, WNT inhibitors, and the like.

5.8.3 Immortalized Placental Stem Cell Lines

Mammalian placental cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{cMV*-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed as described herein. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least about 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental stem cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental stem cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental stem cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.8.4 Assays

The placental stem cells provided herein can be used in assays to determine the influence of culture conditions, environmental factors, molecules (e.g., biomolecules, small inorganic molecules. etc.) and the like on stem cell proliferation, expansion, and/or differentiation, compared to placental stem cells not exposed to such conditions.

In a preferred embodiment, the placental stem cells provided herein are assayed for changes in proliferation, expansion or differentiation upon contact with a molecule. For example, osteogenic differentiation can be assayed by monitoring alkaline phosphatase activity and/or calcium mineralization.

In one embodiment, for example, provided herein is a method of identifying a compound that modulates the proliferation of a plurality of placental stem cells, comprising contacting said plurality of stem cells with said compound under conditions that allow proliferation, wherein if said compound causes a detectable change in proliferation of said plurality of stem cells compared to a plurality of stem cells not contacted with said compound, said compound is identified as a compound that modulates proliferation of placental stem cells. In a specific embodiment, said compound is identified as an inhibitor of proliferation. In another specific embodiment, said compound is identified as an enhancer of proliferation.

In another embodiment, provided herein is a method of identifying a compound that modulates the expansion of a plurality of placental stem cells, comprising contacting said plurality of stem cells with said compound under conditions that allow expansion, wherein if said compound causes a detectable change in expansion of said plurality of stem cells compared to a plurality of stem cells not contacted with said compound, said compound is identified as a compound that modulates expansion of placental stem cells. In a specific embodiment, said compound is identified as an inhibitor of expansion. In another specific embodiment, said compound is identified as an enhancer of expansion.

In another embodiment, provided herein is a method of identifying a compound that modulates the differentiation of a placental stem cell, comprising contacting said stem cells with said compound under conditions that allow differentiation, wherein if said compound causes a detectable change in differentiation of said stem cells compared to a stem cell not contacted with said compound, said compound is identified as a compound that modulates proliferation of placental stem cells. In a specific embodiment, said compound is identified as an inhibitor of differentiation. In another specific embodiment, said compound is identified as an enhancer of differentiation.

6. EXAMPLES

The following examples are intended to illustrate the present embodiments and are not to be construed to be limiting in any way. All references, whether patent references, literature references, or otherwise, cited herein are hereby incorporated by reference for all purposes.

6.1 Example 1

Culture of Placental Stem Cells

Placental stem cells are obtained from a post-partum mammalian placenta either by perfusion or by physical disruption, e.g., enzymatic digestion. The cells are cultured in a culture medium comprising 60% DMEM-LG (Gibco), 40% MCDB-201 (Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^{-4}$ M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/100 U streptomycin.

The culture flask in which the cells are cultured is prepared as follows. T75 flasks are coated with fibronectin (FN), by adding 5 ml PBS containing 5 ng/ml human FN (Sigma F0895) to the flask. The flasks with FN solution are left at 37° C. for 30 min. The FN solution is then removed prior to cell culture. There is no need to dry the flasks following treatment. Alternatively, the flasks are left in contact with the FN solution at 4° C. overnight or longer; prior to culture, the flasks are warmed and the FN solution is removed.

Placental Stem Cells Isolated by Perfusion

Cultures of placental stem cells from placental perfusate are established as follows. Cells from a Ficoll gradient are seeded in FN-coated T75 flasks, prepared as above, at $50\text{-}100 \times 10^6$ cells/flask in 15 ml culture medium. Typically, 5 to 10 flasks are seeded. The flasks are incubated at 37° C. for 12-18 hrs to allow the attachment of adherent cells. 10 ml of warm PBS is added to each flask to remove cells in suspension, and mixed gently. 15 mL of the medium is then removed and replaced with 15 ml fresh culture medium. All medium is changed 3-4 days after the start of culture. Subsequent culture medium changes are performed, during which 50% or 7.5 ml of the medium is removed.

Starting at about day 12, the culture is checked under a microscope to examine the growth of the adherent cell colonies. When cell cultures become approximately 80% confluent, typically between day 13 to day 18 after the start of culture, adherent cells are harvested by trypsin digestion. Cells harvested from these primary cultures are designated passage 0 (zero).

Placental Stem Cells Isolated by Physical Disruption and Enzymatic Digestion

Placental stem cell cultures are established from digested placental tissue as follows. The perfused placenta is placed on a sterile paper sheet with the maternal side up. Approximately 0.5 cm of the surface layer on maternal side of placenta is scraped off with a blade, and the blade is used to remove a placental tissue block measuring approximately 1×2×1 cm. This placenta tissue is then minced into approximately 1 mm³ pieces. These pieces are collected into a 50 ml Falcon tube and digested with collagenase IA (2 mg/ml, Sigma) for 30 minutes, followed by trypsin-EDTA (0.25%, GIBCO BRL) for 10 minutes, at 37° C. in water bath. The resulting solution is centrifuged at 400 g for 10 minutes at room temperature, and the digestion solution is removed. The pellet is resuspended to approximately 10 volumes with PBS (for example, a 5 ml pellet is resuspended with 45 ml PBS), and the tubes are centrifuged at 400 g for 10 minutes at room temperature. The tissue/cell pellet is resuspended in 130 mL culture medium, and the cells are seeded at 13 ml per fibronectin-coated T-75 flask. Cells are incubated at 37° C. with a humidified atmosphere with 5% $CO_2$. Placental Stem Cells are optionally cryopreserved at this stage.

Subculturing and Expansion of Placental Stem Cells

Cryopreserved cells are quickly thawed in a 37° C. water bath. Placental stem cells are immediately removed from the cryovial with 10 ml warm medium and transferred to a 15 ml sterile tube. The cells are centrifuged at 400 g for 10 minutes at room temperature. The cells are gently resuspended in 10 ml of warm culture medium by pipetting, and viable cell counts are determined by Trypan blue exclusion. Cells are then seeded at about 6000-7000 cells per cm² onto FN-coated flasks, prepared as above (approximately $5 \times 10^5$ cells per T-75 flask). The cells are incubated at 37° C., 5% $CO_2$ and 90% humidity. When the cells reached 75-85% confluency, all of the spent media is aseptically removed from the flasks and discarded. 3 ml of 0.25% trypsin/EDTA (w/v) solution is added to cover the cell layer, and the cells are incubated at 37° C., 5% $CO_2$ and 90% humidity for 5 minutes. The flask is tapped once or twice to expedite cell detachment. Once >95% of the cells are rounded and detached, 7 ml of warm culture medium is added to each T-75 flask, and the solution is dispersed by pipetting over the cell layer surface several times.

After counting the cells and determining viability as above, the cells are centrifuged at 1000 RPM for 5 minutes at room temperature. Cells are passaged by gently resuspending the cell pellet from one T-75 flask with culture medium, and evenly plating the cells onto two FN-coated T-75 flasks.

Using the above methods, populations of adherent placental stem cells are identified that express markers CD105, CD117, CD33, CD73, CD29, CD44, CD10, CD90 and CD133. This population of cells did not express CD34 or CD45. Some, but not all cultures of these placental stem cells expressed HLA-ABC and/or HLA-DR.

6.2 Example 2

Isolation of Placental Stem Cells from Placental Structures

6.2.1 Materials & Methods

6.2.1.1 Isolation of the Phenotype of Interest

Five distinct populations of placental cells were obtained from the placentas of normal, full-term pregnancies. All donors provided full written consent for the use of their placentas for research purposes. Five populations of placental cells were examined: (1) placental perfusate (from perfusion of the placental vasculature); and enzymatic digestions of (2) amnion, (3) chorion, (4) amnion-chorion plate, and (5) umbilical cord. The various placental tissues were cleaned in sterile PBS (Gibco-Invitrogen Corporation, Carlsbad, Calif.) and placed on separate sterile Petri dishes. The various tissues were minced using a sterile surgical scalpel and placed into 50 mL Falcon Conical tubes. The minced tissues were digested with IX Collagenase (Sigma-Aldrich, St. Louis, Mo.) for 20 minutes in a 37° C. water bath, centrifuged, and then digested with 0.25% Trypsin-EDTA (Gibco-Invitrogen Corp) for 10 minutes in a 37° C. water bath. The various tissues were centrifuged after digestion and rinsed once with sterile PBS (Gibco-Invitrogen Corp). The reconstituted cells were then filtered twice, once with 100 μm cell strainers and once with 30 μm separation filters, to remove any residual extracellular matrix or cellular debris.

6.2.1.2 Cellular Viability Assessment and Cell Counts

The manual trypan blue exclusion method was employed post digestion to calculate cell counts and assess cellular viability. Cells were mixed with Trypan Blue Dye (Sigma-Aldrich) at a ratio of 1:1, and the cells were read on hemacytometer.

6.2.1.3 Cell Surface Marker Characterization

Cells that were HLA ABC$^-$/CD45$^-$/CD34$^-$/CD133$^+$ were selected for characterization. Cells having this phenotype were identified, quantified, and characterized by two of Becton-Dickinson flow cytometers, the FACSCalibur and the FACS Aria (Becton-Dickinson, San Jose, Calif., USA). The various placental cells were stained, at a ratio of about 10 μL of antibody per 1 million cells, for 30 minutes at room temperature on a shaker. The following anti-human antibodies were used: Fluorescein Isothiocyanate (FITC) conjugated monoclonal antibodies against HLA-G (Serotec, Raleigh, N.C.), CD10 (BD Immunocytometry Systems, San Jose, Calif.), CD44 (BD Biosciences Pharmingen, San Jose, Calif.), and CD105 (R&D Systems Inc., Minneapolis, Minn.); Phycoerythrin (PE) conjugated monoclonal antibodies against CD44, CD200, CD117, and CD13 (BD Biosciences Pharmingen); Phycoerythrin-Cy5 (PE Cy5) conjugated Streptavidin and monoclonal antibodies against CD117 (BD Biosciences Pharmingen); Phycoerythrin-Cy7 (PE Cy7) conjugated monoclonal antibodies against CD33 and CD10 (BD Biosciences); Allophycocyanin (APC) conjugated streptavidin and monoclonal antibodies against CD38 (BD Biosciences Pharmingen); and Biotinylated CD90 (BD Biosciences Pharmingen). After incubation, the cells were rinsed once to remove unbound antibodies and were fixed overnight with 4% paraformaldehyde (USB, Cleveland, Ohio) at 4° C. The following day, the cells were rinsed twice, filtered through a 30 μm separation filter, and were run on the flow cytometer(s).

Samples that were stained with anti-mouse IgG antibodies (BD Biosciences Pharmingen) were used as negative controls and were used to adjust the Photo Multiplier Tubes (PMTs). Samples that were single stained with anti-human antibodies were used as positive controls and were used to adjust spectral overlaps/compensations.

6.2.1.4 Cell Sorting and Culture

One set of placental cells (from perfusate, amnion, or chorion) was stained with 7-Amino-Actinomycin D (7AAD; BD Biosciences Pharmingen) and monoclonal antibodies specific for the phenotype of interest. The cells were stained at a ratio of 10 μL of antibody per 1 million cells, and were incubated for 30 minutes at room temperature on a shaker. These cells were then positively sorted for live cells expressing the phenotype of interest on the BD FACS Aria and plated into culture. Sorted (population of interest) and "All" (non-sorted) placental cell populations were plated for comparisons. The cells were plated onto a fibronectin (Sigma-Aldrich) coated 96 well plate at the cell densities listed in Table 1 (cells/cm$^2$). The cell density, and whether the cell type was plated in duplicate or triplicate, was determined and governed by the number of cells expressing the phenotype of interest.

TABLE 1

Cell plating densities
96 Well Plate Culture
Density of Plated Cells

| Conditions | Sorted | All | All Max. Density |
|---|---|---|---|
| Cell Source | | A | |
| Set #1: | 40.6 K/cm$^2$ | 40.6 K/cm$^2$ | 93.8 K/cm$^2$ |
| Set #2 | 40.6 K/cm$^2$ | 40.6 K/cm$^2$ | 93.8 K/cm$^2$ |
| Set #3: | 40.6 K/cm$^2$ | 40.6 K/cm$^2$ | 93.8 K/cm$^2$ |
| Cell Source | | B | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |

TABLE 1-continued

| | Cell plating densities 96 Well Plate Culture Density of Plated Cells | | |
|---|---|---|---|
| Conditions | Sorted | All | All Max. Density |
| Cell Source | | C | |
| Set #1: | 6.3 K/cm² | 6.3 K/cm² | 62.5 K/cm² |
| Set #2 | 6.3 K/cm² | 6.3 K/cm² | 62.5 K/cm² |

Complete medium (60% DMEM-LG (Gibco) and 40% MCDB-201 (Sigma); 2% fetal calf serum (Hyclone Labs.); 1× insulin-transferrin-selenium (ITS); 1× linoleic acid-bovine serum albumin (LA-BSA); $10^{-9}$ M dexamethasone (Sigma); $10^{-4}$ M ascorbic acid 2-phosphate (Sigma); epidermal growth factor 10 ng/mL (R&D Systems); and platelet-derived growth factor (PDGF-BB) 10 ng/mL (R&D Systems)) was added to each well of the 96 well plate and the plate was placed in a 5% $CO_2$/37° C. incubator. On day 7, 100 µL of complete medium was added to each of the wells. The 96 well plate was monitored for about two weeks and a final assessment of the culture was completed on day 12.

6.2.1.5 Data Analysis

FACSCalibur data was analyzed in FlowJo (Tree star, Inc) using standard gating techniques. The BD FACS Aria data was analyzed using the FACSDiva software (Becton-Dickinson). The FACS Aria data was analyzed using doublet discrimination gating to minimize doublets, as well as, standard gating techniques. All results were compiled in Microsoft Excel and all values, herein, are represented as average ±standard deviation (number, standard error of mean).

6.2.2 Results 6.2.2.1 Cellular Viability

Post-digestion viability was assessed using the manual trypan blue exclusion method (FIG. 1). The average viability of cells obtained from the majority of the digested tissue (from amnion, chorion or amnion-chorion plate) was around 70%. Amnion had an average viability of 74.35%±10.31% (n=6, SEM=4.21), chorion had an average viability of 78.18%±12.65% (n=4, SEM=6.32), amnion-chorion plate had an average viability of 69.05%±10.80% (n=4, SEM=5.40), and umbilical cord had an average viability of 63.30%±20.13% (n=4, SEM=10.06). Cells from perfusion, which did not undergo digestion, retained the highest average viability, 89.98±6.39% (n=5, SEM=2.86).

6.2.2.2 Cell Quantification

The five distinct populations of placenta derived cells were analyzed to determine the numbers of HLA ABC⁻/CD45⁻/CD34⁻/CD133⁺ cells. From the analysis of the BD FACS-Calibur data, it was observed that the amnion, perfusate, and chorion contained the greatest total number of these cells, 30.72±21.80 cells (n=4, SEM=10.90), 26.92±22.56 cells (n=3, SEM=13.02), and 18.39±6.44 cells (n=2, SEM=4.55) respectively (data not shown). The amnion-chorion plate and umbilical cord contained the least total number of cells expressing the phenotype of interest, 4.72±4.16 cells (n=3, SEM=2.40) and 3.94±2.58 cells (n=3, SEM=1.49) respectively (data not shown).

Similarly, when the percent of total cells expressing the phenotype of interest was analyzed, it was observed that amnion and placental perfusate contained the highest percentages of cells expressing this phenotype (0.0319%±0.0202% (n=4, SEM=0.0101) and 0.0269%±0.0226% (n=3, SEM=0.0130) respectively (FIG. 2). Although umbilical cord contained a small number of cells expressing the phenotype of interest (FIG. 2), it contained the third highest percentage of cells expressing the phenotype of interest, 0.020±0.0226% (n=3, SEM=0.0131) (FIG. 2). The chorion and amnion-chorion plate contained the lowest percentages of cells expressing the phenotype of interest, 0.0184±0.0064% (n=2, SEM=0.0046) and 0.0177±0.0173% (n=3, SEM=0.010) respectively (FIG. 2).

Consistent with the results of the BD FACSCalibur analysis, the BD FACS Aria data also identified amnion, perfusate, and chorion as providing higher numbers of HLA ABC⁻/CD45⁻/CD34⁻/CD133⁺ cells than the remaining sources. The average total number of cells expressing the phenotype of interest among amnion, perfusate, and chorion was 126.47±55.61 cells (n=15, SEM=14.36), 81.65±34.64 cells (n=20, SEM=7.75), and 51.47±32.41 cells (n=15, SEM=8.37), respectively (data not shown). The amnion-chorion plate and umbilical cord contained the least total number of cells expressing the phenotype of interest, 44.89±37.43 cells (n=9, SEM=12.48) and 11.00±4.03 cells (n=9, SEM=1.34) respectively (data not shown).

BD FACS Aria data revealed that the B and A cell sources contained the highest percentages of HLA ABC⁻/CD45⁻/CD34⁻/CD133⁺ cells, 0.1523±0.0227% (n=15, SEM=0.0059) and 0.0929±0.0419% (n=20, SEM=0.0094) respectively (FIG. 3). The D cell source contained the third highest percentage of cells expressing the phenotype of interest, 0.0632±0.0333% (n=9, SEM=0.0111) (FIG. 3). The C and E cell sources contained the lowest percentages of cells expressing the phenotype of interest, 0.0623±0.0249% (n=15, SEM=0.0064) and 0.0457±10.0055% (n=9, SEM=0.0018) respectively (FIG. 3).

After HLA ABC⁻/CD45⁻/CD34⁻/CD133⁺ cells were identified and quantified from each cell source, its cells were further analyzed and characterized for their expression of cell surface markers HLA-G, CD10, CD13, CD33, CD38, CD44, CD90, CD105, CD117, CD200, and CD105.

6.2.2.3 Placental Perfusate-Derived Cells

Perfusate-derived cells were consistently positive for HLA-G, CD33, CD117, CD10, CD44, CD200, CD90, CD38, CD105, and CD13 (FIG. 4). The average expression of each marker for perfusate-derived cells was the following: 37.15%±38.55% (n=4, SEM=19.28) of the cells expressed HLA-G; 36.37%±21.98% (n=7, SEM=8.31) of the cells expressed CD33; 39.39%±39.91% (n=4, SEM=19.96) of the cells expressed CD117; 54.97%±33.08% (n=4, SEM=16.54) of the cells expressed CD10; 36.79%±11.42% (n=4, SEM=5.71) of the cells expressed CD44; 41.83%±19.42% (n=3, SEM=11.21) of the cells expressed CD200; 74.25%±26.74% (n=3, SEM=15.44) of the cells expressed CD90; 35.10%±23.10% (n=3, SEM=13.34) of the cells expressed CD38; 22.87%±6.87% (n=3, SEM=3.97) of the cells expressed CD105; and 25.49%±9.84% (n=3, SEM=5.68) of the cells expressed CD13.

6.2.2.4 Amnion-Derived Cells

Amnion-derived cells were consistently positive for HLA-G, CD33, CD117, CD10, CD44, CD200, CD90, CD38, CD105, and CD13 (FIG. 5). The average expression of each marker for amnion-derived was the following: 57.27%±41.11% (n=3, SEM=23.73) of the cells expressed HLA-G; 16.23%±15.81% (n=6, SEM=6.46) of the cells expressed CD33; 62.32%±37.89% (n=3, SEM=21.87) of the cells expressed CD117; 9.71%±13.73% (n=3, SEM=7.92) of the cells expressed CD10; 27.03%±22.65% (n=3, SEM=13.08) of the cells expressed CD44; 6.42%±0.88% (n=2, SEM=0.62) of the cells expressed CD200; 57.61%±22.10% (n=2, SEM=15.63) of the cells expressed CD90; 63.76%±4.40% (n=2, SEM=3.11) of the cells expressed CD38; 20.27%±5.88% (n=2, SEM=4.16) of the cells expressed CD105; and 54.37%±13.29% (n=2, SEM=9.40) of the cells expressed CD13.

6.2.2.5 Chorion-Derived Cells

Chorion-derived cells were consistently positive for HLA-G, CD117, CD10, CD44, CD200, CD90, CD38, and CD13, while the expression of CD33, and CD105 varied (FIG. 6). The average expression of each marker for chorion cells was the following: 53.25%±32.87% (n=3, SEM=18.98) of the cells expressed HLA-G; 15.44%±11.17% (n=6, SEM=4.56) of the cells expressed CD33; 70.76%±11.87% (n=3, SEM=6.86) of the cells expressed CD117; 35.84%±25.96% (n=3, SEM=14.99) of the cells expressed CD10; 28.76%±6.09% (n=3, SEM=3.52) of the cells expressed CD44; 29.20%±9.47% (n=2, SEM=6.70) of the cells expressed CD200; 54.88%±0.17% (n=2, SEM=0.12) of the cells expressed CD90; 68.63%±44.37% (n=2, SEM=31.37) of the cells expressed CD38; 23.81%±33.67% (n=2, SEM=23.81) of the cells expressed CD105; and 53.16%±62.70% (n=2, SEM=44.34) of the cells expressed CD13.

6.2.2.6 Source D Placental Cells

Cells from amnion-chorion plate were consistently positive for HLA-G, CD33, CD117, CD10, CD44, CD200, CD90, CD38, CD105, and CD13 (FIG. 7). The average expression of each marker for amnion-chorion plate-derived cells was the following: 78.52%±13.13% (n=2, SEM=9.29) of the cells expressed HLA-G; 38.33%±15.74% (n=5, SEM=7.04) of the cells expressed CD33; 69.56%±26.41% (n=2, SEM=18.67) of the cells expressed CD117; 42.44%±53.12% (n=2, SEM=37.56) of the cells expressed CD10; 32.47%±31.78% (n=2, SEM=22.47) of the cells expressed CD44; 5.56% (n=1) of the cells expressed CD200; 83.33% (n=1) of the cells expressed CD90; 83.52% (n=1) of the cells expressed CD38; 7.25% (n=1) of the cells expressed CD105; and 81.16% (n=1) of the cells expressed CD13.

6.2.2.7 Umbilical Cord-Derived Cells

Umbilical cord-derived cells were consistently positive for HLA-G, CD33, CD90, CD38, CD105, and CD13, while the expression of CD117, CD10, CD44, and CD200 varied (FIG. 8). The average expression of each marker for umbilical cord-derived cells was the following: 62.50%±53.03% (n=2, SEM=37.50) of the cells expressed HLA-G; 25.67%±11.28% (n=5, SEM=5.04) of the cells expressed CD33; 44.45%±62.85% (n=2, SEM=44.45) of the cells expressed CD117; 8.33%±11.79% (n=2, SEM=8.33) of the cells expressed CD10; 21.43%±30.30% (n=2, SEM=21.43) of the cells expressed CD44; 0.0% (n=1) of the cells expressed CD200; 81.25% (n=1) of the cells expressed CD90; 64.29% (n=1) of the cells expressed CD38; 6.25% (n=1) of the cells expressed CD105; and 50.0% (n=1) of the cells expressed CD13.

A summary of all marker expression averages is shown in FIG. 9.

6.2.2.8 BD FACS Aria Sort Report

The three distinct populations of placental cells that expressed the greatest percentages of HLA ABC, CD45, CD34, and CD133 (cells derived from perfusate, amnion and chorion) were stained with 7AAD and the antibodies for these markers. The three populations were positively sorted for live cells expressing the phenotype of interest. The results of the BD FACS Aria sort are listed in table 2.

TABLE 2

BD FACS Aria Sort Report

| Cell Source | Events Processed | Events Sorted (Phenotype of Interest) | % Of Total |
| --- | --- | --- | --- |
| Perfusate | 135540110 | 51215 | 0.037786 |
| Amnion | 7385933 | 4019 | 0.054414 |
| Chorion | 108498122 | 4016 | 0.003701 |

The three distinct populations of positively sorted cells ("sorted") and their corresponding non-sorted cells were plated and the results of the culture were assessed on day 12 (Table 3). Sorted perfusate-derived cells, plated at a cell density of 40,600/cm$^2$, resulted in small, round, non-adherent cells. Two out of the three sets of non-sorted perfusate-derived cells, each plated at a cell density of 40,600/cm$^2$, resulted in mostly small, round, non-adherent cells with several adherent cells located around the periphery of well. Non-sorted perfusate-derived cells, plated at a cell density of 93,800/cm$^2$, resulted in mostly small, round, non-adherent cells with several adherent cells located around the well peripheries.

Sorted amnion-derived cells, plated at a cell density of 6,300/cm$^2$, resulted in small, round, non-adherent cells. Non-sorted amnion-derived cells, plated at a cell density of 6,300/cm$^2$, resulted in small, round, non-adherent cells. Non-sorted amnion-derived cells plated at a cell density of 62,500/cm$^2$ resulted in small, round, non-adherent cells.

Sorted chorion-derived cells, plated at a cell density of 6,300/cm$^2$, resulted in small, round, non-adherent cells. Non-sorted chorion-derived cells, plated at a cell density of 6,300/cm$^2$, resulted in small, round, non-adherent cells. Non-sorted chorion-derived cells plated at a cell density of 62,500/cm$^2$, resulted in small, round, non-adherent cells.

The populations of placental stem cells described above, upon culture on tissue culture plastic, adhered to the surface and assumed a characteristic fibroblastoid shape.

6.3 Example 3

Collection of Placental Stem Cells by Closed-Circuit Perfusion

This Example demonstrates one method of collecting placental stem cells by perfusion.

A post-partum placenta is obtained within 24 hours after birth. The umbilical cord is clamped with an umbilical cord clamp approximately 3 to 4 inches about the placental disk, and the cord is cut above the clamp. The umbilical cord is either discarded, or processed to recover, e.g., umbilical cord stem cells, and/or to process the umbilical cord membrane for the production of a biomaterial. Excess amniotic membrane and chorion is cut from the placenta, leaving approximately ¼ inch around the edge of the placenta. The trimmed material is discarded.

Starting from the edge of the placental membrane, the amniotic membrane is separated from the chorion using blunt dissection with the fingers. When the amniotic membrane is entirely separated from the chorion, the amniotic membrane is cut around the base of the umbilical cord with scissors, and detached from the placental disk. The amniotic membrane can be discarded, or processed, e.g., to obtain stem cells by enzymatic digestion, or to produce, e.g., an amniotic membrane biomaterial.

The fetal side of the remaining placental material is cleaned of all visible blood clots and residual blood using sterile gauze, and is then sterilized by wiping with an iodine swab than with an alcohol swab. The umbilical cord is then clamped crosswise with a sterile hemostat beneath the umbilical cord clamp, and the hemostat is rotated away, pulling the cord over the clamp to create a fold. The cord is then partially cut below the hemostat to expose a cross-section of the cord supported by the clamp. Alternatively, the cord is clamped with a sterile hemostat. The cord is then placed on sterile gauze and held with the hemostat to provide tension. The cord is then cut straight across directly below the hemostat, and the edge of the cord near the vessel is re-clamped.

The vessels exposed as described above, usually a vein and two arteries, are identified, and opened as follows. A closed alligator clamp is advanced through the cut end of each vessel, taking care not to puncture the clamp through the vessel wall. Insertion is halted when the tip of the clamp is slightly above the base of the umbilical cord. The clamp is then slightly opened, and slowly withdrawn from the vessel to dilate the vessel.

Plastic tubing, connected to a perfusion device or peristaltic pump, is inserted into each of the placental arteries. Plastic tubing, connected to a 250 mL collection bag, is inserted into the placental vein. The tubing is taped into place.

A small volume of sterile injection grade 0.9% NaCl solution to check for leaks. If no leaks are present, the pump speed is increased, and about 750 mL of the injection grade 0.9% NaCl solution is pumped through the placental vasculature. Perfusion can be aided by gently massaging the placental disk from the outer edges to the cord. When a collection bag is full, the bag is removed from the coupler connecting the tubing to the bag, and a new bag is connected to the tube.

When collection is finished, the collection bags are weighed and balanced for centrifugation. After centrifugation, each bag is placed inside a plasma extractor without disturbing the pellet of cells. The supernatant within the bags is then removed and discarded. The bag is then gently massaged to resuspend the cells in the remaining supernatant. Using a sterile 1 mL syringe, about 300-500 µL of cells is withdrawn from the collection bag, via a sampling site coupler, and transferred to a 1.5 mL centrifuge tube. The weight and volume of the remaining perfusate are determined, and ⅓ volume of hetastarch is added to the perfusate and mixed thoroughly. The number of cells per mL is determined. Red blood cells are removed from the perfusate using a plasma extractor.

Placental cells are then immediately cultured to isolate placental stem cells, or are cryopreserved for later use.

6.4 Example 4

Differentiation of Placental Stem Cells 6.4.1 Induction of Differentiation into Neurons Neuronal differentiation of placental stem cells can also be accomplished as follows:
1. Placental stem cells are grown for 24 hr in preinduction medium consisting of DMEM/20% FBS and 1 mM beta-mercaptoethanol.
2. The preinduction medium is removed and cells are washed with PBS.
3. Neuronal induction medium consisting of DMEM and 1-10 mM betamercaptoethanol is added to the cells. Alternatively, induction media consisting of DMEM/2% DMSO/200 µM butylated hydroxyanisole may be used.
4. In certain embodiments, morphologic and molecular changes may occur as early as 60 minutes after exposure to serum-free media and betamercaptoethanol. RT/PCR may be used to assess the expression of e.g., nerve growth factor receptor and neurofilament heavy chain genes.

6.4.2 Induction of Differentiation into Adipocytes

Several cultures of placental stem cells derived from enzymatic digestion of amnion, at 50-70% confluency, were induced in medium comprising (1) DMEM/MCDB-201 with 2% FCS, 0.5% hydrocortisone, 0.5 mM isobutylmethylxanthine, 60 µM indomethacin; or (2) DMEM/MCDB-201 with 2% FCS and 0.5% linoleic acid. Cells were examined for morphological changes; after 3-7 days, oil droplets appeared. Differentiation was also assessed by quantitative real-time PCR to examine the expression of specific genes associated with adipogenesis, i.e., PPAR-γ2, aP-2, lipoprotein lipase, and osteopontin. Two cultures of placental stem cells showed an increase of 6.5-fold and 24.3-fold in the expression of adipocyte-specific genes, respectively. Four other cultures showed a moderate increase (1.5-2,0-fold) in the expression of PPAR-γ2 after induction of adipogenesis.

In another experiment, placental stem cells obtained from perfusate were cultured in DMEM/MCDB-201 (Chick fibroblast basal medium) with 2% FCS. The cells were trypsinized and centrifuged. The cells were resuspended in adipo-induction medium (AIM) 1 or 2. AIM 1 comprised MesenCult Basal Medium for human Mesenchymal Stem Cells (StemCell Technologies) supplemented with Mesenchymal Stem Cell Adipogenic Supplements (StemCell Technologies). AIM2 comprised DMEM/MCDB-201 with 2% FCS and LA-BSA (1%). About $1.25 \times 10^5$ placental stem cells were grown in 5 mL AIM1 or AIM2 in T-25 flasks. The cells were cultured in incubators for 7-21 days. The cells developed oil droplet vacuoles in the cytoplasm, as confirmed by oil-red staining, suggesting the differentiation of the stem cells into adipocytes.

Adipogenic differentiation of placental stem cells can also be accomplished as follows:
1. Placental stem cells are grown in MSCGM (Cambrex) or DMEM supplemented with 15% cord blood serum.
2. Three cycles of induction/maintenance are used. Each cycle consists of feeding the placental stem cells with Adipogenesis Induction Medium (Cambrex) and culturing the cells for 3 days (at 37° C., 5% $CO_2$), followed by 1-3 days of culture in Adipogenesis Maintenance Medium (Cambrex). An alternate induction medium that can be used contains 1 µM dexamethasone, 0.2 mM indomethacin, 0.01 mg/ml insulin, 0.5 mM IBMX, DMEM-high glucose, FBS, and antibiotics.
3. After 3 complete cycles of induction/maintenance, the cells are cultured for an additional 7 days in adipogenesis maintenance medium, replacing the medium every 2-3 days.
4. A hallmark of adipogenesis is the development of multiple intracytoplasmic lipid vesicles that can be easily observed using the lipophilic stain oil red O. Expression of lipase and/or fatty acid binding protein genes is confirmed by RT/PCR in placental stem cells that have begun to differentiate into adipocytes.

6.4.3 Induction of Differentiation into Osteogenic Cells

Osteogenic medium was prepared from 185 mL Cambrex Differentiation Basal Medium—Osteogenic and Single-Quots (one each of dexamethasone, l-glutamine, ascorbate, pen/strep, MCGS, and β-glycerophosphate). Placental stem cells from perfusate were plated, at about $3\times10^3$ cells per cm$^2$ of tissue culture surface area in 0.2-0.3 mL MSCGM per cm$^2$ tissue culture area. Typically, all cells adhered to the culture surface for 4-24 hours in MSCGM at 37° C. in 5% $CO_2$. Osteogenic differentiation was induced by replacing the medium with Osteogenic Differentiation medium. Cell morphology began to change from the typical spindle-shaped appearance of the adherent placental stem cells, to a cuboidal appearance, accompanied by mineralization. Some cells delaminated from the tissue culture surface during differentiation.

Osteogenic differentiation can also be accomplished as follows:
1. Adherent cultures of placental stem cells are cultured in MSCGM (Cambrex) or DMEM supplemented with 15% cord blood serum.
2. Cultures are cultured for 24 hours in tissue culture flasks.
3. Osteogenic differentiation is induced by replacing MSCGM with Osteogenic Induction Medium (Cambrex) containing 0.1 µM dexamethasone, 0.05 mM ascorbic acid-2-phosphate, 10 mM beta glycerophosphate.
4. Cells are fed every 3-4 days for 2-3 weeks with Osteogenic Induction Medium.
5. Differentiation is assayed using a calcium-specific stain and RT/PCR for alkaline phosphatase and osteopontin gene expression.

6.4.4 Induction of Differentiation into Pancreatic Cells

Pancreatic differentiation is accomplished as follows:
1. Placental stem cells are cultured in DMEM/20% CBS, supplemented with basic fibroblast growth factor, 10 ng/ml; and transforming growth factor beta-1, 2 ng/ml. KnockOut Serum Replacement may be used in lieu of CBS.
2. Conditioned media from nestin-positive neuronal cell cultures is added to media at a 50/50 concentration.
3. Cells are cultured for 14-28 days, refeeding every 3-4 days.
4. Differentiation is characterized by assaying for insulin protein or insulin gene expression by RT/PCR.

6.4.5 Induction of Differentiation into Cardiac Cells

Myogenic (cardiogenic) differentiation is accomplished as follows:
1. Placental stem cells are cultured in DMEM/20% CBS, supplemented with retinoic acid, 1 µM; basic fibroblast growth factor, 10 ng/ml; and transforming growth factor beta-1, 2 ng/ml; and epidermal growth factor, 100 ng/ml. KnockOut Serum Replacement (Invitrogen, Carlsbad, Calif.) may be used in lieu of CBS.
2. Alternatively, placental stem cells are cultured in DMEM/20% CBS supplemented with 50 ng/ml Cardiotropin-1 for 24 hours.
3. Alternatively, placental stem cells are maintained in protein-free media for 5-7 days, then stimulated with human myocardium extract (escalating dose analysis). Myocardium extract is produced by homogenizing 1 gm human myocardium in 1% HEPES buffer supplemented with 1% cord blood serum. The suspension is incubated for 60 minutes, then centrifuged and the supernatant collected.
4. Cells are cultured for 10-14 days, refeeding every 3-4 days.
5. Differentiation is confirmed by demonstration of cardiac actin gene expression by RT/PCR.

6.4.6 Induction of Differentiation into Chondrocytes

6.4.6.1 General Method

Chondrogenic differentiation of placental stem cells is generally accomplished as follows:
1. Placental stem cells are maintained in MSCGM (Cambrex) or DMEM supplemented with 15% cord blood serum.
2. Placental stem cells are aliquoted into a sterile polypropylene tube. The cells are centrifuged (150×g for 5 minutes), and washed twice in Incomplete Chondrogenesis Medium (Cambrex).
3. After the last wash, the cells are resuspended in Complete Chondrogenesis Medium (Cambrex) containing 0.01 µg/ml TGF-beta-3 at a concentration of $5\times10(5)$ cells/ml.
4. 0.5 ml of cells is aliquoted into a 15 ml polypropylene culture tube. The cells are pelleted at 150×g for 5 minutes. The pellet is left intact in the medium.
5. Loosely capped tubes are incubated at 37° C., 5% $CO^2$ for 24 hours.
6. The cell pellets are fed every 2-3 days with freshly prepared complete chondrogenesis medium.
7. Pellets are maintained suspended in medium by daily agitation using a low speed vortex.
8. Chondrogenic cell pellets are harvested after 14-28 days in culture.
9. Chondrogenesis is characterized by e.g., observation of production of esoinophilic ground substance, assessing cell morphology, an/or RT/PCR confirmation of collagen 2 and/or collagen 9 gene expression and/or the production of cartilage matrix acid mucopolysaccharides, as confirmed by Alcian blue cytochemical staining.

6.4.6.2 Differentiation of Placental and Umbilical Cord Stem Cells into Chondrogenic Cells The Example demonstrates the differentiation of placental stem cells into chondrogenic cells and the development of cartilage-like tissue from such cells.

Cartilage is an avascular, alymphatic tissue that lacks a nerve supply. Cartilage has a low chondrocyte density (<5%), however these cells are surprisingly efficient at maintaining the extracellular matrix around them. Three main types of cartilage exist in the body: (1) articular cartilage, which facilitates joint lubrication in joints; (2) fibrocartilage, which provides shock absorption in, e.g., meniscus and intervertebral disc; and (3) elastic cartilage, which provides anatomical structure in, e.g., nose and ears. All three types of cartilage are similar in biochemical structure.

Joint pain is a major cause of disability and provides an unmet need of relief in the area of orthopedics. Primary osteoarthritis (which can cause joint degeneration), and trauma are two common causes of pain. Approximately 9% of the U.S. population has osteoarthritis of hip or knee, and more than 2 million knee surgeries are performed yearly. Unfortunately, current treatments are more geared towards treatment of symptoms rather than repairing the cartilage. Natural repair occurs when fibroblast-like cells invade the area and fill it with fibrous tissue which is neither as resilient or elastic as the normal tissue, hence causing more damage. Treatment options historically included tissue grafts, subchondral drilling, or total joint replacement. More recent treatments however include CARTICEL®, an autologous chondrocyte injection; SYNVISC® and ORTHOVISC®, which are hyaluronic acid injections for temporary pain relief; and CHONDRO-GEN™, an injection of adult mesenchymal stem cells for meniscus repair. In general, the trend seems to be lying more towards cellular therapies and/or tissue engineered products involving chondrocytes or stem cells.

Materials and Methods.

Two placental stem cell lines, designated AC61665, P3 (passage 3) and AC63919, P5, and two umbilical cord stem cell lines, designated UC67249, P2 and UC67477, P3 were used in the studies outlined below. Human mesenchymal stem cells (MSC) were used as positive controls, and an osteosarcoma cell line, MC3T3, and human dermal fibroblasts (HDF) were used as negative controls.

Placental and umbilical cord stem cells were isolated and purified from full term human placenta by enzymatic digestion. Human MSC cells and HDF cells were purchased from Cambrex, and MC3T3 cells were purchased from American Type Culture Collection. All cell lines used were centrifuged into pellets in polypropylene centrifuge tubes at 800 RPM for 5 minutes and grown in both chondrogenic induction media (Cambrex) and non-inducing basal MSC media (Cambrex). Pellets were harvested and histologically analyzed at 7, 14, 21 and 28 days by staining for glycosaminoglycans (GAGs) with Alcian Blue, and/or for collagens with Sirius Red. Collagen type was further assessed with immunostaining. RNA analysis for cartilage-specific genes was performed at 7 and 14 days.

Results

Experiment 1: Chondrogenesis studies were designed to achieve three main objectives: (1) to demonstrate that placental and umbilical cord stem cells can differentiate and form cartilage tissue; (2) to demonstrate that placental and umbilical cord stem cells can differentiate functionally into chondrocytes; and (3) to validate results obtained with the stem cells by evaluating control cell lines.

For objective 1, in a preliminary study, one placental stem cell line was cultured in chondrogenic induction medium in the form of cell pellets, either with or without bone morphogenic protein (BMP) at a final concentration of 500 ng/mL. Pellets were assessed for evidence of chondrogenic induction every week for 4 weeks. Results indicated that the pellets do increase in size over time. However, no visual differences were noted between the $BMP^+$ and $BMP^-$ samples. Pellets were also histologically analyzed for GAG's, an indicator of cartilage tissue, by staining with Alcian Blue. $BMP^+$ cells generally appeared more metabolically active with pale vacuoles whereas $BMP^-$ cells were smaller with dense-stained nuclei and less cytoplasm (reflects low metabolic activity). At 7 days, $BMP^+$ cells had stained heavily blue, while $BMP^-$ had stained only faintly. By 28 days of induction, both $BMP^+$ and $BMP^-$ cells were roughly equivalently stained with Alcian Blue. Overall, cell density decreased over time, and matrix overtook the pellet. In contrast, the MC3T3 negative cell line did not demonstrate any presence of GAG when stained with Alcian Blue.

Experiment 2: Based on the results of Experiment 1, a more detailed study was designed to assess the chondrogenic differentiation potential of two placental stem cell and two umbilical cord stem cell lines. In addition to the Alcian Blue histology, cells were also stained with Sirius Red, which is specific for type II collagen. Multiple pellets were made for each cell line, with and without induction media.

The pelleted, cultured cell lines were first assessed by gross observation for macroscopic generation of cartilage. Overall, the stem cell lines were observed to make pellets as early as day 1. These pellets grew over time and formed a tough matrix, appearing white, shining and cartilage-like, and became mechanically tough. By visual inspection, pellets from placental stem cells or umbilical cord stem cells were much larger than the MSC controls. Control pellets in non-induction media started to fall apart by Day 11, and were much smaller at 28 days than pellets developed by cells cultured in chondrogenic induction medium. Visually, there were no differences between pellets formed by placental stem cells or umbilical cord. However, the UC67249 stem cell line, which was initiated in dexamethasone-free media, formed larger pellets. Negative control MC3T3 cells did not form pellets; however, HDFs did form pellets.

Representative pellets from all test groups were then subjected to histological analysis for GAG's and collagen. Generally, pellets formed by the stem cells under inducing conditions were much larger and stayed intact better than pellets formed under non-inducing conditions. Pellets formed under inducing conditions showed production of GAGs and increasing collagen content over time, and as early as seven days, while pellets formed under non-inducing conditions showed little to no collagen production, as evidenced by weak Alcian Blue staining. In general, the placental stem cells and umbilical cord stem cells appeared, by visual inspection, to produce tougher, larger pellets, and appeared to be producing more collagen over time, than the hMSCs. Moreover, over the course of the study, the collagen appeared to thicken, and the collagen type appeared to change, as evidenced by changes in the fiber colors under polarized light (colors correlate to fiber thickness which may be indicative of collagen type). Non-induced placental stem cells produced much less type II collagen, if any, compared to the induced stem cells. Over the 28-day period, cell density decreased as matrix production increased, a characteristic of cartilage tissue.

These studies confirm that placental and umbilical cord stem cells can be differentiated along a chondrogenic pathway, and can easily be induced to form cartilage tissue. Initial observations indicate that such stem cells are preferable to MSCs for the formation of cartilage tissue.

6.5 Example 5

Hanging Drop Culture of Placental Stem Cells

Placental adherent stem cells in culture are trypsinized at 37° C. for about 5 minutes, and loosened from the culture dish by tapping. 10% FBS is added to the culture to stop trypsinization. The cells are diluted to about $1\times10^4$ cells per mL in about 5 mL of medium. Drops (either a single drop or drops from a multi-channel micropipette are placed on the inside of the lid of a 100 mL Petri dish. The lid is carefully inverted and placed on top of the bottom of the dish, which contains about 25 ml of sterile PBS to maintain the moisture content in the dish atmosphere. Cells are grown for 6-7 days.

6.6 Example 6

Placental Tissue Digestion to Obtain Placental Stem Cells

This Example demonstrates a scaled up isolation of placental stem cells by enzymatic digestion.

Approximately 10 grams of placental tissue (amnion and chorion) is obtained, macerated, and digested using equal volumes of collagenase A (1 mg/ml) (Sigma) and Trypsin-EDTA (0.25%) (Gibco-BRL) in a total volume of about 30 ml for about 30 minutes at 37° C. Cells liberated by the digestion are washed 3× with culture medium, distributed into four T-225 flasks and cultured as described in Example 1. Placental stem cell yield is between about $4\times10^8$ and $5\times10^8$ cells per 10 g starting material. Cells, characterized at passage 3, are predominantly $CD10^+$, $CD90^+$, $CD105^+$, $CD200^+$, $CD34^-$ and $CD45^-$.

6.7 Example 7

Production of Cryopreserved Stem Cell Product and Stem Cell Bank

This Example demonstrates the isolation of placental stem cell and the production of a frozen stem cell-based product.

Summary: Placental tissue is dissected and digested, followed by primary and expansion cultures to achieve an expanded cell product that produces many cell doses. Cells are stored in a two-tiered cell bank and are distributed as a frozen cell product. All cell doses derived from a single donor placenta are defined as a lot, and one placenta lot is processed at a time using sterile technique in a dedicated room and Class 100 laminar flow hood. The cell product is defined as being $CD105^+$, $CD200^+$, $CD10^+$, and $CD34^-$, having a normal karyotype and no maternal cell content.

6.7.1 Obtaining Stem Cells

Tissue Dissection and Digestion: A placenta is obtained less than 24 hours after expulsion. Placental tissue is obtained from amnion, a combination of amnion and chorion, or chorion. The tissue is minced into small pieces, about 1 mm in size. Minced tissue is digested in 1 mg/ml Collagenase 1A for 1 hour at 37° C. followed by Trypsin-EDTA for 30 minutes at 37° C. After three washes in 5% FBS in PBS, the tissue is resuspended in culture medium.

Primary Culture: The purpose of primary culture is to establish cells from digested placental tissue. The digested tissue is suspended in culture medium and placed into Corning T-flasks, which are incubated in a humidified chamber maintained at 37° C. with 5% $CO_2$. Half of the medium is replenished after 5 days of culture. High-density colonies of cells form by 2 weeks of culture. Colonies are harvested with Trypsin-EDTA, which is then quenched with 2% FBS in PBS. Cells are centrifuged and resuspended in culture medium for seeding expansion cultures. These cells are defined as Passage 0 cells having doubled 0 times.

Expansion Culture: Cells harvested from primary culture, harvested from expansion culture, or thawed from the cell bank are used to seed expansion cultures. Cell Factories (NUNC™) are treated with 5% $CO_2$ in air at 50 ml/min/tray for 10 min through a sterile filter and warmed in a humidified incubator maintained at 37° C. with 5% $CO_2$. Cell seeds are counted on a hemacytometer with trypan blue, and cell number, viability, passage number, and the cumulative number of doublings are recorded. Cells are suspended in culture medium to about $2.3\times10^4$ cells/ml and 110 ml/tray are seeded in the Cell Factories. After 3-4 days and again at 5-6 days of culture, culture medium is removed and replaced with fresh medium, followed by another treatment with 5% $CO_2$ in air. When cells reach approximately $10^5$ cells/$cm^2$, cells are harvested with Trypsin-EDTA, followed by quenching with 2% FBS in PBS. Cell are then centrifuged and resuspended in culture medium.

Cryopreservation: Cells to be frozen down are harvested from culture with Trypsin-EDTA, quenched with 2% FBS in PBS, and counted on a hemacytometer. After centrifugation, cells are resuspended with 10% DMSO in FBS to a concentration of about 1 million cells/ml for cells to be used for assembly of a cell bank, and 10 million cells/ml for individual frozen cell doses. The cell solution is transferred to a freezing container, which is placed in an isopropyl alcohol bath in a −80° C. freezer. The following day, cells are transferred to liquid nitrogen.

6.7.2 Design of a Stem Cell Bank

A "lot" is defined as all cell doses derived from a single donor placenta. Cells maintained normal growth, karyotype, and cell surface maker phenotype for over 8 passages and 30 doublings during expansion culture. Given this limitation, doses comprise cells from 5 passages and about 20 doublings. To generate a supply of equivalent cells, a single lot is expanded in culture and is stored in a two-tiered cell bank and frozen doses. In particular, cells harvested from the primary culture, which are defined as Passage 0 cells having undergone 0 doublings, are used to initiate an expansion culture. After the first passage, approximately 4 doublings occur, and cells are frozen in a Master Cell Bank (MCB). Vials from the MCB are used to seed additional expansion cultures. After two additional passages of cells thawed from the MCB, cells are frozen down in a Working Cell Bank (WCB), approximately 12 cumulative doublings. Vials from the WCB are used to seed an expansion culture for another 2 passages, resulting in Passage 5 cells at approximately 20 doublings that are frozen down into individual doses.

6.7.3 Thawing Cells For Culture

Frozen containers of cells are placed into a sealed plastic bag and immersed in a 37° C. water bath. Containers are gently swirled until all of the contents are melted except for a small piece of ice. Containers are removed from the sealed plastic bag and a 10× volume of culture medium is slowly added to the cells with gentle mixing. A sample is counted on the hemacytometer and seeded into expansion cultures.

6.7.4 Thawing Cells for Injection

Frozen containers of cells are transferred to the administration site in a dry nitrogen shipper. Prior to administration, containers are placed into a sealed plastic bag and immersed in a 37° C. water bath. Containers are gently swirled until all of the contents are melted except for a small piece of ice.

Containers are removed from the sealed plastic bag and an equal volume of 2.5% HSA/5% Dextran is added. Cells are injected with no further washing.

6.7.5 Testing and Specifications

A maternal blood sample accompanies all donor placentas. The sample is screened for Hepatitis B core antibody and surface antigen, Hepatitis C Virus antibody and nucleic acid, and HIV I and II antibody and nucleic acid. Placental processing and primary culture begins prior to the receipt of test results, but continues only for placentas associated with maternal blood samples testing negative for all viruses. A lot is rejected if the donor tests positive for any pathogen. In addition, the tests described in Table 3 are performed on the MCB, the WCB, and a sample of the cell dose material derived from a vial of the WCB. A lot is released only when all specifications are met.

TABLE 3

Cell testing and specifications

| Test | Methods | Required Result |
|---|---|---|
| Sterility | BD BACTEC PEDS PLUS/F and BACTEC Myco/F Lytic | Negative |
| Endotoxin | LAL gel clot | ≤5 EU/ml* |
| Viability | Trypan Blue | >70% viable |
| Mycoplasma | Direct culture, DNA-fluorochrome (FDA PTC 1993) | Negative |
| Identity | Flow cytometry (see below) | $CD105^+$, $CD200^+$, $CD10^+$, $CD34^-$ |
| Cell Purity | Microsatellite | No contaminating cell detected |
| Karyotype | G-banding and chromosome count on metaphase cells | Normal |

*For the product designed to be 40 ml of frozen cells/dose and a maximum of 5 EU/ml, the cell product is below the upper limit of 5 EU/kg/dose for recipients over 40 kg in body weight.

6.7.6 Surface Marker Phenotype Analysis

Cells are placed in 1% paraformaldehyde (PFA) in PBS for 20 minutes and stored in a refrigerator until stained (up to a week). Cells are washed with 2% FBS, 0.05% sodium azide in PBS (Staining Buffer) and then resuspended in staining buffer. Cells are stained with the following antibody conjugates: CD105-FITC, CD200-PE, CD34-PECy7, CD10-APC. Cells are also stained with isotype controls. After 30 minute incubation, the cells are washed and resuspended with Staining Buffer, followed by analysis on a flow cytometer. Cells having an increased fluorescence compared to isotype controls are counted as positive for a marker.

6.8 Example 8

Identification of Placental Stem Cell-Specific Genes

Gene expression patterns from placental stem cells from amnion-chorion (AC) and umbilical cord (UC) were compared to gene expression patterns of multipotent bone marrow-derived mesenchymal stem cells (BM) and dermal fibroblasts (DF), the latter of which is considered to be terminally differentiated. Cells were grown for a single passage, an intermediate number of passages, and large number of passages (including until senescence). Results indicate that the number of population doublings has a major impact on gene expression. A set of genes was identified that are up-regulated in AC and UC, and either down-regulated or absent in BM and DF, and that are expressed independent of passage number. This set of placental stem cell- or umbilical cord stem cell-specific genes encodes a number of cytoskeleton and cell-to-cell adhesion proteins associated with epithelial cells and an immunoglobulin-like surface protein, CD200, implicated in maternal-fetal immune tolerance. Placental stem cells and umbilical cord stem cells will be referred to collectively hereinafter in this Example as AC/UC stem cells.

6.8.1 Methods and Materials

6.8.1.1 Cells and Cell Culture

BM (Cat# PT-2501) and DF (Cat# CC-2511) were purchased from Cambrex. AC and UC originated from passage 0 tissue culture flasks. AC and UC in the flasks were obtained by digestion from a donor placenta designated 2063919. T-75 culture flasks were seeded at 6000 cells/cm$^2$ and cells were passaged when they became confluent. Population doublings were estimated from trypan blue cell counts. Cultures were assayed for gene expression after 3, 11-14, and 24-38 population doublings.

6.8.1.2 RNA, Microarrays, and Analysis

Cells were lysed directly in their tissue culture flasks, with the exception of one culture that was trypsinized prior to lysis. Total RNA was isolated with the RNeasy kit from QIAGEN. RNA integrity and concentrations were determined with an Agilent 2100 Bioanalyzer. Ten micrograms of total RNA from each culture were hybridized on an Affymetrix GENE-CHIP® platform. Total RNA was converted to labeled cRNAs and hybridized to oligonucleotide Human Genome U133A 2.0 arrays according to the manufacture's methods. Image files were processed with the Affymetrix MAS 5.0 software, and normalized and analyzed with Agilent GeneSpring 7.3 software.

6.8.2 Results

6.8.2.1 Selection of BM-MSC, AC/UC Stem Cell, and DF Culture Time-Points for Microarray Analyses To establish a gene expression pattern unique to AC/UC stem cells, two stem cell lines, AC(6) and UC(6), were cultured in parallel with BM-MSC and DF. To maximize identifying a gene expression profile attributable to cellular origin and minimize exogenous influences all cells were grown in the same medium, seeded, and sub-cultured using the same criteria. Cells were harvested after 3 population doublings, 11-14 doublings, or 35 doublings or senescence, whichever came first. Genes whose expression in AC/UC stem cells are unchanged by time-in-culture and are up-regulated relative to BM and DF are candidates for AC/UC stem cell-specific genes.

FIG. 10 shows growth profiles for the four cell lines in the study; circles indicate which cultures were harvested for RNA isolation. In total twelve samples were collected. BM, AC(6), and UC(6) were harvested after three population doublings; these samples were regarded as being in culture for a "short" period of time. A short-term DF sample was not collected. Intermediate length cultures, 11 to 14 doublings, were collected for all cell types. Long-term cultures were collected from all cell lines at about 35 population doublings or just prior to senescence, whichever came first. Senescence occurred before 15 doublings for BM and at 25 doublings for DF. The purchased BM and DF cells were expanded many times prior to gene analysis, and cannot be considered early-stage. However, operationally, BM grown for three doublings (BM-03) are deemed a short-term culture. Likewise, BM-11 is operationally referred to as an intermediate length culture, but because senescence occurred at 14 doublings, BM-11 is most likely a long-term culture biologically.

6.8.2.2 Hierarchical Clustering Shows Relatedness between BM, AC/UC Stem Cells, and DF Microarray analysis identifies patterns of gene expression, and hierarchical clustering (HC) attempts to find similarities in the context of two dimensions—genes in the first dimension and different conditions (different RNA samples) in the second. The GeneChips used in this experiment contained over 22,000 probe sets (referred to as the "all genes list"), but many of these sets interrogate genes that are not expressed in any condition. To reduce the all genes list, genes not expressed or expressed at low levels (raw values below 250) in all samples were eliminated to yield a list of 8,215 genes.

6.8.2.3 Gene Expression Analysis Using the Line Graph View

Gene expression patterns of the 8215 genes were displayed using the line graph view in GeneSpring (FIG. 11). The x-axis shows the twelve experimental conditions and the y-axis shows the normalized probe set expression values on a log scale. The y-axis covers a 10,000-fold range, and genes that are not expressed or expressed at very low levels are set to a value of 0.01. By default the normalized value is set to 1. Each line represents a single gene (actually a probe set, some genes have multiple probe sets) and runs across all twelve conditions as a single color. Colors depict relative expression levels, as described for the heatmaps, but the coloring pattern is determined by selecting one condition. AC-03 is the selected condition in FIG. 11. Genes up-regulated relative to the normalized value are displayed by the software as red, and those that are down-regulated, are displayed as blue. The obvious upward and downward pointing spikes in AC-03 through UC-11 indicate that many genes are differentially expressed across these conditions. The striking similarity in the color patterns between AC-03 and UC-03 show that many of the same genes are up or down-regulated in these two samples. Horizontal line segments indicate that a gene's expression level is unchanged across a number of conditions. This is most notable by comparing UC-36, UC-38, and UC-38-T. There are no obvious spikes, but there is a subtle trend in that a number of red lines between UC-36 and UC-38-T are below the normalized value of 1. This indicates that these genes, which are up-regulated in AC-03 and UC-03, are down-regulated in the later cultures. The fact that the expression patterns between UC-38 and UC-38-T are so similar indicates that trypsinizing cells just prior to RNA isolation has little effect on gene expression.

In addition to the computationally intensive HC method, by visual inspection the two BM samples are more similar to each other than to the other conditions. The same is true for the two DF cultures. And despite the large number of differentially expressed genes present in the BM and DF samples, the general appearance suggests that two BMs and the two DFs are more similar to each other than to AC/UC stem cells. This is confirmed by the HC results described above.

When the above process is applied using AC-11 as the selected condition, it is clear that AC-11 and UC-11 share many of the same differentially expressed genes, but the total number of genes in common between these two conditions appears less than the number of differentially expressed genes shared by AC-03 and UC-03. FIG. 12 shows genes differentially over-expressed, by six-fold or more relative to the baseline, in AC-03. The majority of genes up-regulated in AC-03 are also up-regulated in UC-03, and more divergent in BM and DF.

6.8.2.4 Filtering Methods Used to Identifty AC/UC Stem Cell-Specific Genes

Genes that remain constant across all AC/UC samples, and are down-regulated in BM and DF, are considered AC/UC stem cell-specific. Two filtering methods were combined to create a list of 58 AC/UC stem cell-specific genes (Table 4).

TABLE 4

| 58 Placental stem cell or Umbilical cord stem cell-specific genes | | |
|---|---|---|
| Symbol | Gene | Biological Process, Description, and Additional Annotation |
| ACTG2 | actin, gamma 2, smooth muscle, enteric | muscle development, cytoskeleton, expressed in umbilical cord artery and prostate epithelia |
| ADARB1 | adenosine deaminase, RNA-specific, B1 (RED1 homolog rat) | RNA processing, central nervous system development |
| AMIGO2 | amphoterin induced gene 2 | homophilic and heterophilic cell adhesion, adhesion molecule with Ig like domain 2 |
| ARTS-1 | type 1 tumor necrosis factor receptor shedding aminopeptidase regulator | proteolysis, antigen processing, angiogenesis, expressed in placenta |
| B4GALT6 | UDP-Gal:betaGlcNAc beta 1,4-galactosyltransferase, polypeptide 6 | carbohydrate metabolism, integral to membrane, may function in intercellular recognition and/or adhesion |
| BCHE | butyrylcholinesterase | cholinesterase activity, serine esterase activity, hydrolase activity |
| C11orf9 | chromosome 11 open reading frame 9 | hypothetical protein, p53-like transcription factor, expressed in retinal pigment epithelium |
| CD200 | CD200 antigen | immunoglobulin-like, surface protein, inhibits macrophage |

TABLE 4-continued

58 Placental stem cell or Umbilical cord stem cell-specific genes

| Symbol | Gene | Biological Process, Description, and Additional Annotation |
|---|---|---|
| COL4A1 | collagen, type IV, alpha 1 | ECM, basement membrane, afibrillar collagen, contains arresten domain |
| COL4A2 | collagen, type IV, alpha 2 | ECM, biogenesis, basement membrane, coexpressed with COL 4A1, down-reg. in dysplastic epithelia |
| CPA4 | carboxypeptidase A4 | proteolytic, histone acetylation, maternal imprinted, high expression in prostate cancer cell lines |
| DMD | dystrophin (muscular dystrophy, Duchenne and Becker types) | muscle contraction, cell shape and cell size control, muscle development |
| DSC3 | desmocollin 3 | homophilic cell-cell adhesion, localized to desmosomes |
| DSG2 | desmoglein 2 | homophilic cell-cell adhesion, localized to desmosomes |
| ELOVL2 | elongation of very long chain fatty acids (FEN1/Elo2, SUR4/Elo3, yeast)-like 2 | fatty acid biosynthesis, lipid biosynthesis |
| F2RL1 | coagulation factor II (thrombin) receptor-like 1 | G-protein coupled receptor protein signaling pathway, highly expressed in colon epithelia and neuronal elements |
| FLJ10781 | hypothetical protein FLJ10781 | — |
| GATA6 | GATA binding protein 6 | transcription factor, muscle development |
| GPR126 | G protein-coupled receptor 126 | signal transduction, neuropeptide signaling pathway |
| GPRC5B | G protein-coupled receptor, family C, group 5, member B | G-protein coupled receptor protein signaling pathway, |
| ICAM1 | intercellular adhesion molecule 1 (CD54), human rhinovirus receptor | cell-cell adhesion, cell adhesion, transmembrane receptor activity, expressed in conjunctival epithelium |
| IER3 | immediate early response 3 | anti-apoptosis, embryogenesis and morphogenesis, cell growth and/or maintenance |
| IGFBP7 | insulin-like growth factor binding protein 7 | negative regulation of cell proliferation, overexpressed in senescent epithelial cells |
| IL1A | interleukin 1, alpha | immune response, signal transduction, cytokine activity, cell proliferation, differentiation, apoptosis |
| IL1B | interleukin 1, beta | immune response, signal transduction, cytokine activity, cell proliferation, differentiation, apoptosis |
| 1L6 | interleukin 6 (interferon, beta 2) | cell surface receptor linked signal transduction, immune response |
| KRT18 | keratin 18 | morphogenesis, intermediate filament, expressed in placenta, fetal, and epithelial tissues |
| KRT8 | keratin 8 | cytoskeleton organization and biogenesis, phosphorylation, intermediate filament, coexpressed with KRT1B |
| LIPG | lipase, endothelial | lipid metabolism, lipoprotein lipase activity, lipid transporter, phospholipase activity, involved in vascular biology |
| LRAP | leukocyte-derived arginine aminopeptidase | antigen processing, endogenous antigen via MHC class I; N-terminal aminopeptidase activity |
| MATN2 | matrilin 2 | widely expressed in cell lines of fibroblastic or epithelial origin, nonarticular cartilage ECM |
| MEST | mesoderm specific transcript homolog (mouse) | paternally imprinted gene, development of mesodermal tissues, expressed in fetal tissues and fibroblasts |
| NFE2L3 | nuclear factor (erythroid-derived 2)-like 3 | transcription co-factor, highly expressed in primary placental cytotrophoblasts but not in placental fibroblasts |
| NUAK1 | NUAK family, SNF1-like kinase, 1 | protein amino acid phosphorylation, protein serine-threonine kinase activity |
| PCDH7 | BH-protocadherin (brain-heart) | cell-cell adhesion and recognition, containing 7 cadherin repeats |
| PDLIM3 | PDZ and LIM domain 3 | alpha-actinin-2-associated LIM protein, cytoskeleton protein binding, expressed in skeletal muscle |
| PKP2 | plakophilin 2 | cell-cell adhesion, localized to desmosomes, found in epithelia, binds cadherins and intermediate filament |

TABLE 4-continued

58 Placental stem cell or Umbilical cord stem cell-specific genes

| Symbol | Gene | Biological Process, Description, and Additional Annotation |
|---|---|---|
| RTN1 | reticulon 1 | signal transduction; neuron differentiation, neuroendocrine secretion, membrane trafficking in neuroendocrine cells |
| SERPINB9 | serpin peptidase inhibitor, ciade B (ovalbumin), member 9 | serine protease inhibitor, coagulation, fibrinolysis, complement fixation, matrix remodeling, expressed in placenta |
| ST3GAL6 | sialyltransferase 10 | amino sugar metabolism, protein amino acid glycosylation, glycolipid metabolism, protein-lipoylation |
| ST6GALNAC5 | sialyltransferase 7E | protein amino acid glycosylation, ganglioside biosynthesis |
| SLC12A8 | solute carrier family 12 (sodium/potassium/chloride transporters), member 8 | amino acid-polyamine transporter activity, cation-chloride cotransporter 9, possible role in epithelial immunity (psoriasis) |
| TCF21 | transcription factor 21 | regulation of transcription, mesoderm development, found in epithelial cells of the kidney |
| TGFB2 | transforming growth factor, beta 2 | regulation of cell cycle, signal transduction, cell-cell signaling, cell proliferation, cell growth |
| VTN | vitronectin (serum spreading factor, somatomedin B, complement S-protein) | immune response, cell adhesion, secreted protein, binds ECM |
| ZC3H12A | zinc finger CCCM-type containing 12A | MCP-I treatment-induced protein, nucleic acid binding, hypothetical zinc finger protein |

First, 58 genes were identified by selecting those genes over-expressed ≥three-fold in at least seven of eight AC/UC stem cell conditions relative to all BM and DF samples (FIG. 13). Filtering on eight of the eight AC/UC stem cell conditions yielded a similar list. The second filtering method used "absent" and "present" calls provided by the Affymetrix MAS 5.0 software. A list was created by identifying genes absent in all BM and DF conditions and present in AC-03, AC-11, UC-03, and UC-11. Gene calls in the later AC/UC stem cell conditions were not stipulated.

The two lists overlapped significantly and were combined. The combined list was trimmed further by eliminating (1) several genes expressed at very low levels in most or all AC/UC stem cell conditions, and (2) genes carried on the Y chromosome. AC and UC cells used in this study were confirmed to be male by FISH analysis, and the BM and DF were derived from a female donor. The resulting list of 46 AC/UC stem cell-specific genes is shown in Table 5.

TABLE 5

AC/UC-Specific Genes Listed by Ontology

Cell Adhesion

AMIGO2
B4GALT6
DSC3
DSG2
ICAM1
PCDH7
PKP2
VTN

Cytoskeletal

ACTG2
DMD
KRT18
KRT8
PDLIM3

TABLE 5-continued

AC/UC-Specific Genes Listed by Ontology

Development

ADARB1
IER3
IGFBP7
IL1A
IL1B
MEST
TGFB2

ECM

COL4A1
COL4A2
MATN2
VTN

Implicated in Epithelia

ACTG2
C11orf9
COL4A1
COL4A2
DSC3
DSG2
F2RL1
ICAM1
IGFBP7
IL6
KRT18
KRT8
MATN2
PKP2
SLC12A8
TCF21

Glycosylation

B4GALT6
ST3GAL6
ST6GALNAC5

TABLE 5-continued

AC/UC-Specific Genes Listed by Ontology

Response Immune

ARTS-1
CD200
IL1A
IL1B
IL6
LRAP
SLC12A8
VTN

Proteolysis

ARTS-1
CPA4
LRAP

Signaling

F2RL1
GPR126
GPRC5B
IL1A
IL1B
IL6
RTN1
TGFB2

Transcription

C11orf9?
GATA6
NFE2L3
TCF21

This list of 46 genes encodes a collection of proteins presenting a number of ontology groups. The most highly represented group, cell adhesion, contains eight genes. No genes encode proteins involved in DNA replication or cell division. Sixteen genes with specific references to epithelia are also listed.

6.8.3 Discussion

An expression pattern specific to placental stem cells, and distinguishable from bone marrow-derived mesenchymal cells, was identified. Operationally, this pattern includes 46 genes that are over expressed in all placental stem cell samples relative to all BM and DF samples.

The experimental design compared cells cultured for short, medium, and long periods of time in culture. For AC and UC cells, each culture period has a characteristic set of differentially expressed genes. During the short-term or early phase (AC-03 and UC-03) two hundred up-regulated genes regress to the mean after eight population doublings. Without being bound by theory, it is likely that this early stage gene expression pattern resembles the expression profile of AC and UC while in the natural placental environment. In the placenta these cells are not actively dividing, they are metabolizing nutrients, signaling between themselves, and securing their location by remodeling the extracellular surroundings.

Gene expression by the intermediate length cultures is defined by rapid cell division and genes differentially expressed at this time are quite different from those differentially expressed during the early phase. Many of the genes up-regulated in AC-11 and UC-11, along with BM-03 and DF-14, are involved in chromosome replication and cell division. Based on gene expression, BM-03 appears biologically to be a mid-term culture. In this middle stage cell type-specific gene expression is overshadowed by cellular proliferation. In addition, almost every gene over expressed in the short-term AC or UC cultures is down-regulated in the middle and later stage conditions. 143 genes were up-regulated ≥five-fold during this highly proliferative phase, constituting approximately 1.7% of the expressed genes.

The long-term cultures represent the final or senescent phase. In this phase, cells have exhausted their ability to divide, and, especially for AC and UC, the absolute number of differentially expressed genes is noticeably reduced. This may be the result of cells being fully adapted to their culture environment and a consequently reduced burden to biosynthesize. Surprisingly, late BM and DF cultures do not display this same behavior; a large number of genes are differentially expressed in BM-11 and DF-24 relative to AC and UC and the normalized value of 1. AC and UC are distinguishable from BM and DF most notably in the long-term cultures.

The placental stem cell-specific gene list described here is diverse. COL4A1 and COL4A2 are coordinately regulated, and KRT18 and KRT8 also appear to be co-expressed. Eight of the genes encode proteins involved in cell to cell contact, three of which (DSC3, DSG2, and PKP2) are localized to desmosomes, intercellular contact points anchored to intermediate filament cytoskeleton proteins such as keratin 18 and keratin 8. Tight cell-to-cell contact is characteristic of epithelial and endothelial cells and not typically associated with fibroblasts. Table 3 lists 16 genes, of the 46 total, characteristic to epithelial cells. Placental stem cells are generally described as fibroblast-like small spindle-shaped cells. This morphology is typically distinct from BM and DF, especially at lower cell densities. Also of note is the expression pattern of CD200, which is present in AC/UC stem cell and absent in all BM and DF samples. Moreover, CD200 has been shown to be associated with immune tolerance in the placenta during fetal development (see, e.g., Clark et al., *Am. J. Reprod. Immunol.* 50(3):187-195 (2003)).

This subset of genes of 46 genes constitutes a set of molecular biomarkers that distinguishes AC/UC stem cells from bone marrow-derived mesenchymal stem cells or fibroblasts.

6.9 Example 6.9

Differentiation of Adherent Placental Stem Cells into Osteogenic Cells

This example describes the results of experiments demonstrating the ability of placental stem cells to differenate into osteogenic cells. This example also demonstrates the ability of such osteogenic cells to mineralize, or to contribute to mineralization, of an appropriate scaffold in vitro.

6.9.1 Expression of Osteogenic Markers by Differentiated Placental Stem Cells Initially, the ability of placental stem cells to differentiate into osteogenic precursors was assessed by monitoring alkaline phosphatase (AP) activity. AP activity is a commonly used early marker for bone formation. See, e.g., Kasten et al., 2005, *Biomaterials* 26:5879-89.

6.9.1.1 Reagents

DMEM-LG, insulin-transferrin-selenium-G supplement (ITS), penicillin-streptomycin (P/S), PicoGreen dsDNA fluorescent assay were purchased from Invitrogen (Eugene, Oreg.). MCDB201, linoleic acid, dexamethasone, L-ascorbic acid, and epidermal growth factor were purchased from Sigma (St. Louis, Mo.). Fetal bovine serum (FBS) and platelet-derived growth factor were obtained from Hyclone (Logan, Utah) and R&D Systems (Minneapolis, Minn.), respectively. Cryopreserved bone-marrow derived mesenchymal stem cells (MSC), mesenchymal stem cell growth medium (designated in this Example as "basal"), and osteogenic differentiation medium (OS) were purchased from Cambrex (East Rutherford, N.J.). See also Section 5.5.4, above.

6.9.1.2 Cell culture

Adherent placental stem cells were isolated from the placenta by one of several methods including physical disruption of tissue from several different anatomical sites within the placenta. Adherent placental stem cells were established and subcultured at $5 \times 10^3$ cells/cm² in Anthro1B medium (60% DMEM-LG, 40% MCDB201, 2% FBS, 1×P/S, 180 ng/mL linoleic acid, 0.05 µM dexamethasone, 0.1 mM L-ascorbic acid, 10 ng/mL platelet-derived growth factor and 10 ng/mL epidermal growth factor). Bone marrow-MSC were subcultured in basal medium at $5 \times 10^3$ cells/cm². For experimental studies on tissue culture polystyrene, placental stem cells and/or mesenchymal stem cells were seeded in either basal or Anthro1B medium at $5 \times 10^3$ cells/cm² then maintained in either Anthro1B medium or induced with OS for up to 5 weeks; cells were fed bi-weekly with fresh medium. For studies on 3 dimensional scaffolds, placental stem cells in a volume of 100 µl of Anthro1B medium were seeded ($2.5 \times 10^5$ cells/scaffold) on calcium phosphate (CaP, BD Biosciences, San Jose Calif.) or β-tri-calcium phosphate (TCP, Therics, Akron, Ohio; VITOSS®, Orthovita, Inc.; Malvern, Pa.; HEALOS™II; DePuy Spine, Inc.; Raynham, Mass.) scaffolds. After 1-2 hour incubation at 37° C., the wells containing the scaffolds were supplemented with 180 µl of medium. After 3-4 days, half of the samples were maintained in Anthro1B medium and the other half of the samples were induced with OS medium. Medium was exchanged on a bi-weekly basis.

6.9.1.3 Alkaline phosphatase assay

Alkaline phosphatase (AP) activity in cell lysates was determined using a calorimetric assay (Cell Biolabs, San Diego, Calif.), which measures the formation of p-nitrophenol product; AP activity was normalized to µg of DNA (to account for any differences in cell number) using the PicoGreen dsDNA fluorescent assay (Invitrogen, Eugene, Oreg.). To ascertain AP activity of cells cultured on scaffolds, cell-scaffold constructs were washed with PBS, immersed in cell lysis buffer, crushed with a pipette tip, and centrifuged at 12000 g. Supernatants were then analyzed for AP activity and DNA content as described above.

6.9.1.4 Results and Discussion

Placental stem cells and mesenchymal stem cells were seeded in either basal medium (Cambrex) or Anthro1B medium, then maintained in either basal, OS, or Anthro1B medium for 3 weeks (cells seeded in basal medium and induced with OS medium are designated as "basal-OS" in FIG. 14). As shown in FIGS. 14A and 14B, cells seeded and maintained in basal medium show the lowest AP activity, as expected, while cells seeded in basal medium and induced with OS medium show comparatively higher levels of AP activity. Interestingly, cells seeded and maintained in Anthro1B show the highest levels of AP activity, higher even than cells seeded in Anthro1B medium and induced with OS medium. Thus, this experiment demonstrated that PDACs can differentiate into osteogenic precursor cells when cultured in appropriate media.

6.9.2 Functional Characterization of PDACs Differentiation into Osteogenic Cells This example describes the results of experiments to assess the functional abilities of ostoegenic cells differentiated from placental stem cells. Specifically, the ability of the osteogenic cells to deposit a mineralized matrix was assessed. Placental stem cells were prepared and cultured as described in Example 6.9.1, above, except that placental stem cells were seeded and cultured in Anthro1B medium for 3 days, then either maintained in Anthro1B medium or induced with OS medium for 3 weeks. Mineralization was assessed by von Kossa staining, a calcium assay, and scanning electromicrograph (SEM) visualization.

6.9.2.1 Von Kossa staining

Specimens were stained for mineral by the von Kossa method. In particular, cell layers were fixed with 10% formalin for 10 minutes, incubated with 5% silver nitrate under ultraviolet light for 20 minutes, washed with deionized water, incubated with 5% thiosulfate for 5 minutes, and washed thoroughly with deionized water.

6.9.2.2 Calcium Assay

Cell monolayers were rinsed twice with phosphate-buffered saline (PBS) and scraped off the dish in 0.5N HCl. Accumulated calcium was extracted from the cellular component by incubating overnight at 4 C on an orbital shaker, followed by centrifugation at 2000 g for 10 minutes. The supernatant was used for calcium determination using a calcium quantification kit from Stanbio Laboratory (Boerne, Tex.). Calcium levels were normalized to total cell protein to account for any differences in cell number.

6.9.2.3 SEM Analysis

Samples for SEM were fixed in 10% formalin for 15 minutes, washed with PBS, and dehydrated in a graded series of ethanol (20, 40, 60, 80, and 100%). Scaffolds were embedded in paraffin after ethanol dehydration to facilitate sectioning. After sectioning, samples were incubated in xylene and dehydrated in a graded series of ethanol as described above. All specimens were then sputter coated with gold and analyzed using a JEOL JSM-6400F field emission SEM (Evans Analytical Group, East Windsor, N.J.).

6.9.2.4 Results and Discussion

As shown in FIG. 15A, adherent placental stem cells induced with OS medium show evidence of calcium deposits by von Kossa staining; these deposits were not observed in cells maintained in Anthro1B medium. To quantify these levels of mineralized matrix, calcium associated with cell monolayers was determined. As shown in FIG. 15B, threefold more calcium was recovered from cell layers induced with OS medium compared to those cultured in Anthro1B medium. Together with the von Kossa staining data, the calcium extraction results show that placental stem cells induced with OS medium form mineralized matrix. To visualize mineralized matrix at a high resolution, samples of placental stem cells either maintained in Anthro1B medium (FIG. 16A) or induced with OS medium (FIG. 16B) were subjected to SEM analysis.

Deposits of matrix mineralized are clearly evident in placental stem cells induced with OS medium, while no such accumulations of mineralized deposits are seen in placental stem cells cultured in Anthro1B medium. Elemental mapping of deposits in FIG. 16B by X-ray analysis confirm that these nodules are composed of calcium and phosphate.

The apparent lack of correlation between results in FIG. 14 (increased AP activity in the presence of Anthro1B medium) and FIGS. 15 and 16 (lack of mineralization in the presence of Anthro1B medium) can be explained by the fact that Anthro1B does not contain β-glycerophosphate, which is required as a source of phosphate for mineralization of the matrix. Dexamethasone and ascorbic acid, which are present in Anthro1B medium as well as OS medium, are common inducers of osteogenic differentiation in stem cells. See, e.g., Sun et al., 2006, *Biomaterials* 27:5651-7. β-glycerophosphate is usually included in osteogenic differentiation medium as a source of phosphate to enable cell-mediated mineralization of the matrix; it is not, in general, recognized as an inducer per se of osteogenic differentiation. The AP activity data suggests that placental stem cells seeded and maintained in Anthro1B have the highest osteogenic differentiation potential; it is quite probable that mineralization was not observed in placental stem cells cultured in Anthro1B medium due to the lack of β-glycerophosphate.

6.9.3 Differentiation of PDACs on a Three Dimensional Scaffold

This example describes differentiation of placental stem cells into osteogenic cells on a three dimensional substrate. Since calcium phosphate- and apatitite-based biomaterials have been clinically applied for the treatment of fractures and bone defects, two commercially available ceramic scaffolds were chosen to evaluate placental stem cell attachment and osteogenic functionality on 3 dimensional (3D) scaffolds. Placental stem cells and mesenchymal stem cells were seeded onto scaffolds and evaluated for their ability to attach and remain adherent to the scaffolds during long-term in vitro culture. As shown in FIG. 17, placental stem cells, as well as mesenchymal stem cells, preferentially attach to β-tri-calcium phosphate (TCaP) compared to calcium phosphate (CaP) scaffolds, with placental stem cells and mesenchymal stem cells showing similar levels of attachment to TCaP scaffolds. In addition, throughout the duration of the time course, there are consistently more cells (both placental stem cells and mesenchymal stem cells) present on TCaP versus CaP scaffolds. By the second week of culture, both adherent placental stem cells and mesenchymal stem cells were no longer detectable on CaP scaffolds. These data are supported by analysis of oxygen consumption in culture medium using oxygen sensor plates. Together, these results suggest, at least under certain conditions, that TCaP scaffolds are more preferable for maintaining PDAC viability than CaP scaffolds.

To assess osteogenic differentiation on scaffolds, AP activity of cells cultured on scaffolds was monitored in an AP assay performed as described above. Placental stem cells and mesenchymal stem cells were seeded in Anthro1B medium then either maintained in Anthro1B medium or OS medium for the duration of the experiment. As shown in FIG. 18, placental stem cells on TCaP scaffolds show similar AP activity whether cultured in Anthro1B medium or OS medium, while MSC on TCaP scaffolds displayed higher AP activity in Anthro medium than cells cultured in OS medium. These results are consistent with AP activity data obtained on 2D surfaces, namely that factors present in Anthro1B medium may be stimulating AP activity to similar levels as OS medium. For both MSCs and PDACs, no AP activity was detected in cells seeded on CaP scaffolds.

To functionally assess placental stem cell bone matrix formation on 3D scaffolds, adherent placental stem cells seeded on scaffolds and cultured in either Anthro1B or OS medium for 3-5 weeks were subjected to SEM analysis. As shown in FIG. 19, SEM of TCaP scaffold which were cultured in the absence of cells showed a highly porous surface (denoted by an arrow) by the presence of abundant pores. Scaffolds cultured with either placental stem cells or mesenchymal stem cells show a lack of surface porosity, suggesting that cells are forming a monolayer consisting of either or both cell bilayers or extracellular matrix proteins surrounding the scaffold.

To elucidate whether mineralized bone matrix formation was occurring inside the scaffolds by cells, cross sections of the cell-TCaP scaffold construct were analyzed by SEM at a high resolution (5000×). As shown in FIG. 19, scaffolds cultured in the absence of cells were characterized by sharp edges of the TCaP crystal composing the scaffold. However scaffolds seeded with placental stem cells or mesenchymal stem cells lack these sharp edges and instead are decorated with nodular structures, closely resembling those observed in FIG. 17, suggesting the formation of mineralized bone matrix by both placental stem cells and mesenchymal stem cells on TCaP scaffolds.

6.10 Example 10

Differentiation of Placental Stem Cells into Osteogenic Precursors

This example describes the results of experiments assessing the differentiation of placental stem cells isolated by perfusion into osteogenic precursor cells. Cells were isolated from human placenta by perfusion according to Example 6.3.

Following collection, the human placental perfusate (HPP) cells were cultured in DMEM medium containing 10% FBS or OS for 10 days on VITOSS® (Orthovita, Inc.; Malvern, Pa.). Cells were pelleted by centrifugation at 1,200 rpm for 5 min. After removal of the remaining fluid from the cell pellets, cells were resuspended in 20 μl of PBS-2% fetal bovine serum at the designated cell numbers (25 k, 50 k or 100 k). Scaffolds were then cut into 2×3×5 mm$^3$ pieces and placed in the wells of 96-well plates. Cell suspensions were loaded directly onto the scaffolds and incubated at 37° C. with the presence of 5% $CO_2$ for 30 min followed by dispensing 200 μl of Cambrex Osteogenic Differentiation medium (Cat. #PT-3002) to immerse cell-scaffolds. For cell viability assay, scaffolds loaded with cells were transferred to the BD Oxygen Biosensor System (BD Biosciences, Cat# 353830) and immersed by 200 μl of Cambrex Osteogenic Differentiation medium.

Osteogenic potential was then evaluated by staining and by monitoring AP activity. In particular, cells were stained with alizarin red according to conventional techniques for the presence of calcium. As shown in FIG. 20, both the stem cells and MSCs deposited a calcium-containing mineralized matrix in OS medium, but not in DMEM.

AP assays were performed after culturing in OS for ten days. To do so, HPP on scaffolds were lysed in 100 μl of PBS containing 0.2% Triton X-100 by freezing and thawing for two times. 5 μl of cell lysate was used for measuring the alkaline phosphatase activity by using BioAssay Systems' QuantiChrom Alkaline Phosphatase Assay Kit (Cat# DALP- 250) as instructed by the vendor guideline. Results of the assays are presented in FIG. 21, which shows that both MSCs and HPPs exhibited AP activity following 10 days' culturing in OS medium. Thus, these experiments demonstrate that the stem cell fraction containing cells obtained as described above also had the ability to differentiate into osteogenic precursor cells.

6.11 Example 11

In Vivo Models for Bone Repair with Compositions Comprising Placental Stem Cells This example describes experiments that are performed in order to assess treatment of bone defects with compositions comprising placental stem cells. Several models of bone disease are adapted to assess application of such treatments to different bone diseases.

To model cranial bilateral defect, a defect of 3 mm×5 mm is surgically created on each side of the cranium of male athymic rats. The defects are treated with matrix only, matrix in combination with PDACs, and matrix in combination with HPPs. The amounts of PDACs are varied to assess dose-dependency of the different treatments. Different matrix materials are also assessed in order to test the effects of different combinations of matrix and stem cells.

Six rats are assigned to each treatment group and the defects are filled with the designated matrix and cell combination. At four weeks, serum is collected and rats are sacrificed. Serum is tested for immunologic reaction to the implants. Rat crania are collected for microradiography and placed in 10% NBF.

Calvariae are processed for paraffin embedding and sectioning. Coronal histological sections of the calvariae are stained with toluidine stain according to conventional techniques. Bone ingrowth into the defect and remnant of matrix carrier is assessed according to a 0 to 4 scale, with four being the largest amount of ingrowth. Inflammation and fibrosis is also assessed.

Treatment of bone lesions resulting from cancer metastestes can be assessed according to an adaptation of the procedure of Bäuerle et al., 2005, *Int. J. Cancer* 115:177-186. Briefly, site-specific osteolytic lesions are induced in nude rats by intra-arterial injection of human breast cancer cells into an anastomosing vessel between the femoral and the iliac arteries. The metastases are then either treated with conventional anti-cancer therapies (e.g., chemotherapeutic, radiological, immunological, or other therapy) or surgically removed. Next, the lesions remaining from the cancer metastases are filled with different matrix combinations as described above. After an appropriate period of time, as determined by radiologically monitoring the animals, the animals are sacrificed. Immunologic response against the matrix, inflammation, fibrosis, degree of bone ingrowth, and amount of matrix carrier are assessed.

Additional references that describe models of bone disease that can be used or adapted to assess the efficacy of compositions comprising placental stem cells to treat bone defects include Mitsiades et al., 2003, *Cancer Res.* 63:6689-96; Chakkalakal et al., 2002, *Alcohol Alcoholism* 37:13-20; Chiba et al., 2001, *J. Vet. Med. Sci.* 63:603-8; Garrett et al., 1997, *Bone* 20:515-520; and Miyakawa et al., 2003, *Biochem. Biophys. Res. Comm.* 313:258-62.

6.12 Example 12

Production of Mineralized Collagen from Human Placenta Collagen

Figure 22A:
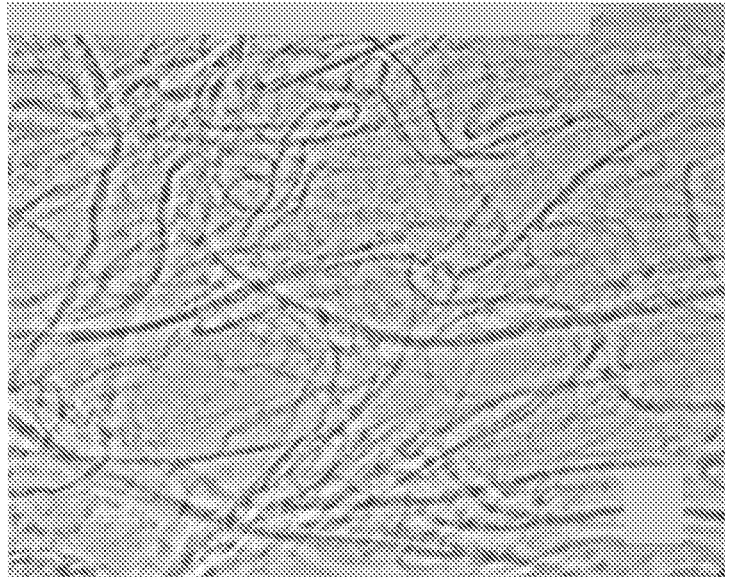
Figure 22B:
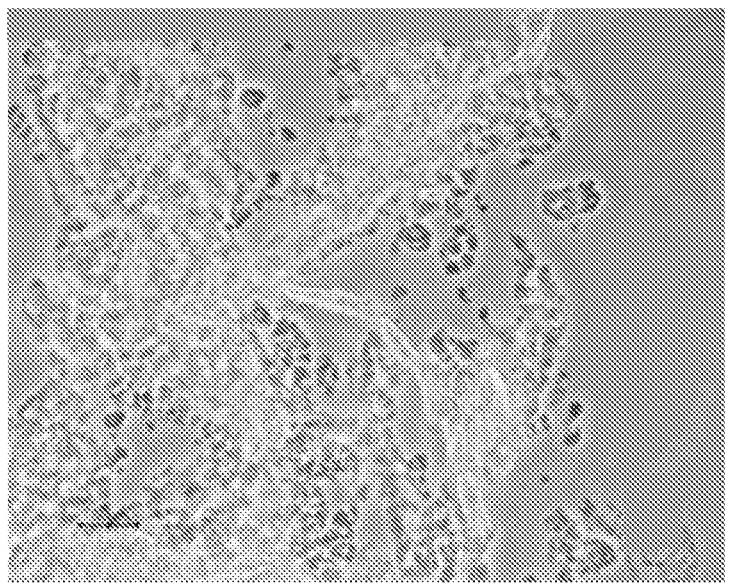

A 4° C. human placental collagen (HPC) solution at ~3 mg/ml was combined with a neutralizing buffer (200 mM $Na_2HPO_4$, pH 9.2) in an 85:15 ratio to give a final $Na_2HPO_4$ concentration of 30 mM and a pH of 7.2. Slight pH adjustments were accomplished with the addition of 1 N NaOH or HCl while stirring. Once the pH was adjusted, stirring was stopped and the reaction was ramped at 1° C./min to 32° C. The reaction was isothermed for 20-24 hours and the fibrillar collagen was isolated by centrifugation. The collagen was resuspended 3× with phosphate buffered saline (PBS, 20 mM $Na_2HPO_4$, 130 mM NaCl, pH 7.4) and centrifuged to isolate collagen. The final washed fibrillar collagen was resuspended to 10 mg/ml in PBS and stored at 4° C. until used. Fibrillation of HPC reconstitutes the soluble collagen as short fibrils and long fibers as shown in FIG. 22a.

6.12.1 Mineralization of Collagen Fibrils

To mineralize the collagen, $Ca(OH)_2$ was dispersed at 199.9 mmol/L while a 59.7 mM solution of $H_3PO_4$ was made. The $Ca(OH)_2$ and the $H_3PO_4$ were combined together in a 2:1 ratio, respectively, and the pH was adjusted to 9 in a water jacket reaction vessel. This produces a 1.67 Ca/P ratio. The reaction was stirred vigorously while the temperature was held at 40° C. and the pH was held at 9 by a circulating water bath and an automatic titration unit, respectively. Fibrillar collagen in PBS was slowly added to the reaction mixture and the pH was returned to 9. The final mineral to collagen ration was 80:20. The reaction was stirred vigorously for 18 hours and the mineralized collagen (MC) was isolated by centrifugation and washed 3 times with PBS. During the mineralization reaction a Ca—P mineral formed along the fibers as shown in the electromicrograph presented as FIG. 22b. The final reaction yield was high (>80%), and the final mineral/collagen ratio of the material was close to the input mineral/collagen ratio as determined using TGA (FIG. 23).

6.12.2 Crosslinking of Composite

The mineralized collagen (MC) was resuspended to approximately 2.5 mg/ml collagen in PBS and placed in a water jacket reaction vessel. The pH was adjusted to 9.5 and held constant throughout the reaction with an automatic titration unit, while the temperature was held constant at 25° C. with a circulating water bath. Butane diol digycidyl ether (BDDE) was added to a final concentration of 50 mM. The reaction was stirred vigorously for 24 hours at which time the product was isolated by centrifugation, washed once with PBS, and resuspended in PBS with 0.5M glycine (pH 10) to quench any unreacted residual epoxide groups. The reaction was stirred vigorously at 25° C. for 24 hours and then washed 3 times with PBS. Centrifugation was used to isolate the crosslinked mineralized collagen (CMC). The CMC formulations were characterized by light and scanning electron microscopy, Thermo Gravimetric Analysis (TGA), Differential Scanning Calorimetry (DSC) X-ray diffractometer (XRD), and Fourier Transform Infrared Spectroscopy (FTIR).

Crosslinking was confirmed by an increase in the denaturation temperature of the collagen from ~50 to ~70° C. as determined by DSC. The crosslinked material had more mechanical integrity than the non-crosslinked material and appeared more fibrous when examined by stereo microscopy and scanning electron microscopy (SEM). FTIR indicated the presence of a carbonated calcium phosphate mineral. XRD confirmed that the mineral is a poorly crystallized hydroxyapatite.

6.13 Example 13

Growth of PDACs on a Mineralized Human Placental Collagen Matrix

This Example describes the results of experiments assessing the ability of adherent placental stem cells to attach and grow on a mineralized HPC matrix. In these experiments, CMCs produced as described above were sterilized with antibiotic and antimycotic reagents. Wet samples were loaded into transwells for non-contact cytotoxicity studies using placental stem cells in a standard lactose dehydrogenase cytotoxicity assay (LDH) according to the manufacturer's instructions. LDH released into the culture medium was correlated to cytotoxicity.

Next, CMC prepared as described above was used for PDAC adhesion and proliferation studies. Placental stem cells were seeded onto CMC as described above. PDAC cell numbers were analyzed using a PicoGreen DNA assay at 1, 5 and 7 days (Molecular Probes; Eugene, Oreg.). PDACs showed similar LDH production when exposed to CMC as when exposed to tissue culture polystyrene (TCPS), indicating low cytotoxicity of CMCs. PDACs also attached in greater numbers to CMC than to non-crosslinked mineralized collagen at all seeding densities tested. Seven days after seeding, this trend continued, with placental stem cells having the highest cell numbers on CMC.

6.14 Example 14

Repair of Cranial Defects Using Placental Stem Cells and Implantable Matrix Tissue engineering using stem cells is emerging as a promising alternative to tissue or organ transplantation. Novel stem cells isolated from postpartum placenta (Placenta-Derived Adherent Cells, PDACs) have characteristics and phenotype of multi-potential stem cells. PDACs constitute an important and non-controversial source of stem/progenitor cells that could be used as a therapeutic option for the repair of damaged or diseased tissue. In the present study, we investigated the osteogenic behavior of PDACs in vitro and in vivo.
Methods In vitro study: Placental stem cells were obtained from the placenta by physical disruption of tissue from different anatomical sites, seeded in basal medium, and then induced with osteogenic differentiation medium (OS) as described above. The in vitro osteogenesis activity of PDACs was evaluated by alkaline phosphatase (AP) activity and mineralization of the extracellular matrix was detected by Alizarin Red staining. Placental stem cell loading and viability on 3 dimensional scaffolds was determined using a DNA assay and the CELL-TITER GLO® Luminescent assay respectively.

In vivo study: Placental stem cells were loaded on scaffolds (either VITOSS® Orthovita or HEALOS™ DePuy) and cultured for up to 1 hour in vitro to form cell/scaffold constructs for implantation. For the ectopic model, placental stem cell-loaded VITOSS® constructs were implanted subcutaneously into 40 athymic rats and collected 6 weeks after implantation. Explants were analyzed by immuno-histochemistry (IHC). For the bone defect model, bilateral cranial defects (3 mm×5 mm) were created in 96 male Hsd:RH-Foxn$^{rnu}$ athymic rats (Charles River, Wilmington, Mass.), and used to compare the osteogenic/repair potential of placental stem cells+HEALOS™, bone morphogenic protein-2 (BMP-2)+HEALOS™ as a positive control, scaffold (HEALOS™) alone as a negative control, and empty defects (no treatment). Rats were approximately 6 weeks old at the time of the study, and sixteen rats were assigned to each group. Explants for experimental conditions were loaded with 500 µL of a stem cell suspension at $5 \times 10^6$ cells per milliliter. Positive control comprised 5 µg BMP-2 per 25 mg carrier. Negative control comprised HEALOS with 500 µL cell culture medium. Explants were collected at 3 or 7 weeks after implantation, and analyzed with microradiograph, mineralized tissue density (imaging software-ImageJ 1.37v), Lunar PIXI x-ray densitometer, and histology. Histology was performed on excised bone tissue using hematoxylin & eosin, T-blue and vimentin stains.
Results The in vitro osteogenic behavior of placental stem cells was demonstrated by the induction of AP activity and the cells' capacity to form Alizarin Red positive deposits. In vivo results: The placental stem cell+VITOSS® subcutaneous explants showed positive immunohistochemical staining for human osteocalcin, demonstrating the in vivo osteogenic potential of the placental stem cells. In the cranial defect study, 3 week placental stem cell+HEALOS™ explants presented considerable bone formation on histology and high density mineralization on x-ray and PIXI; these osteogenic activities were increased at 7 weeks after implantation. Representative histology slides, micro radiographs, and semi-quantitative measurement of mineralization of the defect area are depicted in FIGS. 24-26. These results demonstrate the ability of placental stem cells, in conjunction with a scaffold, to augment the bone repair process.

CONCLUSIONS

Adherent placental stem cells differentiate functionally along an osteogenic pathway given the appropriate stimuli in vitro, and demonstrate significant enhancement of bone repair in vivo as compared to cell-free conditions. Therefore, from these studies we conclude that placental stem cells can be used as a cellular therapeutic in bone tissue engineering applications with proper scaffolds.

EQUIVALENTS

The compositions and methods provided herein are not to be limited in scope by the specific embodiments described herein. Indeed, various modifications of the embodiments in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A method for treating a bone defect in a subject, wherein said bone defect is an osteolytic lesion associated with multiple myeloma, bone cancer, or metastatic cancer characterized by bone metastases, comprising administering to a subject in need thereof an implantable or injectable composition comprising a population of placental stem cells, wherein said population is predominantly CD34$^-$, CD10$^+$, CD105$^+$, and CD200$^+$, and wherein said stem cells express HLA-G, thereby treating the bone defect in the subject.

2. The method of claim 1, wherein said placental stem cells have been passaged at least five times.

3. The method of claim 1, wherein said population is predominantly CD34$^-$, CD45$^-$, CD10$^+$, CD90$^+$, CD105$^+$, and CD200$^+$.

4. The method of claim 1, wherein said placental stem cells comprise at least 70% of cells in said composition.

5. The method of claim 1, wherein said placental stem cells comprise at least 90% of cells in said composition.

6. The method of claim 1, wherein said osteolytic lesion is an osteolytic lesion associated with multiple myeloma.

7. The method of claim 1, wherein said osteolytic lesion is an osteolytic lesion associated with bone cancer.

8. The method of claim 1, wherein said osteolytic lesion is an osteolytic lesion associated with metastatic cancer.

9. The method of claim 1, wherein said placental stem cells are cells from a placental stem cell bank.

10. The method of claim 1, wherein said composition is formulated as a suspension or liquid that can be administered intravenously.

11. The method of claim 1, wherein said composition comprises $5 \times 10^6$ said placental stem cells per milliliter.

12. The method of claim 1, wherein said composition comprises an implantable substrate or matrix.

13. The method of claim 1, wherein said composition comprises human serum albumin (HSA) and dextran-40.

14. The method of claim 1, wherein said placental stem cells are autologous to said subject.

15. The method of claim 1, wherein said placental stem cells have been cryopreserved.

16. The method of claim 1, wherein said population is predominantly $CD73^+$.

17. The method of claim 16, wherein at least 80% of the placental stem cells in said population are $CD73^+$, $CD105^+$, and $CD200^+$.

18. The method of claim 16, wherein at least 90% of the placental stem cells in said population are $CD73^+$, $CD105^+$, and $CD200^+$.

19. The method of claim 1, wherein said population has been passaged at least three times.

20. The method of claim 19, wherein said population has been passaged no more than ten times.

\* \* \* \* \*